United States Patent
Harris et al.

(10) Patent No.: US 10,358,604 B2
(45) Date of Patent: Jul. 23, 2019

(54) METHOD FOR STOPPING AND RESTARTING A FISCHER-TROPSCH PROCESS

(71) Applicant: Velocys, Inc., Plain City, OH (US)

(72) Inventors: Roger A. Harris, North Dublin, OH (US); Deshmukh R. Soumitra, Plain City, OH (US); Paul E. Kennedy, Tulsa, OK (US); Robert Dwayne Litt, Westerville, OH (US); Lucas D. Schrader, Worthington, OH (US); Andre P. Steynberg, Dublin, OH (US); Steven T. Perry, Galloway, OH (US)

(73) Assignee: Velocys, Inc., Plain City, OH (US)

( * ) Notice: Subject to any disclaimer, the term of this patent is extended or adjusted under 35 U.S.C. 154(b) by 0 days.

(21) Appl. No.: 15/208,902

(22) Filed: Jul. 13, 2016

(65) Prior Publication Data

US 2016/0362611 A1    Dec. 15, 2016

Related U.S. Application Data

(63) Continuation of application No. 15/178,902, filed on Jun. 10, 2016, now abandoned.
(Continued)

(51) Int. Cl.
*C10G 2/00* (2006.01)
*B01J 19/00* (2006.01)
(Continued)

(52) U.S. Cl.
CPC .......... *C10G 2/332* (2013.01); *B01J 19/0093* (2013.01); *C07C 29/151* (2013.01); *C07C 41/01* (2013.01);
(Continued)

(58) Field of Classification Search
CPC .......... B01J 19/0093; B01J 2219/00835; B01J 2219/00873; B01J 2219/00891;
(Continued)

(56) References Cited

U.S. PATENT DOCUMENTS 3,882,049 A    5/1975    Bertolacini et al. .......... 252/466
3,972,837 A    8/1976    Acres et al.
(Continued)

FOREIGN PATENT DOCUMENTS

DE          246257        6/1987
DE       39 26 466 A1    2/1991
(Continued)

OTHER PUBLICATIONS

Berge et al.; "XANES study of the susceptibility of nano-sized cobalt crystallites to oxidation during realistic Fischer-Tropsch synthesis"; Applied Catalysis A: General 312 (2006) 12-19.
(Continued)

*Primary Examiner* — Medhanit W Bahta
(74) *Attorney, Agent, or Firm* — Renner, Otto, Boisselle & Sklar, LLP

(57) ABSTRACT

The disclosed invention relates to a method for restarting a synthesis gas conversion process which has stopped. The synthesis gas conversion process may be conducted in a conventional reactor or a microchannel reactor. The synthesis gas conversion process may comprise a process for converting synthesis gas to methane, methanol or dimethyl ether. The synthesis gas conversion process may be a Fischer-Tropsch process.

13 Claims, 14 Drawing Sheets

Related U.S. Application Data

(60) Provisional application No. 62/174,772, filed on Jun. 12, 2015.

(51) Int. Cl.
*C07C 29/151* (2006.01)
*C07C 41/01* (2006.01)

(52) U.S. Cl.
CPC .............. *C10G 2/30* (2013.01); *C10G 2/341* (2013.01); *B01J 2219/0086* (2013.01); *B01J 2219/00783* (2013.01); *B01J 2219/00786* (2013.01); *B01J 2219/00806* (2013.01); *B01J 2219/00822* (2013.01); *B01J 2219/00826* (2013.01); *B01J 2219/00828* (2013.01); *B01J 2219/00835* (2013.01); *B01J 2219/00869* (2013.01); *B01J 2219/00873* (2013.01); *B01J 2219/00891* (2013.01); *C10G 2300/1022* (2013.01); *C10G 2300/4031* (2013.01)

(58) Field of Classification Search
CPC .. B01J 35/023; B01J 8/22; B01J 2208/00637; B01J 23/75; B01J 23/8472; C07C 29/151; C07C 41/01; C10G 2/30; C10G 2/332; C10G 2/341; C10G 2300/1022; C10G 2300/4031
See application file for complete search history.

(56) References Cited

U.S. PATENT DOCUMENTS

| | | | |
|---|---|---|---|
| 4,089,810 A | 5/1978 | Diwell et al. | |
| 4,096,095 A | 6/1978 | Cairns | |
| 4,289,652 A | 9/1981 | Hunter et al. | |
| 4,392,362 A | 7/1983 | Little | 62/514 |
| 4,516,632 A | 5/1985 | Swift et al. | 165/167 |
| 4,585,798 A | 4/1986 | Beuther et al. | 518/715 |
| 4,738,948 A | 4/1988 | Iglesia et al. | 502/325 |
| 5,036,032 A | 7/1991 | Iglesia et al. | 502/260 |
| 5,248,251 A | 9/1993 | Dalla Betta et al. | |
| 5,309,637 A | 5/1994 | Moriarty | 29/890.054 |
| 5,317,805 A | 7/1994 | Hoopman et al. | 29/890.03 |
| 5,382,741 A | 1/1995 | Astbury et al. | 585/652 |
| 5,534,328 A | 7/1996 | Ashmead et al. | 428/166 |
| 5,569,455 A | 10/1996 | Fukui et al. | 422/174 |
| 5,611,214 A | 3/1997 | Wegeng et al. | 62/498 |
| 5,727,618 A | 3/1998 | Mundinger et al. | 165/80.4 |
| 5,733,839 A | 3/1998 | Epinoza et al. | 502/336 |
| 5,811,062 A | 9/1998 | Wegeng et al. | 422/129 |
| 5,858,314 A | 1/1999 | Hsu et al. | 422/211 |
| 6,040,266 A | 3/2000 | Fay, III et al. | |
| 6,075,062 A | 7/2000 | Zennaro et al. | 518/715 |
| 6,090,742 A | 7/2000 | Culross | |
| 6,121,190 A | 9/2000 | Zennaro et al. | |
| 6,126,723 A | 10/2000 | Drost et al. | 96/4 |
| 6,129,973 A | 10/2000 | Martin et al. | 428/166 |
| 6,136,868 A | 10/2000 | Culross et al. | 518/700 |
| 6,156,698 A | 12/2000 | Lida et al. | 502/439 |
| 6,192,596 B1 | 2/2001 | Bennett et al. | 34/76 |
| 6,200,536 B1 | 3/2001 | Tonkovich et al. | 422/177 |
| 6,211,255 B1 | 4/2001 | Schanke et al. | 518/715 |
| 6,216,343 B1 | 4/2001 | Leland et al. | 29/890.032 |
| 6,220,497 B1 | 4/2001 | Benz et al. | 228/118 |
| 6,230,408 B1 | 5/2001 | Ehrfeld et al. | 29/890.039 |
| 6,262,131 B1 | 7/2001 | Arcuri et al. | 518/700 |
| 6,313,393 B1 | 11/2001 | Drost | 136/201 |
| 6,352,577 B1 | 3/2002 | Martin et al. | 96/4 |
| 6,353,035 B2 | 3/2002 | Manzer et al. | 518/700 |
| 6,368,997 B2 | 4/2002 | Herron et al. | 502/302 |
| 6,381,846 B2 | 5/2002 | Insley et al. | 29/890.039 |
| 6,415,860 B1 | 7/2002 | Kelly et al. | 165/748 |
| 6,440,895 B1 | 8/2002 | Tonkovich et al. | |
| 6,451,864 B1 | 9/2002 | Wang et al. | 518/715 |
| 6,476,085 B2 | 11/2002 | Manzer et al. | 518/715 |
| 6,479,428 B1 | 11/2002 | Tonkovich et al. | 502/302 |
| 6,488,838 B1 | 12/2002 | Tonkovich et al. | 208/108 |
| 6,491,880 B1 | 12/2002 | Wang et al. | 422/211 |
| 6,537,945 B2 | 3/2003 | Singleton et al. | 502/327 |
| 6,540,975 B2 | 4/2003 | Tonkovich et al. | 423/659 |
| 6,558,634 B1 | 5/2003 | Wang et al. | 422/173 |
| 6,660,237 B2 | 12/2003 | Wang et al. | 422/222 |
| 6,675,875 B1 | 1/2004 | Vafai et al. | 165/80.4 |
| 6,746,651 B1 | 6/2004 | Ponzo et al. | 422/220 |
| 6,746,819 B1 | 6/2004 | Schmitz et al. | 430/272.1 |
| 6,747,178 B1 | 6/2004 | Harston et al. | 570/175 |
| 6,749,814 B1 | 6/2004 | Bergh et al. | 422/130 |
| 6,749,817 B1 | 6/2004 | Mulvaney, III | 422/200 |
| 6,755,211 B1 | 6/2004 | O'Connor et al. | 137/554 |
| 6,756,340 B2 | 6/2004 | Voskoboynikov et al. | 502/328 |
| 6,756,515 B2 | 6/2004 | Rende et al. | 585/444 |
| 6,764,660 B1 | 7/2004 | Wiede, Jr. et al. | 422/198 |
| 6,769,444 B2 | 8/2004 | Guzman et al. | 137/15.01 |
| 6,770,245 B2 | 8/2004 | Akporiaye et al. | 422/82.12 |
| 6,773,684 B2 | 8/2004 | Lesieur et al. | 422/198 |
| 6,824,689 B2 | 11/2004 | Wang et al. | |
| 6,989,403 B2 | 1/2006 | Huang et al. | 518/709 |
| 7,045,486 B2 | 5/2006 | Wang et al. | 502/439 |
| 7,084,180 B2 | 8/2006 | Wang et al. | 518/712 |
| 7,722,833 B2 | 5/2010 | Wang et al. | 422/198 |
| 7,829,602 B2 | 11/2010 | Litt et al. | |
| 8,100,996 B2 | 1/2012 | Simmons et al. | 48/197 |
| 8,933,136 B2 | 1/2015 | Bezemer et al. | 518/712 |
| 9,006,298 B2 | 4/2015 | Leviness et al. | 518/715 |
| 9,023,900 B2 | 5/2015 | Wang et al. | 502/325 |
| 2002/0028853 A1 | 3/2002 | Manzer et al. | 518/713 |
| 2002/0048541 A1 | 4/2002 | Schodel et al. | 422/198 |
| 2002/0188031 A1 | 12/2002 | Kibby | 518/715 |
| 2003/0083390 A1* | 5/2003 | Shah | C01B 3/36 518/702 |
| 2003/0087971 A1 | 5/2003 | Steynberg et al. | |
| 2003/0105171 A1 | 6/2003 | Subramanian et al. | 518/715 |
| 2003/0116503 A1 | 6/2003 | Wang et al. | 210/660 |
| 2003/0185721 A1 | 10/2003 | Wang et al. | 422/177 |
| 2003/0219903 A1 | 11/2003 | Wang et al. | 436/37 |
| 2004/0059008 A1* | 3/2004 | Raje | B01J 23/94 518/726 |
| 2004/0104010 A1 | 6/2004 | Kenny et al. | 165/80.4 |
| 2004/0107831 A1 | 6/2004 | Graham et al. | 95/96 |
| 2004/0123626 A1 | 7/2004 | Caze et al. | 65/17.2 |
| 2004/0125689 A1 | 7/2004 | Ehrfeld et al. | 366/165.1 |
| 2004/0127352 A1 | 7/2004 | Jin et al. | 502/322 |
| 2004/0130057 A1 | 7/2004 | Mehrabi et al. | 264/171.13 |
| 2004/0131345 A1 | 7/2004 | Kylberg et al. | 392/465 |
| 2004/0131507 A1 | 7/2004 | Saitmacher et al. | 422/111 |
| 2004/0131829 A1 | 7/2004 | Joseph et al. | 428/166 |
| 2004/0132832 A1 | 7/2004 | Espinoza et al. | 518/716 |
| 2004/0136902 A1 | 7/2004 | Plath et al. | 423/651 |
| 2004/0141893 A1 | 7/2004 | Martin | 422/198 |
| 2004/0143059 A1 | 7/2004 | Cabrera | 524/800 |
| 2004/0144421 A1 | 7/2004 | Parce et al. | 137/14 |
| 2004/0156762 A1 | 8/2004 | Schuppich et al. | 422/191 |
| 2007/0017633 A1 | 1/2007 | Tonkovich | 156/300 |
| 2008/0058434 A1 | 3/2008 | Tonkovich et al. | 518/704 |
| 2008/0210596 A1* | 9/2008 | Litt | B01J 19/0093 208/20 |
| 2008/0262112 A1 | 10/2008 | Marion et al. | |
| 2009/0293359 A1 | 12/2009 | Simmons et al. | |
| 2009/0305881 A1 | 12/2009 | Sietsma et al. | 502/259 |
| 2010/0137458 A1* | 6/2010 | Erling | C10G 2/32 518/702 |
| 2010/0184875 A1* | 7/2010 | Bezemer | B01J 8/22 518/712 |
| 2011/0028575 A1 | 2/2011 | Van De Loosdrecht et al. | |
| 2011/0240288 A1 | 10/2011 | Kibby et al. | 166/267 |
| 2014/0045954 A1 | 2/2014 | LeViness et al. | |

FOREIGN PATENT DOCUMENTS

| | | |
|---|---|---|
| DE | 3926466 | 2/1991 |
| DE | 02/064248 | 8/2002 |
| EP | 1 311 341 B1 | 8/2001 |
| EP | 0 904 608 B1 | 12/2001 |

(56) References Cited

FOREIGN PATENT DOCUMENTS

| | | |
|---|---|---|
| EP | 1 362 634 A1 | 11/2003 |
| EP | 1102628 | 11/2006 |
| EP | 1820838 | 8/2007 |
| GB | 1531134 | 11/1978 |
| GB | 2077136 | 12/1981 |
| JP | 2002501430 | 1/2002 |
| JP | 2002126498 | 5/2002 |
| WO | 9421372 | 9/1994 |
| WO | 9700442 | 1/1997 |
| WO | 97/32687 | 9/1997 |
| WO | 9828073 | 7/1998 |
| WO | 9838147 | 9/1998 |
| WO | 98/55812 | 12/1998 |
| WO | 9916542 | 4/1999 |
| WO | 00/06295 | 2/2000 |
| WO | 0006301 | 2/2000 |
| WO | 01/10773 A1 | 2/2001 |
| WO | 01/12312 A2 | 2/2001 |
| WO | 01/12753 A1 | 2/2001 |
| WO | 01/54807 A1 | 8/2001 |
| WO | 01/95237 A2 | 12/2001 |
| WO | 019015 | 12/2001 |
| WO | 02064248 | 8/2002 |
| WO | 03/006149 | 1/2003 |
| WO | 03/026788 | 4/2003 |
| WO | 03/099429 | 4/2003 |
| WO | 03/078052 A1 | 9/2003 |
| WO | 03078052 | 9/2003 |
| WO | 03/106386 A2 | 12/2003 |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062791 | 7/2004 |
| WO | 2004/062792 | 7/2004 |
| WO | 2004/067160 | 8/2004 |
| WO | 2004/067444 | 8/2004 |
| WO | 2004/067492 | 8/2004 |
| WO | 2004/067708 | 8/2004 |
| WO | 2008104793 | 9/2008 |
| WO | 2010056692 | 5/2010 |
| WO | 2010063850 | 6/2010 |
| WO | 2010069925 | 6/2010 |
| WO | 2012107718 | 8/2012 |
| WO | 2013164583 | 11/2013 |
| WO | WO 2013164583 A1 * | 11/2013 ............. B01J 38/10 |
| ZA | 855317 | 7/1985 |

OTHER PUBLICATIONS

Oyvind Borg; "Role of Alumina Support in Cobalt Fischer-Tropsch Synthesis"; Thesis for the degree of doktor ingenior; Norwegian University of Science and Technology; Apr. 2007.

Moodley; "On the Deactivation of Cobalt-based Fischer-Tropsch Synthesis Catalysts"; 2008.

Kraum; "Fischer-Tropsch Syn thesis on Supported Cobalt-Based Catalysts: Influence of Various Preparation Methods and Supports on Catalyst Activity and Chain Growth Probability"; Thesis; Oct. 1999.

International Search Report and Written Opinion, Application No. PCT/US2016/036877, dated Jan. 30, 2017.

International Preliminary Report on Patentability, Application No. PCT/US2013/059142, dated Oct. 21, 2014.

International Search Report and Written Opinion, Application No. PCT/US2013/059142, dated Jan. 7, 2014.

Hinchiranan et al.; "TiO2 promoted Co/SiO2 catalysts for Fischer-Tropsch synthesis"; Fuel Processing Technology, 89(2008).

Deshmukh, et al.; "Enabling cellulosic diesel with microchannel technology"; Future Science; Biofules (2011) 2(3), 315-324.

International Preliminary Report on Patentability for corresponding PCT International Application No. PCT/US2016/036877, dated Dec. 12, 2017.

* cited by examiner

METHOD FOR STOPPING AND RESTARTING A FISCHER-TROPSCH PROCESS

A claim of priority is made herein under 35 U.S.C. § 119(e) to U.S. Provisional Application 62/174,772, filed Jun. 12, 2015 and to U.S. Non-Provisional application Ser. No. 15/178,902, filed Jun. 10, 2016. These applications are incorporated herein by reference.

TECHNICAL FIELD

This invention relates to a synthesis gas conversion process, and more particularly to a method for restarting a synthesis gas conversion process that has stopped.

BACKGROUND

Synthesis gas comprises $H_2$ and CO. Synthesis gas conversion processes include processes for converting synthesis gas in the presence of a synthesis gas conversion catalyst to a synthesis gas conversion product. The synthesis gas conversion product may comprise a methane, methanol, or dimethyl ether. The methane that is formed may be referred to as synthetic natural gas. The synthesis gas conversion process may comprise a Fischer-Tropsch process, and the product may comprise a Fischer-Tropsch product.

SUMMARY

Synthesis gas conversion production runs are typically conducted over extended periods of time. For example, a Fischer-Tropsch production run may be conducted over an extended period of time of, for example, at least about 300 hours up to about 8000 hours or more. In a typical production run the catalyst activity declines over time and is compensated for by increasing the reaction temperature. However, at some point in time the production run will be stopped, either purposely or accidentally, and the problem addressed with this invention relates to providing a rapid restart of the production run with no or minimal loss of catalytic activity. A problem to be solved when stopping and restarting the process relates to avoiding conditions which cause catalyst deactivation when the feed is interrupted and restarted. This can be caused by continued high rates of reaction consuming remaining synthesis gas or hydrogen in the system and exposing the catalyst to undesirable amounts of carbon monoxide or water. Another problem relates to achieving a fast restart to maximize production/operating time on stream. Another problem to be solved relates to the fact that typical solutions to the above-indicated problems tend to be only effective for a limited time duration after the reaction feed is interrupted. As a result, it is often necessary to take action to avoid significant catalyst deactivation. Another problem relates to recovering lost catalyst activity that typically occurs after limited time duration with the short catalyst rejuvenation or regeneration procedures.

This invention provides solutions to these problems. With this invention, a synthesis gas conversion production run (e.g., a Fischer-Tropsch production run) may be restarted and achieve full capacity (i.e., the same or substantially the same catalytic activity or CO conversion rate as prior to the stoppage) within, for example, up to about 48 hours, or up to about 36 hours, or up to about 24 hours, or up to about 12 hours, or up to about 6 hours, or up to about 3 hours, or up to about 2 hours, or up to about 1 hour, or up to about 0.5 hour, or up to about 0.1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour, from the time the flow of synthesis gas into the reactor is restarted. The activity temperature delta for the process may be up to about 5° C., or up to about 3° C., or up to about 1° C., after restart. The relative activity ratio for a process utilizing this invention may be at least about 0.85, or at least about 0.92, or at least about 0.97, or at least about 1.00.

This invention relates to a method for restarting a synthesis gas conversion process, wherein the synthesis gas conversion process comprises flowing synthesis gas into a reactor in contact with a synthesis gas conversion catalyst at a desired reaction temperature and pressure to produce a synthesis gas conversion product and flowing effluent comprising the synthesis gas conversion product out of the reactor, the method comprising: (A) stopping the flow of the synthesis gas into the reactor and the flow of the effluent out of the reactor for a period of time of up to about 48 hours, or up to about 36 hours, or up to about 24 hours, or up to about 12 hours, or up to about 6 hours, or up to about 3 hours, or up to about 1 hour, or up to about 0.5 hour, or up to about 0.1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour; and (B) restarting the flow of synthesis gas into the reactor and the flow of effluent out of the reactor.

This invention relates to a method for restarting a synthesis gas conversion process, wherein the synthesis gas conversion process comprises flowing synthesis gas into a reactor in contact with a synthesis gas conversion catalyst at a desired reaction temperature and pressure to produce a synthesis gas conversion product and flowing effluent comprising the synthesis gas conversion product out of the reactor, the method comprising: (A) stopping the flow of the synthesis gas into the reactor and the flow of the effluent out of the reactor for a period of time of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour; wherein prior to step (A) the pressure within the reactor is at a pre-stoppage pressure and during step (A) the pressure within the reactor is reduced to a level lower than the pre-stoppage pressure; (B) restoring the pressure within the reactor to the pre-stoppage pressure; and (C) restarting the flow of the synthesis gas into the reactor and the flow of effluent out of the reactor.

This invention relates to a method for restarting a synthesis gas conversion process, wherein the synthesis gas conversion process comprises flowing synthesis gas into a reactor in contact with a synthesis gas conversion catalyst at a desired reaction temperature and pressure to produce a synthesis gas product and flowing effluent comprising the synthesis gas conversion product out of the reactor, the method comprising: (A) stopping the flow of the synthesis gas into the reactor and the flow of the effluent out of the reactor for a period of time of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 2 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour; (B) flowing hydrogen into the reactor and restarting the flow of effluent out of the reactor to purge the reactor and to rejuvenate the catalyst; and (C) restarting the flow of synthesis gas into the reactor and the flow of effluent out of the reactor. In an embodiment, the desired reaction temperature is in the range from about 150° C. to about 300° C. and during step (B) the temperature within the reactor is increased to a temperature above the desired reaction temperature. In an embodiment, during step (B) the temperature within the reactor is increased to a temperature of up to about 350° C., or up to about 400° C. In an embodiment, the reactor is cooled during step (B) to a temperature in the range from about 150° C. to about 200° C., or about 170° C. In an embodiment, prior to step (A) the temperature within the reactor is at a pre-stoppage temperature, and subsequent to step (B) the temperature within the reactor is reduced to a level below the pre-stoppage temperature. In an embodiment, prior to step (A) the pressure within the reactor is at a pre-stoppage pressure, and subsequent to step (B) the pressure within the reactor is reduced to a level below the pre-stoppage pressure.

In an embodiment, the temperature of the reactor is controlled with a heat exchange fluid flowing in a heat exchanger in thermal contact with the reactor.

In an embodiment, the purge may be at a flow rate lower than or equal to the synthesis gas feed rate to the reactor prior to stoppage. In an embodiment, the purge may be at a flow rate equal to or higher than the synthesis gas feed rate to the reactor prior to stoppage.

This invention relates to a method for restarting a synthesis gas conversion process, wherein the synthesis gas conversion process comprises flowing synthesis gas into a reactor in contact with a synthesis gas conversion catalyst at a desired reaction temperature and pressure to produce a synthesis gas conversion product and flowing effluent comprising the synthesis gas conversion product out of the reactor, the method comprising: (A) stopping the flow of synthesis gas into the reactor and the flow of effluent out of the reactor for a period of time of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour; (B) flowing natural gas into the reactor and restarting the flow of effluent out of the reactor to purge the reactor; and (C) restarting the flow of synthesis gas into the reactor. In an embodiment, prior to step (A) the temperature within the reactor is at a pre-stoppage temperature, and subsequent to step (B) the temperature within the reactor is reduced to a level below the pre-stoppage temperature. In an embodiment, prior to step (A) the pressure within the reactor is at a pre-stoppage pressure, and subsequent to step (B) the pressure within the reactor is reduced to a level below the pre-stoppage pressure. The natural gas may be a desulfurized natural gas. In an embodiment, the purge may be at a flow rate lower than or equal to the synthesis gas feed rate to the reactor prior to stoppage. In an embodiment, the purge may be at a flow rate equal to or higher than the synthesis gas feed rate to the reactor prior to stoppage.

This invention relates to a method for restarting a synthesis gas conversion process, wherein the synthesis gas conversion process comprises flowing synthesis gas into a reactor in contact with a synthesis gas conversion catalyst at a desired reaction temperature and pressure to produce a synthesis gas product and flowing effluent comprising the synthesis gas conversion product out of the reactor, the method comprising: (A) stopping the flow of synthesis gas into the reactor; (B) flowing hydrogen into the reactor to purge the reactor; and (C) restarting the flow of synthesis gas into the reactor.

This invention relates to a method for restarting a synthesis gas conversion process, wherein the synthesis gas conversion process comprises flowing synthesis gas into a reactor in contact with a synthesis gas conversion catalyst at a desired reaction temperature and pressure to produce a synthesis gas conversion product and flowing effluent comprising the synthesis gas conversion product out of the reactor, the method comprising: (A) stopping the flow of synthesis gas into the reactor; (B) flowing natural gas into the reactor to purge the reactor; and (C) restarting the flow of synthesis gas into the reactor.

This invention relates to a method for restarting a synthesis gas conversion process, wherein the synthesis gas conversion process comprises flowing synthesis gas into a reactor in contact with a synthesis gas conversion catalyst at a desired reaction temperature and pressure to produce a synthesis gas conversion product and flowing effluent comprising the synthesis gas conversion product out of the reactor, the method comprising: (A) stopping the flow of synthesis gas into the reactor and the flow of effluent out of the reactor for a period of time of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour; and (B) restarting the flow of synthesis gas into the reactor and the flow of the effluent out of the reactor, the temperature of the synthesis gas flowing into the reactor being within about 10° C., or about 5° C., or about 2° C., or about 1° C. of the desired reaction temperature. In an embodiment, the temperature of the synthesis gas flowing into the reactor during step (B) is at about the desired reaction temperature. In an embodiment, the desired reaction temperature is controlled with a heat exchange fluid flowing in a heat exchanger in thermal contact with the reactor, the temperature of the heat exchange fluid in the heat exchanger being up to about 10° C., or up to about 5° C., or up to about 2° C., or up to about 1° C. lower than the desired reaction temperature. In an embodiment, the synthesis gas conversion catalyst comprises a wet catalyst.

This invention relates to a method for restarting a Fischer-Tropsch process wherein the Fischer-Tropsch process comprises flowing synthesis gas into a reactor in contact with a Fischer-Tropsch catalyst at a desired reaction temperature and pressure to produce a Fischer-Tropsch product, the method comprising: (A) stopping the flow of synthesis gas into the reactor and the flow of effluent out of the reactor for a period of time of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour; and (B) flowing hydrogen into the reactor in contact with the catalyst at a temperature of up to about 400° C. and restarting the flow of effluent out of the reactor; (C) flowing air into the reactor in contact with the Fischer-Tropsch catalyst at a temperature in the range from about 70° C. to about 350° C., or about 100° C. to about 350° C., or about 150° C. to about 350° C., or about 200° C. to about 350° C., or about 250° C. to about 300° C., for a period of time in the range from about 1 to about 24 hours, or about 1 to about 12 hours; (D) flowing hydrogen into the reactor in contact with the catalyst at a temperature of up to about 400° C. to regenerate the catalyst; and (E) restarting the flow of synthesis gas into the reactor.

This invention relates to a method of restarting a synthesis gas conversion process wherein the process is conducted in a plant comprising a plurality of reaction trains, each reaction train comprising a synthesis gas conversion reactor containing a synthesis gas conversion catalyst, the reaction trains being connected to a reactant feed stream comprising fresh synthesis gas, the method comprising: (A) flowing the reactant feed stream at an overall process flow rate to the plurality of reaction trains in the plant; (B) dividing the reactant feed stream into a plurality of reactant substreams; (C) flowing each reactant substream through a separate reaction train to convert the reactants in the reactant substream to a synthesis gas conversion product; (D) stopping the flow of a reactant substream to one of the reaction trains; and (E) continuing to flow the reactant feed stream to the remainder of reaction trains in the plant to provide a flow rate of fresh synthesis gas to the plant that is the same or substantially the same (i.e., within up to about 15%, or up to about 10%, or up to about 5%, or up to about 2%, or up to about 1%) as the flow rate of fresh synthesis gas in step (A). That is, even though one or more reaction trains may be taken off line, the overall flow rate of fresh synthesis gas to the plant may remain the same or substantially the same. Any decrease in overall capacity may be less than the capacity that has been taken off line during step (D). Thus, in an embodiment, during step (E) the overall process flow rate of fresh synthesis gas to the plant may be the same as the overall process flow rate of fresh synthesis gas used in step (A). In an embodiment, the flow of effluent from the one of the reaction trains is stopped during step (D). In an embodiment, during step (C) a mixture of fresh synthesis gas and a recycled tail gas may flow into the reactor of one or more of the reaction trains. In an embodiment, during step (E) the flow of recycled tail gas into the reactor of the one or more of the remainder of the reaction trains in the plant may be stopped.

This invention relates to a method for restarting a synthesis gas conversion process, wherein the synthesis gas conversion process comprises flowing synthesis gas into a reactor in contact with a synthesis gas conversion catalyst at a desired reaction temperature and pressure to produce a synthesis gas conversion product and flowing effluent comprising the gas conversion product out of the reactor, wherein the reactor contains water vapor, the method comprising: (A) stopping the flow of synthesis gas into the reactor and the flow of effluent out of the reactor; (B) flowing hydrogen into the reactor in contact with the catalyst and/or removing water vapor from the reactor; and (C) restarting the flow of the synthesis gas into the reactor and the flow of the effluent out of the reactor. During step (B) the hydrogen may be selectively introduced into the reactor without purging of the synthesis gas in contact with the catalyst. This may avoid extinction of hydrogen leading to carbon monoxide being present in the absence of hydrogen, leading to carbonaceous deposits on the catalyst and therefore activity loss. During step (C) the water vapor may be selectively removed from the process gas mixture in the reactor. This may avoid the risk of catalyst deactivation from water condensation or sintering in presence of steam. One way of accomplishing removal of water vapor would be to provide a dessicant in a vessel or piping in fluid communication with the reactor at a similar pressure.

This invention relates to a method for restarting a synthesis gas conversion process, wherein the synthesis gas conversion process comprises flowing synthesis gas into a reactor in contact with a synthesis gas conversion catalyst at a desired reaction temperature and pressure to produce a synthesis gas conversion product and flowing effluent comprising the gas conversion product out of the reactor, the method comprising: (A) stopping the flow of synthesis gas into the reactor and the flow of effluent out of the reactor for a period of time of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour; (B) flowing nitrogen gas into the reactor to purge the reactor; and (C) restarting the flow of the synthesis gas into the reactor and the flow of the effluent out of the reactor. In an embodiment, prior to step (A) the temperature within the reactor is at a pre-stoppage temperature, and subsequent to step (B) the temperature is reduced to a level below the pre-stoppage temperature. In an embodiment, prior to step (A) the pressure within the reactor is at a pre-stoppage pressure, and subsequent to step (B) the pressure is reduced to a level below the pre-stoppage pressure.

This invention relates to a method for restarting a Fischer-Tropsch process, wherein the Fischer-Tropsch process comprises flowing synthesis gas into a reactor in contact with a Fischer-Tropsch catalyst at a desired reaction temperature and pressure to produce a Fischer-Tropsch product and flowing effluent comprising the Fischer-Tropsch product out of the reactor, the method comprising: (A) stopping the flow of synthesis gas into the reactor and the flow of effluent out of the reactor for a period of time of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour; (B) rejuvenating the catalyst; and (C) restarting the flow of synthesis gas into the reactor and the flow of the effluent out of the reactor, the temperature of the synthesis gas flowing into the reactor being at the desired reaction temperature, or up to about 30° C., or up to about 20° C., or up to about 10° C., or about 5° C., or about 2° C., or about 1° C. lower than the desired reaction temperature; the temperature within the reactor increasing to the desired reaction temperature within a period of time of up to about 2 hours, or up to about 1 hour, or up to about 0.5 hour, from the time of restarting the flow of synthesis gas into the reactor. In an embodiment, the reaction temperature is controlled with a heat exchange fluid flowing in a heat exchanger in thermal contact with the reactor, the temperature of the heat exchange fluid in the heat exchanger being lower than the desired reaction temperature.

The invention relates to a method for restarting a synthesis gas conversion process, wherein the synthesis gas conversion process comprises flowing synthesis gas into a reactor in contact with a synthesis gas conversion catalyst at a desired reaction temperature and pressure to produce a synthesis gas conversion product and flowing effluent comprising the synthesis gas conversion product out of the reactor, the method comprising: (A) stopping the flow of synthesis gas into the reactor and the flow of effluent out of the reactor for a period of time of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour; (B) flowing hydrogen into the reactor in contact with the catalyst at a temperature of up to about 400° C.; (C) flowing air into the reactor in contact with the catalyst at a temperature in the range from about 70° C. to about 350° C., or about 100° C. to about 350° C., or about 150° C. to about 350° C., or about 200° C. to about 350° C., or about 250° C. to about 300° C., for a period of time in the range from about 1 to about 24 hours, or from about 1 to about 12 hours; (D) flowing hydrogen into the reactor in contact with the catalyst at a temperature of up to about 400° C. to regenerate the catalyst; and (E) restarting the flow of the synthesis gas into the reactor and the flow of the effluent out of the reactor.

This invention relates to a method for restarting a synthesis gas conversion process, wherein the synthesis gas conversion process comprises flowing synthesis gas into a microchannel reactor in contact with a synthesis gas conversion catalyst at a desired reaction temperature and pressure to produce a synthesis gas conversion product and flowing effluent comprising the synthesis gas conversion product out of the reactor, the method comprising: (A) stopping the flow of the synthesis gas into the reactor and the flow of the effluent out of the reactor for up to 48 hours; and (B) restarting the flow of synthesis gas into the reactor and the flow of effluent out of the reactor. In an embodiment, the flow of synthesis gas into the reactor and the flow of effluent out of the reactor is stopped for 0.01 to 48 hours. In an embodiment, prior to step (A) the pressure within the reactor is at a pre-stoppage pressure, and during step (A) the pressure within the reactor is reduced to a level lower than the pre-stoppage pressure, and prior to step (B) the pressure within the reactor is increased to the pre-stoppage pressure. In an embodiment, subsequent to step (A) and prior to step (B) the reactor is purged by flowing hydrogen, natural gas or nitrogen gas in the reactor to purge the reactor. In an embodiment, the synthesis gas conversion process comprises a process for converting synthesis gas to methane, methanol or dimethyl ether. In an embodiment, the synthesis gas conversion process is a Fischer-Tropsch process. In an embodiment, the catalyst comprises cobalt. In an embodiment, the catalyst comprises cobalt on a surface modified support. In an embodiment, the catalyst is in the form of a fixed bed of particulate solids. In an embodiment, the synthesis gas conversion process is a Fischer-Tropsch process and a tail gas is produced in the reactor, at least part of the tail gas being combined with the synthesis gas to form a reactant mixture, the volumetric ratio of the synthesis gas to tail gas being in the range from 1:1 to 10:1. In an embodiment, the synthesis gas conversion process is a Fischer-Tropsch process and the synthesis gas comprising $H_2$ and CO, the mole ratio of $H_2$ to CO being in the range from 1.4:1 to 2.1:1. In an embodiment, the reactor comprises one or more layers of process microchannels and one or more layers of heat exchange channels.

In any of the foregoing embodiments, the synthesis gas comprises CO and prior to stopping the flow of synthesis gas into the reactor the conversion of CO is at a desired conversion value, and after restarting the flow of synthesis gas into the reactor the conversion of CO at the desired conversion value is achieved within a time period of up to about 3 hours, or up to about 2 hours, or up to about 1 hour, or up to about 0.1 hour.

In any of the foregoing embodiment, the catalyst prior to step (A) may be a wet catalyst.

In any of the foregoing embodiments, the reactor may comprise a fixed bed reactor, a fluidized bed reactor or a slurry phase reactor. The reactor may comprise a conventional reactor. The reactor may comprise a microchannel reactor. This invention may be especially valuable for reactor and process designs with small heat transfer temperature differentials (e.g. average temperature differences between the reaction temperature and the heat transfer fluid removing heat from the reactor), for example, less than about 10° C., or less than about 5° C., or less than about 2° C. These ranges for heat transfer temperature differentials may offer advantages in process design (such as enabling coolant wall temperatures to be above the water dew point at low reaction temperatures), but may have a disadvantage in that process interruptions may lead to catalyst deactivation unless the inventive methods disclosed herein are used.

In any of the foregoing embodiments, the synthesis gas conversion process may comprise a process for converting synthesis gas to methane, methanol or dimethyl ether.

In any of the foregoing embodiments, the synthesis gas conversion process may comprise a Fischer-Tropsch process.

In any of the foregoing embodiments, the synthesis gas may comprise CO and $H_2$ and the deactivation rate of the catalyst is less than a loss of about 0.2% CO conversion per day.

In any of the foregoing embodiments, the activity temperature delta for the process after restarting the flow of synthesis gas into the reactor may be up to about 5° C., or up to about 3° C., or up to about 1° C.

In any of the foregoing embodiments, the relative activity ratio for a process utilizing this invention may be at least about 0.85, or at least about 0.92, or at least about 0.97, or at least about 1.00

In any of the foregoing embodiments, prior to the step of restarting the flow of synthesis gas into the reactor the temperature within the reactor may be below the desired reaction temperature, and the temperature of the reactor may be increased to the desired reaction temperature at a rate of up to about 5° C. per hour, or up to about 10° C. per hour, or up to about 15° C. per hour, or up to about 30° C. per hour, or up to about 60° C. per hour.

In any of the foregoing embodiments, the temperature in the reactor may be at a pre-stoppage temperature prior to stopping the flow of synthesis gas into the reactor, and the temperature of the reactor during the step of restarting the flow of synthesis gas into the reactor is at the pre-stoppage temperature.

In any of the foregoing embodiments, the temperature in the reactor may be at a pre-stoppage temperature prior to stopping the flow of synthesis gas into the reactor, and the temperature of the reactor during the step of restarting the flow of synthesis gas into the reactor is below the pre-stoppage temperature, for example, up to about 5° C. below the pre-stoppage temperature, or up to about 10° C. below the pre-stoppage temperature, or up to about 15° C. below the pre-stoppage temperature, or up to about 20° C. below the pre-stoppage temperature.

In any of the foregoing embodiments, prior to stopping the flow of synthesis gas into the reactor, the temperature in the reactor may be at a desired operating temperature, and during the period of time between stopping the flow of synthesis gas into the reactor and restarting the flow of synthesis gas into the reactor the temperature in the reactor may be within about 20° C. of the desired operating temperature.

In any of the foregoing embodiments where a purge is employed, the purge may be at a flow rate lower than or equal to the synthesis gas feed rate to the reactor prior to stopping the flow of synthesis gas into the reactor. In an embodiment, the total volume of purge gas may be lower than or equal to the total volume of synthesis gas between the locations of stoppage of flow of synthesis gas into the reactor and the flow of effluent gas out of the reactor.

In any of the foregoing embodiments where a purge is employed, the purge may be at a flow rate equal to or higher than the synthesis gas feed rate to the reactor prior to stopping the flow of synthesis gas into the reactor. In an embodiment, the total volume of purge gas may be higher than the total volume of synthesis gas between the locations of stoppage of flow of synthesis gas into the reactor and the flow of effluent gas out of the reactor.

The synthesis gas conversion reactor (e.g., Fischer-Tropsch reactor) may comprise a conventional reactor, or a microchannel reactor. The synthesis gas conversion reactor may comprise a fixed bed reactor, a fluidized bed reactor or a slurry phase reactor. In each of the embodiments described above, microchannel reactors are highly advantageous and preferred due to enhanced heat transfer characteristics provided by the microchannel reactors. This is especially true for a Fischer-Tropsch reaction which is highly exothermic, and the microchannel reactor can provide a significantly higher level of heat transfer to control the Fischer-Tropsch reaction when compared to a conventional reactor.

BRIEF DESCRIPTION OF THE DRAWINGS

In the annexed drawings like parts and features have like references. A number of the drawings are schematic illustrations which may not necessarily be drawn to scale.

As illustrated in FIGS. 5-7, the heat exchange channels are oriented to provide for a flow of heat exchange fluid that is cross-current relative to the flow of fluid in the layer of process microchannels. However, the orientation of the heat exchange channels may be altered to provide for a flow of heat exchange fluid that is co-current or counter-current relative to the flow of fluid in the layer of process microchannels.

FIGS. 11-13 are schematic illustrations of fin assemblies that may be used for supporting the catalyst.

DETAILED DESCRIPTION

Figure 1:
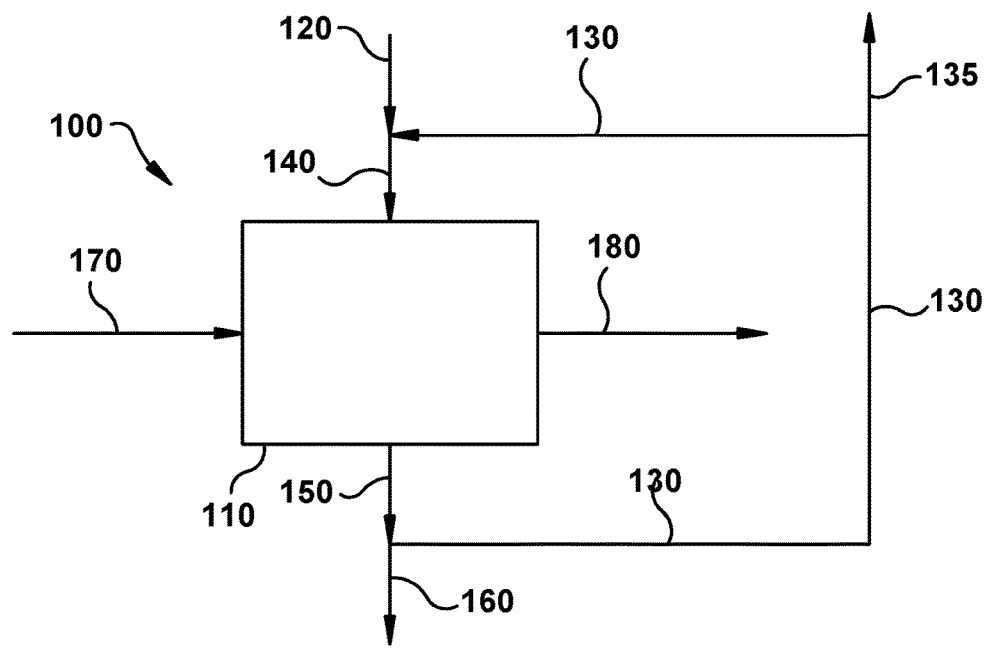
FIG. 1 is a flow sheet illustrating a Fischer-Tropsch reaction process which comprises converting a fresh synthesis gas, which optionally may be combined with a recycled tail gas, to a Fischer-Tropsch product. The reaction process illustrated in FIG. 1 may be referred to as a reaction train.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "microchannel" refers to a channel having at least one internal dimension of height or width of up to about 10 millimeters (mm), or up to about 5 mm, or up to about 2 mm. The microchannel may comprise at least one inlet and at least one outlet wherein the at least one inlet is distinct from the at least one outlet. The length of the microchannel may be at least about two times the height or width, or at least about five times the height or width, or at least about ten times the height or width. The internal height or width of the microchannel may be in the range of up to about 10 mm, or from about 0.05 to about 10 mm, or from about 0.05 to about 8 mm, or from about 0.05 to about 7 mm, or from about 0.05 to about 5 mm, or from about 0.05 to about 3 mm, or from about 0.05 to about 2 mm, or from about 0.05 to about 1.5 mm, or from about 1 to about 10 mm, or from about 1 to about 8 mm, or from about 1 to about 7 mm, or from about 1 to about 5 mm, or from about 1 to about 3 mm, or from about 1 to about 2 mm, or from about 1 to about 1.5 mm. The other internal dimension of height or width may be of any dimension, for example, up to about 5 meters, or about 0.001 to about 5 meters, or about 0.001 to about 3 meters, or about 0.001 to about 2 meters, or about 0.001 to about 1 meter, or about 0.01 to about 0.5 meter, or about 1 to about 10 mm, or about 1 to about 8 mm, or about 1 to about 7 mm, or about 1 to about 5 mm, or about 1 to about 3 mm, or about 1 to about 2 mm. The length of the microchannel may be of any dimension, for example, up to about 5 meters, or from about 0.1 to about 5 meters, or from about 0.1 to about 3 meters, or from about 0.1 to about 2 meters, or from about 0.1 to about 1.5 meters, or from about 0.1 to about 1 meter, or about 0.15 to about 5 meters, or from about 0.15 to about 3 meters, or from about 0.15 to about 2.5 meters, or from about 0.15 to about 2 meters, or from about 0.15 to about 1.5 meters, or from about 0.15 to about 1 meter. The length may be in the range from about 0.1 to about 0.8 meter, or from about 0.1 to about 0.6 meter, or from about 0.1 to about 0.5 meter, or from about 0.1 to about 0.3 meter. The microchannel may have a cross section having any shape, for example, a square, rectangle, circle, triangle, semi-circle, trapezoid, etc. The shape and/or size of the cross section of the microchannel may vary over its length. For example, the height or width may taper from a relatively large dimension (e.g., about 10 mm) to a relatively small dimension (e.g., about 1 mm), or vice versa, over the length of the microchannel.

The term "layer of microchannels" refers to a plurality of microchannels aligned parallel to each other and positioned in a plane. The layer of microchannels may be in the form of a layer of process microchannels or a layer of heat exchange microchannels. The layer of microchannels may comprise a waveform positioned between planar plates. The microchannels may comprise channels formed by the sidewalls of the waveform and planar plates. The space between the planar plates may also have the dimensions of a microchannel (i.e., a height of up to about 10 mm) and therefore may be referred to as a microchannel. A catalyst may be positioned in the process microchannels.

The term "microchannel reactor" refers to an apparatus comprising one or more layers of process microchannels wherein a process is conducted. The process may be a synthesis gas conversion process, for example, a Fischer-Tropsch (FT) reaction process. The microchannel reactor may further comprise a heat exchanger, for example, one or more layers of heat exchange channels adjacent to and/or in thermal contact with the one or more layers of process microchannels. The heat exchange channels may provide cooling for the fluids in the process microchannels. The heat exchange channels may be microchannels. The layers of process microchannels and heat exchange channels may be stacked one above the other or positioned side-by-side to form a microchannel reactor core; see, FIGS. 4 and 5. The microchannel reactor core may have the form of a three-dimensional block which has six faces that may be squares or rectangles. The microchannel reactor core may have the same cross-section along a length. The microchannel reactor core may have the shape of a rectangular or cubic block. The microchannel reactor core may be in the form of a rectangular prism or a cube. The microchannel reactor core may have a length, width and height of any dimension, for example, a length in the range from about 0.1 to about 5 meters, or from about 0.1 to about 3 meters, or from about 0.1 to about 2 meters, or from about 0.1 to about 1.5 meters, or from about 0.1 to about 1 meter, or from about 0.1 to about 0.75 meter, or from about 0.1 to about 0.5 meter, or from about 0.1 to about 0.25 meter, or from about 0.1 to about 5 meter. The microchannel core may have a width in the range from about 0.1 to about 5 meters, or from about 0.1 to about 3 meters, or from about 0.1 to about 2 meters, or from about 0.1 to about 1.5 meters, or from about 0.1 to about 1 meter, or from about 0.1 to about 0.75 meter, or from about 0.1 to about 0.5 meter, or from about 0.1 to about 0.25 meter, or from about 0.1 to about 5 meter. The microchannel reactor core may have a height in the range from about 0.1 to about 5 meters, or from about 0.1 to about 3 meters, or from about 0.1 to about 2 meters, or from about 0.1 to about 1.5 meters, or from about 0.1 to about 1 meter, or from about 0.1 to about 0.75 meter, or from about 0.1 to about 0.5 meter, or from about 0.1 to about 0.25 meter, or from about 0.1 to about 5 meter. The microchannel reactor may include a header for providing for the flow of fluid into the one or more layers of process microchannels, and a footer providing for the flow of fluid out of the one or more layers of process microchannels. The microchannel reactor may include a header for providing for the flow of heat exchange fluid into the heat exchange channels, and a footer providing for the flow of heat exchange fluid out of the one or more layers of heat exchange channels. The microchannel reactor may be sufficiently small and compact so as to be readily transportable. As such, the reactor along with the other equipment used in the synthesis gas conversion process (e.g., the Fischer-Tropsch process) may be readily transported to remote locations, such as military bases, shale oil locations, coal mines, and the like, where the source of synthesis gas may be located. These reactors may be used on ships, oil drilling platforms, and the like.

The term "process microchannel" refers to a microchannel wherein a process is conducted. The process may be a synthesis gas conversion process, for example, a Fischer-Tropsch (FT) reaction process.

The term "conventional reactor" refers to a reactor that is not a microchannel reactor.

The term "reaction train" is used herein to refer to an apparatus with a heat exchange fluid (e.g., a coolant) at a specific controlled temperature, including one or more reactors and feed lines for flowing reactants into the one or more reactors and product or effluent lines for flowing product and/or effluent out of the one or more reactors. The reaction train may be used for conducting a synthesis gas conversion process, for example, a Fischer-Tropsch reaction process.

The term "plant" is used herein to refer to a facility employing one or more reaction trains. When two or more reaction trains are employed, the reaction trains may be connected to a common source of reactants, e.g., synthesis gas.

The term "volume" with respect to volume within a process microchannel may include all volume in the process microchannel a process fluid may flow through or flow by. This volume may include volume within surface features that may be positioned in the process microchannel and adapted for the flow of fluid in a flow-through manner or in a flow-by manner.

The term "adjacent" when referring to the position of one channel relative to the position of another channel may mean directly adjacent such that a wall or walls separate the two channels. In one embodiment, the two channels may have a common wall. The common wall may vary in thickness. However, "adjacent" channels may not be separated by an intervening channel that may interfere with heat transfer between the channels. One channel may be adjacent to another channel over only part of the dimension of the another channel. For example, a process microchannel may be longer than and extend beyond one or more adjacent heat exchange channels.

The term "thermal contact" refers to two bodies, for example, two channels, that may or may not be in physical contact with each other or adjacent to each other but still exchange heat with each other. One body in thermal contact with another body may heat or cool the other body. A layer of process microchannels may be in thermal contact with a layer of heat exchange channels.

The term "fluid" refers to a gas, a liquid, a mixture of a gas and a liquid, or a gas or a liquid containing dispersed solids, liquid droplets and/or gaseous bubbles.

The droplets and/or bubbles may be irregularly or regularly shaped and may be of similar or different sizes.

The term "effluent" is used herein to refer to a process fluid (not a heat exchange fluid) flowing out of a reactor. The effluent may comprise unreacted reactants, diluents, inerts, product, or a mixture of two or more thereof.

The terms "gas" and "vapor" may have the same meaning and are sometimes used interchangeably.

The term "residence time" or "average residence time" refers to the internal volume of a space within a channel occupied by a fluid flowing in the space divided by the average volumetric flow rate for the fluid flowing in the space at the temperature and pressure being used.

The term "activity temperature delta" refers to an increase in the reaction temperature required to maintain the conversion rate of CO in a synthesis gas conversion process (e.g., Fischer-Tropsch reaction process) at a constant level. The reaction temperature may be the temperature of the process fluid (e.g., reactants, product, etc.) as it leaves the catalyst. The activity temperature delta can be calculated as a change in productivity of the catalyst (e.g., volume of CO converted per unit volume of catalyst per hour) at conditions (flows, feed composition and reactor temperature) that existed prior to the upset, i.e., prior to the stop of the flow of synthesis gas into the reactor. The amount of temperature increase needed to compensate for this activity loss would be dependent on the apparent activation energy of the catalyst in the reactor under consideration. For a Fischer-Tropsch catalyst operating under kinetically limited regime with an apparent activation energy of 100 kJ/mol, a 2% loss in activity may result in an equivalent 2% reduction in reaction rates and may necessitate a temperature increase of approximately 1.0° C. to restore the pre-stoppage catalyst productivity under identical operating conditions. In case of change in operating conditions, this may be assessed by use of appropriate rate expression that includes dependence on the partial pressure of the reaction components. An example rate expression for a Fischer-Tropsch catalyst would be "Intrinsic kinetics of the Fischer-Tropsch synthesis on a cobalt catalyst, Ian C. Yates and Charles N. Satterfield, Energy Fuels, 1991, 5 (1), pp 168-173.

The term "relative activity ratio" refers to a ratio of the activity factor post the process restart to that before the process stoppage. The activity factor can be calculated as a ratio of the estimated reaction rate from process data and the predicted reaction rate using an established model that defines the apparent kinetic rate. For example, in the case of Fischer-Tropsch synthesis, the activity factor can be calculated as the ratio of reaction rate estimated as the mols of CO converted per unit volume of catalyst per hour (using synthesis gas flow rate and composition and measured CO conversion) and the model predicted reaction rate (in moles of CO converted per unit volume of the catalyst per hour) calculated by the kinetic rate equation from "Intrinsic Kinetics of the Fischer-Tropsch Synthesis on a Cobalt Catalyst," Ian C. Yates and Charles N. Satterfield, Energy Fuels, 1991, 5 (1), pp 168-173.

The terms "upstream" and "downstream" refer to positions within a channel (e.g., a process microchannel) or in a process flow sheet that is relative to the direction of flow of a fluid in the channel or process flow sheet. For example, a position within a channel or process flow sheet not yet reached by a portion of a fluid stream flowing toward that position would be downstream of that portion of the fluid stream. A position within the channel or process flow sheet already passed by a portion of a fluid stream flowing away from that position would be upstream of that portion of the fluid stream. The terms "upstream" and "downstream" do not necessarily refer to a vertical position since the channels used herein may be oriented horizontally, vertically or at an inclined angle.

The term "plate" refers to a planar or substantially planar sheet of material. The plate may be referred to as a shim. The thickness of the plate may be the smallest dimension of the plate and may be up to about 4 mm, or in the range from about 0.05 to about 4 mm, or in the range from about 0.05 to about 2 mm, or in the range of about 0.05 to about 1 mm, or in the range from about 0.05 to about 0.5 mm. The plate may have any length and width.

The term "surface feature" refers to a depression in a channel wall and/or a projection from a channel wall that disrupts flow within the channel. The surface features may be in the form of circles, spheres, frustrums, oblongs, squares, rectangles, angled rectangles, checks, chevrons, vanes, airfoils, wavy shapes, and the like, and combinations of two or more thereof. The surface features may contain subfeatures where the major walls of the surface features further contain smaller surface features that may take the form of notches, waves, indents, holes, burrs, checks, scallops, and the like. The surface features may have a depth, a width, and for non-circular surface features a length. The surface features may be formed on or in one or more of the interior walls of the process microchannels used in accordance with the disclosed process. The surface features may be referred to as passive surface features or passive mixing features. The surface features may be used to disrupt flow (for example, disrupt laminar flow streamlines) and create advective flow at an angle to the bulk flow direction.

The term "heat exchange channel" refers to a channel having a heat exchange fluid in it that provides heat and/or absorbs heat. The heat exchange channel may absorb heat from or provide heat to an adjacent channel (e.g., process microchannel) and/or one or more channels in thermal contact with the heat exchange channel. The heat exchange channel may absorb heat from or provide heat to channels that are adjacent to each other but not adjacent to the heat exchange channel. In one embodiment, one, two, three or more channels may be adjacent to each other and positioned between two heat exchange channels. The heat exchange channel may be a cooling channel.

The term "heat transfer wall" refers to a common wall between a layer of process microchannels and an adjacent layer of heat exchange channels where heat transfers from one channel layer to the other through the common wall.

The term "heat exchange fluid" refers to a fluid that may give off heat to and/or absorb heat from the surrounding walls of a heat exchange channel via conduction, convection or phase change (e.g., giving off heat while transforming from vapor to liquid or absorbing heat while transforming from liquid to vapor). The heat exchange fluid may be in or flow in a heat exchange channel or a layer of heat exchange channels. The term "heat exchange fluid" may be used interchangeably with the word "coolant."

The term "waveform" refers to a contiguous piece of sheet material that is transformed from a planar object to a three-dimensional object. The waveform may be used to form one or more microchannels. The waveform may comprise a right angled corrugated sheet which may be sandwiched between opposed planar plates. The right angled corrugated sheet may have rounded edges. The waveform may have a sinusoidal shape; see, FIGS. 5 and 6. One or more microchannels in a microchannel layer may be defined on three sides by the waveform and on the fourth side by one of the planar plates. The waveform may be made of any of the materials disclosed herein as being useful for making the microchannel reactor. These may include copper, aluminum, stainless steel, and the like. These may also include overlay, inlaid, or edge clad materials which combine two alloys (for example by cold rolling) to produce a clad material with properties which are different than either alloy alone. The thermal conductivity of the waveform may be about 1 W/m-K or higher.

The term "bulk flow direction" refers to the vector through which fluid may travel in an open path in a channel.

The term "bulk flow region" refers to open areas within a microchannel. A contiguous bulk flow region may allow rapid fluid flow through a microchannel without significant pressure drops. In one embodiment, the flow in the bulk flow region may be laminar. A bulk flow region may comprise at least about 5% of the internal volume and/or cross-sectional area of a microchannel, or from about 5% to about 100%, or from about 5% to about 99%, or from about 5% to about 95%, or from about 5% to about 90%, or from about 30% to about 80% of the internal volume and/or cross-sectional area of the microchannel.

The terms "open channel" or "flow-by channel" or "open path" refers to a channel (e.g., a microchannel) with a gap with a height of at least about 0.01 mm that extends through the channel such that fluid may flow through the channel without encountering a barrier to flow. The gap may have a height of up to about 10 mm, or up to about 5 mm, or up to about 2 mm, or up to about 1 mm, or up to about 0.5 mm.

The term "cross-sectional area" of a channel (e.g., process microchannel) refers to an area measured perpendicular to the direction of the bulk flow of fluid in the channel and may include all areas within the channel including any surface features that may be present, but does not include the channel walls. For channels that curve along their length, the cross-sectional area may be measured perpendicular to the direction of bulk flow at a selected point along a line that parallels the length and is at the center (by area) of the channel. Dimensions of height and width may be measured from one channel wall to the opposite channel wall. These dimensions may not be changed by application of a coating to the surface of the wall. These dimensions may be average values that account for variations caused by surface features, surface roughness, and the like.

The term "open cross-sectional area" of a channel (e.g., process microchannel) refers to an area open for bulk fluid flow in a channel measured perpendicular to the direction of the bulk flow of fluid flow in the channel. The open cross-sectional area may not include internal obstructions such as surface features and the like which may be present.

The term "superficial velocity" for the velocity of a fluid flowing in a channel refers to the velocity resulting from dividing the volumetric flow rate of the fluid at the inlet temperature and pressure of the channel by the cross-sectional area of the channel.

The term "free stream velocity" refers to the velocity of a stream flowing in a channel at a sufficient distance from the sidewall of the channel such that the velocity is at a maximum value. The velocity of a stream flowing in a channel is zero at the sidewall if a no slip boundary condition is applicable, but increases as the distance from the sidewall increases until a constant value is achieved. This constant value is the "free stream velocity."

The term "bottled" is used herein to refer to a process shut down procedure wherein the flow of reactants into a reactor and the flow of effluent out of the reactor are stopped. The term "isolated" may be used in place of "bottled." The net effect is the isolation of a process fluid (e.g. synthesis gas) in the reactor in contact with the catalyst.

The term "process fluid" is used herein to refer to reactants, product and any diluent or other fluid that may flow in a process microchannel.

The term "reaction zone" refers to the space within a microchannel wherein a chemical reaction occurs or wherein a chemical conversion of at least one species occurs. The reaction zone may contain one or more catalysts.

The term "contact time" refers to the volume of a reaction zone within a microchannel divided by the volumetric feed flow rate of the reactants at a temperature of 0° C. and a pressure of one atmosphere.

The term "fresh synthesis gas" refers to synthesis gas that flows into a microchannel reactor and is used as a reactant in a synthesis gas conversion process (e.g., a Fischer-Tropsch reaction). Synthesis gas comprises a mixture of CO and $H_2$. Synthesis gas may be referred to as syngas. Fresh synthesis gas is not a FT tail gas.

The term "tail gas" refers to a gaseous product produced during a synthesis gas conversion process. For example, the tail gas may be a "FT tail gas" which is a tail gas produced during a Fisher-Tropsch reaction. The tail gas may contain CO and $H_2$. The tail gas may be combined with fresh synthesis gas to form a reactant mixture.

The term "reactant mixture" refers to a mixture of fresh synthesis gas and tail gas recycled from a synthesis gas conversion process (e.g., a Fischer-Tropsch reaction).

The term "conversion of CO" refers to the CO mole change between the fresh synthesis gas in a reactant feed stream and the effluent gas leaving the reactor, divided by the moles of CO in the fresh synthesis gas in the reactant feed stream.

The term "one-pass conversion of CO" refers to the conversion of CO from the overall reactant mixtures (i.e., fresh synthesis gas plus recycled tail gas or recycled tail gas components) after one pass through the microchannel reactor.

The term "selectivity to methane" refers to the moles of methane in a product minus the moles of methane in a reactant, divided by the moles of CO in the reactant that are consumed in the reaction.

The term "yield" refers to the number of moles of product exiting a reactor divided by the number of moles of a reactant entering the reactor.

The term "cycle" refers to a single pass of the reactants through a reactor.

The term "wet catalyst" refers to a catalyst (e.g., a catalyst bed of particulate solids) which has produced liquid product, for example Fischer-Tropsch liquid hydrocarbon product, and has a liquid film on its surface and/or in its pores that may increase the diffusional resistance for gas phase reactants to reach active catalyst sites, slowing down the apparent reaction rate relative to that for a catalyst not containing such a film. Use of the term "wax" to describe a Fischer-Tropsch product implies that the material is a liquid while in the reactor at the reaction conditions of temperature and pressure.

The term "graded catalyst" refers to a catalyst with one or more gradients of catalytic activity. The graded catalyst may have a varying concentration or surface area of a catalytically active metal. The graded catalyst may have a varying turnover rate of catalytically active sites. The graded catalyst may have physical properties and/or a form that varies as a function of distance. For example, the graded catalyst may have an active metal concentration that is relatively low at the entrance to a process microchannel and increases to a higher concentration near the exit of the process microchannel, or vice versa; or a lower concentration of catalytically active metal nearer the center (i.e., midpoint) of a process microchannel and a higher concentration nearer a process microchannel wall, or vice versa, etc. The thermal conductivity of a graded catalyst may vary from one location to another within a process microchannel. The surface area of a graded catalyst may be varied by varying size of catalytically active metal sites on a constant surface area support, or by varying the surface area of the support such as by varying support type or particle size. A graded catalyst may have a porous support where the surface area to volume ratio of the support is higher or lower in different parts of the process microchannel followed by the application of the same catalyst coating everywhere. A combination of two or more of the preceding embodiments may be used. The graded catalyst may have a single catalytic component or multiple catalytic components (for example, a bimetallic or trimetallic catalyst). The graded catalyst may change its properties and/or composition gradually as a function of distance from one location to another within a process microchannel. The graded catalyst may comprise rimmed particles that have "eggshell" distributions of catalytically active metal within each particle. The graded catalyst may be graded in the axial direction along the length of a process microchannel or in the lateral direction. The graded catalyst may have different catalyst compositions, different loadings and/or numbers of active catalytic sites that may vary from one position to another position within a process microchannel. The number of catalytically active sites may be changed by altering the porosity of the catalyst structure. This may be accomplished using a washcoating process that deposits varying amounts of catalytic material. An example may be the use of different porous catalyst thicknesses along the process microchannel length, whereby a thicker porous structure may be left where more activity is required. A change in porosity for a fixed or variable porous catalyst thickness may also be used. A first pore size may be used adjacent to an open area or gap for flow and at least one second pore size may be used adjacent to the process microchannel wall.

The term "Fischer-Tropsch" or "FT" refers to a chemical reaction represented by the equation:

$$n\ CO + 2n\ H_2 \rightarrow (CH_2)_n + n\ H_2O$$

This reaction is an exothermic reaction. n may be any number, for example from 1 to about 1000, or from about 2 to about 200, or from about 5 to about 150.

The term "synthesis gas conversion product" refers to a product formed by a synthesis gas conversion process. The product may comprise methane, methanol and/or dimethyl ether. The synthesis gas conversion product may be a Fischer-Tropsch product.

The term "Fischer-Tropsch product" or "FT product" refers to a hydrocarbon product made by a Fischer-Tropsch process. The FT product may comprise a liquid, solid, gas, or mixture of two or more thereof. The FT solid product may be in the form of a wax, i.e., a Fischer-Tropsch wax or FT wax. The FT wax may be melted or hydrocracked to form a FT liquid. The FT liquid product may have a boiling point at or above about 30° C. at atmospheric pressure. The FT gas may be referred to as a FT tail gas. The "FT tail gas" may have a boiling point below about 30° C. at atmospheric pressure. The FT tail gas may contain $H_2$ and CO.

The term "dry" catalyst refers to a fresh catalyst or a regenerated catalyst that has not been exposed to a synthesis gas conversion process and does not have a liquid and/or solid synthesis gas conversion product adhered to its surface or in its pores.

The term "rejuvenate a catalyst" refers to a process for removing process liquid and/or solids (e.g., FT liquid and/or FT wax) from the surface of a catalyst and/or the pores of the catalyst. The catalyst may be rejuvenated using hydrogen or a solvent. The solvent may be a liquid hydrocarbon solvent.

The term "regenerate a catalyst" refers to a process wherein process liquid and/or solids (e.g., FT liquid and/or FT wax) are removed from the surface of a catalyst and/or the pores of the catalyst, and then the catalyst is subjected to oxidation and reduction. Alternatively, the catalyst may be regenerated using hydrogen.

The term "desulfurized natural gas" refers to a natural gas that has been processed in a desulfurization step. The desulfurized natural gas may have a sulfur content of up to about 100 parts per billion by volume (ppbv), or up to about 50 ppbv, or up to about 30 ppbv, or up to about 10 ppbv, or up to about 5 ppbv.

The term "chain growth" refers to the growth in a molecule resulting from a reaction in which the molecule grows with the addition of new molecular structures (e.g., the addition of methylene groups to a hydrocarbon chain in a Fischer-Tropsch synthesis).

The term "aliphatic hydrocarbon" refers to aliphatic compounds, such as alkanes, alkenes, alkynes, and the like.

The term "higher molecular weight aliphatic hydrocarbon" refers to an aliphatic hydrocarbon having 2 or more carbon atoms, or 3 or more carbon atoms, or 4 or more carbon atoms, or 5 or more carbon atoms, or 6 or more carbon atoms. The higher molecular weight aliphatic hydrocarbons may have up to about 200 carbon atoms or higher, or up to about 150 carbon atoms, or up to about 100 carbon atoms, or up to about 90 carbon atoms, or up to about 80 carbon atoms, or up to about 70 carbon atoms, or up to about 60 carbon atoms, or up to about 50 carbon atoms, or up to about 40 carbon atoms, or up to about 30 carbon atoms. Examples may include ethane, propane, butane, pentane, hexane, octane, decane, dodecane, and the like.

The term "Co loading" refers to the weight of Co in a catalyst divided by the total weight of the catalyst, that is, the total weight of the Co plus any co-catalyst or promoter as well as any support. If the catalyst is in the form of particulate solids which include a support material (e.g., $Al_2O_3$), the weight of the support material is included in the calculation. If the catalyst is supported on an engineered support structure, such as a foam, felt, wad or fin, the weight of such engineered support structure is not included in the calculation. Similarly, if the catalyst is adhered to a channel wall, the weight of the channel wall is not to be included in the calculation.

The term "mm" may refer to millimeter. The term "nm" may refer to nanometer. The term "ms" may refer to millisecond. The term "μs" may refer to microsecond. The term "μm" may refer to micron or micrometer. The terms "micron" and "micrometer" have the same meaning and may be used interchangeably.

Unless otherwise indicated, all pressures are expressed in terms of absolute pressure.

The synthesis gas conversion process (e.g., Fischer-Tropsch process) employed herein may use fresh synthesis gas as a synthesis gas conversion reactant (e.g., Fischer-Tropsch reactant). Optionally, a FT tail gas may be used in combination with the fresh synthesis gas to form a reactant mixture. The fresh synthesis gas may be produced using steam reforming (e.g., a steam methane reforming (SMR) reaction where methane is reacted with steam in the presence of a steam methane reforming (SMR) catalyst); partial oxidation; autothermal reforming; carbon dioxide reforming; or a combination of two or more thereof.

The fresh synthesis gas may be produced by gasifying a carbonaceous material at an elevated temperature, for example, about 700° C. or higher. The carbonaceous material may comprise any carbon-containing material that can be gasified to produce synthesis gas. The carbonaceous material may comprise natural gas, biomass (e.g., plant or animal matter, biodegradable waste, and the like), a food resource (e.g., as corn, soybean, and the like), and/or a non-food resource such as coal (e.g., low grade coal, high grade coal, clean coal, and the like), oil (e.g., crude oil, heavy oil, tar sand oil, shale oil, and the like), solid waste (e.g., municipal solid waste, hazardous waste), refuse derived fuel (RDF), tires, petroleum coke, trash, garbage, biogas, sewage sludge, animal waste, agricultural waste (e.g., corn stover, switch grass, grass clippings), construction demolition materials, plastic materials (e.g., plastic waste), cotton gin waste, landfill gas, a mixture of two or more thereof, and the like.

The fresh synthesis gas may contain water and/or particulate solids which may be separated from the fresh synthesis gas before flowing the fresh synthesis gas into a synthesis gas conversion reactor (e.g., a Fischer-Tropsch reactor). If the synthesis gas conversion reactor is a microchannel reactor, the presence of such solids and/or water in the fresh synthesis gas may be detrimental to the operation of the microchannel reactor due to the fact that the passages in the microchannel reactor are very small (e.g., a process microchannel has an internal height or width of up to only about 10 mm). The removal of (or significant reduction in the concentration) of such water and/or particulate solids may avoid or reduce the likelihood of a reduction in the reaction rate of the synthesis gas conversion process (e.g., Fischer-Tropsch process), as well as avoid clogging in the process microchannels. It can also avoid premature catalyst deactivation. This is significant due to the fact that the process microchannels of a microchannel reactor use less catalyst than a conventional (i.e., non-microchannel) reactor.

The fresh synthesis gas may comprise $H_2$ and CO with the molar ratio of $H_2$ to CO in the range from about 1.9:1 to about 2.1:1, or from about 1.95:1 to about 2.05:1, or from about 1.98:1 to about 2.02:1.

The fresh synthesis gas may optionally be combined with a recycled tail gas (e.g., a recycled FT tail gas), which also contains $H_2$ and CO, to form a reactant mixture. The tail gas may comprise $H_2$ and CO with a molar ratio of $H_2$ to CO in the range from about 0.5:1 to about 2:1, or from about 0.6:1 to about 1.8:1, or from about 0.7:1 to about 1.2:1.

The reactant mixture may comprise $H_2$ and CO with a molar ratio of $H_2$ to CO that may be in the range from about 1.4:1 to about 2.1:1, or from about 1.5:1 to about 2:1:1, or from about 1.6:1 to about 2:1, or from about 1.7:1 to about 1.9:1.

When the recycled tail gas is used, the volumetric ratio of fresh synthesis gas to recycled tail gas used to form the reactant mixture may be in the range from about 1:1 to about 10:1, or from about 1:1 to about 8:1, or from about 1:1 to about 6:1, or from about 1:1 to about 4:1, or from about 3:2 to about 7:3, or about 2:1.

The reactor may be a conventional reactor or a microchannel reactor. In an embodiment, the reactor may be characterized by a heat transfer surface (or heat transfer wall) for removing heat of reaction from the reactor (or process microchannel layer) wherein the ratio of the surface area of the heat transfer surface to the volume of the catalyst in the reactor is at least about 300 square meters ($m^2$) of heat transfer surface per cubic meter ($m^3$) of catalyst, or from about 300 to about 5000 $m^2/m^3$; or from about 1000 to about 3000 $m^2/m^3$.

In the following discussion relating to the embodiments illustrated in FIGS. 1 and 2, the synthesis gas conversion process will be discussed in terms of being a Fischer-Tropsch reaction process. However, alternatively the synthesis gas conversion process illustrated in FIGS. 1 and 2 may be a process for converting synthesis gas to methane, methanol or dimethyl ether, and the discussion provided below is applicable to such processes.

Referring to FIG. 1, the Fischer-Tropsch process 100 employs the use of Fischer-Tropsch reactor 110. The Fischer-Tropsch reactor 110 may be a conventional reactor or a microchannel reactor, although a microchannel reactor is preferred. The Fischer-Tropsch reactor may be a fixed bed reactor, a fluidized bed reactor, or a slurry phase reactor. When a microchannel reactor is used it may be referred to as a Fischer-Tropsch or FT microchannel reactor. In operation, fresh synthesis gas 120 flows into the Fischer-Tropsch reactor 110. Optionally, the fresh synthesis gas may be combined with recycled tail gas 130 to form reactant mixture 140 which flows into the Fischer-Tropsch reactor 110. The fresh synthesis gas may be combined with the recycled tail gas upstream of the Fischer-Tropsch reactor 110, as shown in FIG. 1, or in the Fischer-Tropsch reactor 110.

In an embodiment, referring to FIG. 1, the flow of synthesis gas into the reactor 110 may be stopped, and the Fischer-Tropsch process may be restarted by a method comprising: restoring the pressure within the reactor 110 at the reaction pressure, maintaining the temperature within the reactor at the desired reaction temperature, and restarting the flow of synthesis gas into the reactor.

In an embodiment, the flow of synthesis gas into the reactor 110 is stopped, and the Fischer-Tropsch process is restarted by a method comprising: restoring the pressure within the reactor at the reactor reaction pressure, and restarting the flow of synthesis gas into the reactor. The reactor temperature may then ramped up to the operating temperature that was employed prior to the stop within a period of up to about 36 hours, or up to about 24 hours, or up to about 12 hours, or up to about 6 hours, or up to about 3 hours, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 1 hour, or from about 0.1 to about 0.5 hour by heating at a rate of up to about 5° C. per hour, or up to about 10° C. per hour, or up to about 15° C. per hour, or up to about 30° C. per hour, or up to about 60° C. per hour. The reaction temperature may be controlled with a coolant flowing in a heat exchanger in thermal contact with the reactor.

In an embodiment, the flow of synthesis gas into the reactor 110 is stopped, and the Fischer-Tropsch process may be restarted by a method comprising: flowing hydrogen into the reactor to purge the reactor of reactants and effluent, holding the reactor in a hydrogen environment for a period of time of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour; and restarting the flow of synthesis gas into the reactor. The purge may be at a flow rate lower than or equal to or greater than the synthesis gas feed rate to the reactor prior to stoppage. The reaction temperature may be in the range from about 150° C. to about 300° C., and during the step of flowing hydrogen into the reactor the temperature within the reactor may increase to a temperature above the reaction temperature, for example, up to about 350° C., or up to about 400° C. The reaction temperature may be controlled with a coolant flowing in a heat exchanger in thermal contact with the reactor.

In an embodiment, the flow of synthesis gas into the reactor 110 is stopped, and the Fischer-Tropsch process may be restarted by a method comprising: flowing desulfurized natural gas into the reactor to purge the reactor of reactants and effluent, holding the reactor in a natural gas environment at a temperature in the range of about 150 to about 300° C. for a period of time of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour; and then restarting the flow of synthesis gas into the reactor and the flow of effluent out of the reactor. The purge may be at a flow rate lower than or equal to or greater than the synthesis gas feed rate to the reactor prior to stoppage.

In an embodiment, the flow of synthesis gas into the reactor 110 is stopped, and the Fischer-Tropsch process may be restarted by a method comprising: maintaining the reactor at the pre-stop operating temperature for a period of up to about 12 hours, or up to about 6 hours, or up to about 3 hours, or up to about 1 hour, then flowing hydrogen, nitrogen, or desulfurized natural gas into the reactor to purge the reactor of reactants and effluent, holding the reactor in a purge gas environment for a period of time of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 3 hours, or from about 0.1 to about 1 hour, or from about 0.1 to about 0.5 hour at a temperature in the range of about 150 to about 300° C., or about 200° C. to about 250° C., and then restarting the flow of synthesis gas into the reactor. The purge may be at a flow rate lower than or equal to or greater than the synthesis gas feed rate to the reactor prior to stoppage.

In an embodiment, the flow of synthesis gas into the reactor 110 is stopped, and the Fischer-Tropsch process may be restarted by a method comprising: maintaining the reactor at the pre-stop operating temperature for a period of time of up to about 48 hours, or up to about 36 hours, or up to about 24 hours, or up to about 36 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 2 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour, then flowing hydrogen, nitrogen or desulfurized natural gas into the reactor to purge the reactor of reactants and Fischer-Tropsch product, holding the reactor in a purge gas environment for a period of time of up to about 48 hours, or up to about 36 hours, or up to about 24 hours, or up to about 12 hours, or up to about 6 hours, or up to about 3 hours, or up to about 1 hour, cooling the reactor to a temperature lower than the operating temperature (e.g., in the range of about 25 to about 150° C.); and then restarting the flow of synthesis gas into the reactor. The purge may be at a flow rate lower than or equal to or greater than the synthesis gas feed rate to the reactor prior to stoppage. The reactor temperature may then be ramped up to the operating temperature that was used prior to the stop within a short period of time by heating at a rate of up to about 5° C. per hour, or up to about 10° C. per hour, or up to about 15° C. per hour, or up to about 30° C. per hour, or up to about 60° C. per hour.

In an embodiment, the flow of synthesis gas into the reactor 110 is stopped, and the Fischer-Tropsch process may be restarted by a method comprising: maintaining the reactor at the pre-stop operating temperature and pressure for a period of up to about 48 hours, or up to about 36 hours, or up to about 24 hours, or up to about 12 hours, or up to about 6 hours, or up to about 3 hours, or up to about 1 hour, or from about 0.01 to about 48 hours, or from about 0.01 to about 36 hours, or from about 0.01 to about 24 hours, or from about 0.01 to about 12 hours, or from about 0.01 to about 6 hours, or from about 0.01 to about 3 hours, or from about 0.01 to about 1 hour, or from about 0.01 to about 0.5 hour, or from about 0.1 to about 48 hours, or from about 0.1 to about 36 hours, or from about 0.1 to about 24 hours, or from about 0.1 to about 12 hours, or from about 0.1 to about 6 hours, or from about 0.1 to about 3 hours, or from about 0.1 to about 2 hours, or from about 0.1 to about 1 hour, or from about 0.1 to about 0.5 hour then depressurizing the reactor to a pressure (lower than the operating pressure) of up to about 20 atmospheres, or up to about 10 atmospheres, or up to about 5 atmospheres, and then flowing hydrogen, nitrogen, or desulfurized natural gas into the reactor to purge the reactor of reactants and effluent, holding the catalyst reactor in a purge gas environment for a period of time of up to about 48 hours, or up to about 36 hours, up to about 24 hours, or up to about 12 hours, or up to about 6 hours, or up to about 3 hours, or up to about 1 hour at a temperature in the range from about 25° C. to about 300° C., or about 150° C. to about 250° C.; and then restarting the flow of synthesis gas into the reactor and pressurizing the reactor to the target operating pressure. The purge may be at a flow rate lower than or equal to or greater than the synthesis gas feed rate to the reactor prior to stoppage. If the reactor temperature is reduced to below the pre-stop operating temperature, the reactor temperature may then be ramped up to the operating temperature prior to the stop within a short time by heating at a rate as high of up to about 5° C. per hour, or up to about 10° C. per hour, or up to about 15° C. per hour, or up to about 30° C. per hour, or up to about 60° C. per hour.

In an embodiment, the flow of synthesis gas into the reactor 110 is stopped, and the Fischer-Tropsch process is restarted by a method comprising: restarting the flow of synthesis gas into the reactor, the temperature of the synthesis gas flowing into the reactor being less than up to about 10° C. of the desired reaction temperature in the reactor, or less than up to about 5° C. of the desired reaction temperature. The reaction temperature may be controlled with a coolant flowing in a heat exchanger in thermal contact with the reactor, and during the step of restarting the flow of synthesis gas into the reactor, the temperature of the coolant in the heat exchanger may be less than up to about 10° C., or less than up to about 5° C., of the reaction temperature in the reactor. In this embodiment, the Fischer-Tropsch catalyst may comprise a wet catalyst.

In an embodiment, the flow of synthesis gas into the reactor 110 is stopped, and the Fischer-Tropsch process is restarted by a method comprising: rejuvenating or regenerating the catalyst; and restarting the flow of synthesis gas into the reactor, the temperature of the synthesis gas flowing into the reactor being at the desired reaction temperature. The reaction temperature in the reactor may be controlled with a heat exchange fluid flowing in a heat exchanger in thermal contact with the reactor, and during the restarting of the flow of synthesis gas into the reactor and the flow of effluent out of the reactor, the temperature of the heat exchange fluid in the heat exchanger may be lower than the reaction temperature in the reactor, for example, up to about 10° C. lower, or up to about 5° C. lower, than the reaction temperature in the reactor.

In an embodiment, the flow of synthesis gas into and the flow of effluent out of the reactor 110 is stopped, and the catalyst is a wet catalyst containing a wax. The Fischer-Tropsch process may be restarted by a method comprising: rejuvenating the catalyst by flowing hydrogen in contact with the catalyst at a temperature of up to about 400° C. and then restarting the flow of synthesis gas into the reactor. The reaction temperature in the reactor may be controlled with a heat exchange fluid in thermal contact with the reactor, and during the restarting of the flow of synthesis gas into the reactor and the flow of effluent out of the reactor, the temperature of the heat exchange fluid may be lower than the reaction temperature in the reactor, for example, up to about 10° C. lower, or up to about 5° C. lower, than the reaction temperature in the reactor.

In an embodiment, the flow of synthesis gas into and the flow of effluent out of the reactor 110 is stopped, and the catalyst is a wet catalyst containing a wax. The Fischer-Tropsch process may be restarted by a method comprising: regenerating the catalysts by removing wax from the catalyst by flowing hydrogen in contact with the catalyst at a temperature of up to about 350° C., or up to about 400° C., or up to about 450° C. This may be followed by oxidizing the catalyst in air (21% $O_2$) flowing air into the reactor in contact with the catalyst at a temperature in the range of up to about 200° C., or up to about 300° C., or up to about 350° C., for a period of time in the range from about 1 to about 12 hours, or even with no hold time at the maximum temperature. This may be followed by another reduction step where hydrogen flows in contact with the catalyst at a temperature up to about 400° C., or up to about 350° C. The reactor is then cooled to the desired reaction temperature. The flow of synthesis gas into the reactor in contact with the catalyst may then be commenced. The reaction temperature in the reactor may be controlled with a heat exchange fluid in thermal contact with the reactor, and during the restarting of the flow of synthesis gas into the reactor, the temperature of the heat exchange fluid may be lower than the reaction temperature in the reactor, for example, up to about 10° C. lower, or up to about 5° C. lower, than the reaction temperature in the reactor.

Figure 2:
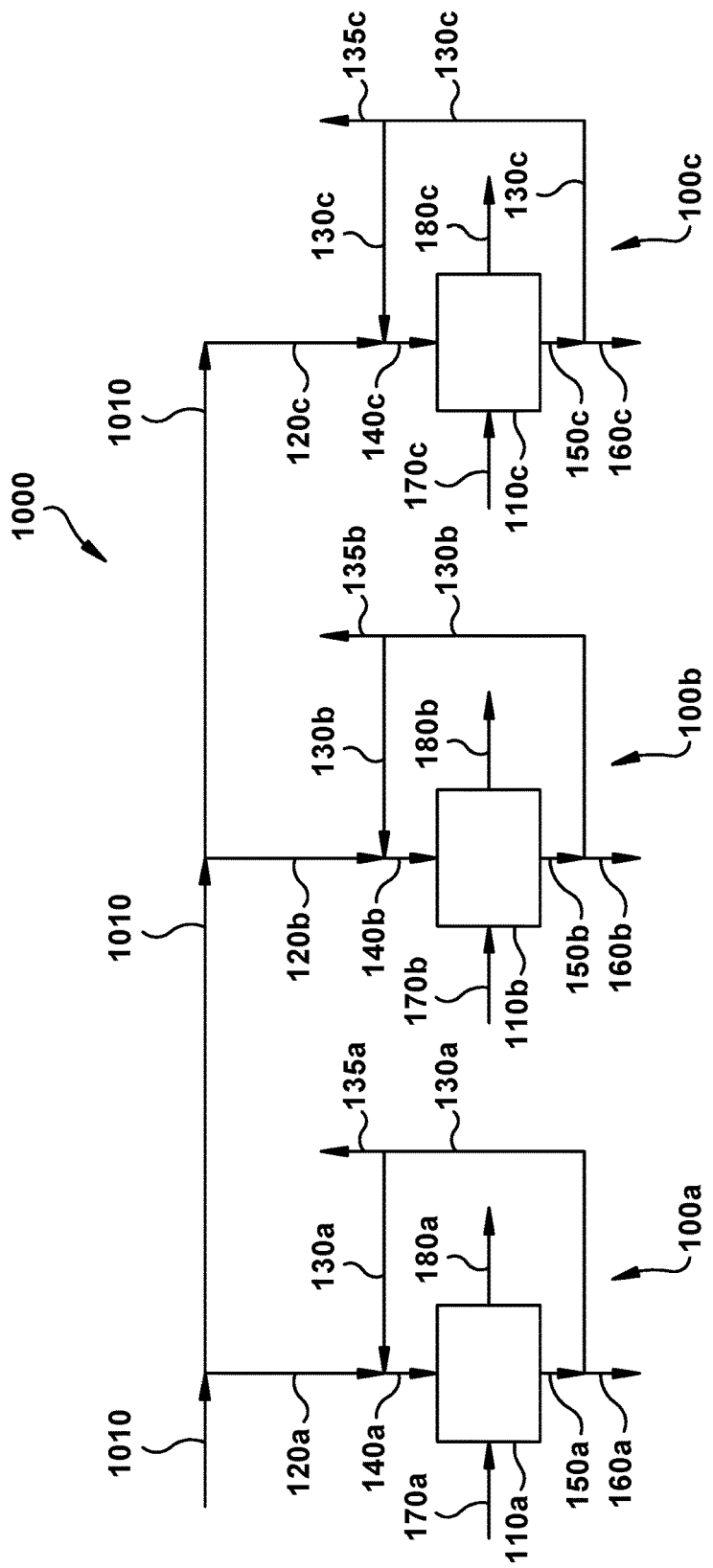
FIG. 2 is a flow sheet illustrating a Fischer-Tropsch reaction process which comprises conducting the Fischer-Tropsch reaction in a plurality of reaction trains (three reaction trains being shown in the drawing) connected to a common synthesis gas feedstream.

Referring to FIG. 2, the synthesis gas conversion (e.g., Fischer-Tropsch process) may be conducted in a plant 1000 comprising a plurality of reaction trains 100a, 100b and 100c. Each reaction train 100a, 100b and 100c comprises a Fischer-Tropsch reactor 110a, 110b, 110c, respectively, containing a Fischer-Tropsch catalyst. The reaction trains 100a, 100b and 100c may be connected to a common reactant feed stream 1010 comprising fresh synthesis gas. The flow of synthesis gas into the Fischer-Tropsch reactor of one or more of the reaction trains (100a, 100b, 100c) in the plant 1000 may be stopped, while the flow of synthesis gas into and the flow of effluent out of the remainder of the reaction trains (100a, 100b, 100c) in the plant 1000 is continued. The method may comprise: (A) flowing the reactant feed stream 1010 at an overall desired process flow rate to the plurality of reaction trains (100a, 100b, 100c) in the plant 1000; (B) dividing the reactant feed stream into a plurality of reactant substreams (120a, 120b, 120c); (C) flowing each reactant substream through a separate reaction train to convert the reactants in the reactant substream to a Fischer-Tropsch product; (D) stopping the flow of a reactant substream (120a, 120b, 120c) to one or more of the reaction trains (100a, 100b, 100c); and (E) continuing to flow the reactant feed 1010 stream to the remainder of reaction trains (100a, 100b, 100c) in the plant 1000 at an overall process flow rate for the flow of fresh synthesis gas that is within up to about 15%, or up to about 10%, or up to about 5%, or up to about 2%, or up to about 1%, of the overall process flow rate for the flow of fresh synthesis gas used in step (A). During step (C) a mixture of fresh synthesis gas and a recycled tail gas may flow into the Fischer-Tropsch reactor of each reaction train. During step (E) the flow of recycled tail gas into the Fischer-Tropsch reactor of the one or more of the remainder of the reaction trains in the plant may be stopped or reduced in order to allow for maintaining a desired overall flow of fresh synthesis gas into the plant.

Referring to FIG. 2, in an embodiment, the synthesis gas conversion process (e.g., Fischer-Tropsch process) is conducted in plant 1000 comprising a plurality of reaction trains 100a, 100b and 100c. Each reaction train comprises a Fischer-Tropsch reactor 110a, 110b, and 110c containing a Fischer-Tropsch catalyst. The reaction trains 100a, 100b, and 100c are connected to a reactant feed stream 1010 comprising fresh synthesis gas. The flow of synthesis gas into and the flow of effluent out of the Fischer-Tropsch reactor of one or more of the reaction trains (100a, 100b, 100c) may be stopped, while the flow of synthesis gas into and the flow of effluent out of the other reaction trains in the plant 1000 may be continued. The method may comprise: flowing the reactant feed stream to the plurality of reaction trains (100a, 100b, 100c); dividing the reactant feed stream 1010 into a reactant substream (120a, 120b, 120c) for each reaction train (100a, 100b, 100c); and flowing each reactant substream through a reaction train to convert the reactants in the reactant substream to a Fischer-Tropsch product. The temperature of the Fischer-Tropsch product flowing out of each reaction train in the plant 1000 may be the same or substantially the same. In an embodiment, the temperature of the Fischer-Tropsch product flowing out of one of the reaction trains may be within about 10° C., or about 5° C., or about 2° C., or about 1° C., of the temperature of the Fischer-Tropsch product flowing out of another of the reaction trains in the plant 1000.

When a microchannel reactor is used, the fresh synthesis gas or the reactant mixture flows through one or more process microchannels in the reactor in contact with a Fischer-Tropsch catalyst to form a Fischer-Tropsch product. The Fischer-Tropsch product may comprise a mixture of FT liquid, FT wax, and FT tail gas. The FT tail gas may comprise CO and H$_2$. The reaction is exothermic. The reaction may be controlled using a heat exchange fluid which flows through the Fischer-Tropsch reactor 110 as indicated by arrows 170 and 180. In an embodiment, the heat exchange fluid may comprise steam. The Fischer-Tropsch product flows out of the Fischer-Tropsch reactor 110 as indicated by arrow 150. FT tail gas is separated from the Fischer-Tropsch product, as indicated by arrow 130, and recycled to be combined with the fresh synthesis gas. Part of the FT tail gas may be separated from the process, as indicated by arrow 135, if it is desired to adjust the ratio of fresh synthesis gas to FT tail gas in the reactant mixture. With FT tail gas separated from the Fischer-Tropsch product, the remainder of the Fischer-Tropsch product, which is indicated by arrow 160, comprises a FT liquid and/or FT wax, which can be subjected to further processing.

The synthesis gas conversion (e.g., Fischer-Tropsch reaction process) illustrated in FIG. 1 may be referred to as a reaction train. In a production facility or plant, the Fischer-Tropsch reaction may be conducted in a plurality of reaction trains that may be connected to a common source of fresh synthesis gas. Referring to FIG. 2, plant 1000 contains three reaction trains 100a, 100b and 100c, each of which is connected to fresh synthesis gas line 1010. Although three reaction trains are illustrated in FIG. 2, it is to be understood that plant 1000 may contain any desired number of reaction trains, for example, from 1 to about 1000 reaction trains, or from 1 to about 500 reaction trains, or from 1 to about 200 reaction trains, or from 1 to about 100 reaction trains, or from 1 to about 50 reaction trains, or from 1 to about 20 reaction trains, or from 1 to about 10 reaction trains, or from 1 to about 5 reaction trains. In operation, fresh synthesis gas from fresh synthesis gas line 1010 is divided into substreams 120a, 120b and 120c, which flow into reaction trains 100a, 100b and 100c, respectively.

The reaction train 100a employs the use of Fischer-Tropsch reactor 110a. In operation, fresh synthesis gas substream 120a flows from fresh synthesis gas line 1010 into the Fischer-Tropsch reactor 110a. Alternatively, the fresh synthesis gas may be combined with recycled tail gas 130a to form reactant mixture 140a which flows into the Fischer-Tropsch reactor 110a. The fresh synthesis gas may be combined with the recycled tail gas upstream of the Fischer-Tropsch reactor 110a, as shown in FIG. 2, or in the Fischer-Tropsch reactor 110a. The reaction may be controlled using a heat exchange fluid which flows through the Fischer-Tropsch reactor 110a as indicated by arrows 170a and 180a. The Fischer-Tropsch product flows out of the Fischer-Tropsch reactor 110a as indicated by arrow 150a. FT tail gas is separated from the Fischer-Tropsch product, as indicated by arrow 130a, and may be recycled to be combined with the fresh synthesis gas. Part of the FT tail gas may be separated from the process, as indicated by arrow 135a, if it is desired to adjust the ratio of fresh synthesis gas to FT tail gas in the reactant mixture. With FT tail gas separated from the Fischer-Tropsch product, the remainder of the Fischer-Tropsch product, which is indicated by arrow 160a, comprises a FT liquid and/or FT wax. The FT liquid and/or FT wax can be subjected to further processing.

The reaction train 100b employs the use of Fischer-Tropsch reactor 110b. In operation, fresh synthesis gas substream 120b flows from fresh synthesis gas line 1010 into the Fischer-Tropsch reactor 110b. Alternatively, the fresh synthesis gas may be combined with recycled tail gas 130b to form reactant mixture 140b which flows into the Fischer-Tropsch reactor 110b. The fresh synthesis gas may be combined with the recycled tail gas upstream of the Fischer-Tropsch reactor 110b, as shown in FIG. 2, or in the Fischer-Tropsch reactor 110b. The reaction may be controlled using a heat exchange fluid which flows through the Fischer-Tropsch reactor 110b as indicated by arrows 170b and 180b. The Fischer-Tropsch product flows out of the Fischer-Tropsch reactor 110b as indicated by arrow 150b. FT tail gas is separated from the Fischer-Tropsch product, as indicated by arrow 130b, and may be recycled to be combined with the fresh synthesis gas. Part of the FT tail gas may be separated from the process, as indicated by arrow 135b, if it is desired to adjust the ratio of fresh synthesis gas to FT tail gas in the reactant mixture. With FT tail gas separated from the Fischer-Tropsch product, the remainder of the Fischer-Tropsch product, which is indicated by arrow 160b, comprises a FT liquid and/or FT wax. The FT liquid and/or FT wax can be subjected to further processing.

The reaction train 100c employs the use of Fischer-Tropsch reactor 110c. In operation, fresh synthesis gas substream 120c flows from fresh synthesis gas line 1010 into the Fischer-Tropsch reactor 110c. Alternatively, the fresh synthesis gas may be combined with recycled tail gas 130c to form reactant mixture 140c which flows into the Fischer-Tropsch reactor 110c. The fresh synthesis gas may be combined with the recycled tail gas upstream of the Fischer-Tropsch reactor 110c, as shown in FIG. 2, or in the Fischer-Tropsch reactor 110c. The reaction may be controlled using a heat exchange fluid which flows through the Fischer-Tropsch reactor 110c as indicated by arrows 170c and 180c. The Fischer-Tropsch product flows out of the Fischer-Tropsch reactor 110c as indicated by arrow 150c. FT tail gas is separated from the Fischer-Tropsch product, as indicated by arrow 130c, and may be recycled to be combined with the fresh synthesis gas. Part of the FT tail gas may be separated from the process, as indicated by arrow 135c, if it is desired to adjust the ratio of fresh synthesis gas to FT tail gas in the reactant mixture. With FT tail gas separated from the Fischer-Tropsch product, the remainder of the Fischer-Tropsch product, which is indicated by arrow 160c, comprises a FT liquid and/or FT wax. The FT liquid and/or FT wax can be subjected to further processing.

In an embodiment, the temperature of the product streams 150a, 150b and 150c may be the same, or substantially the same, that is, within about 10° C., or about 5° C., or about 2° C., or about 1° C. of each other.

Figure 3:
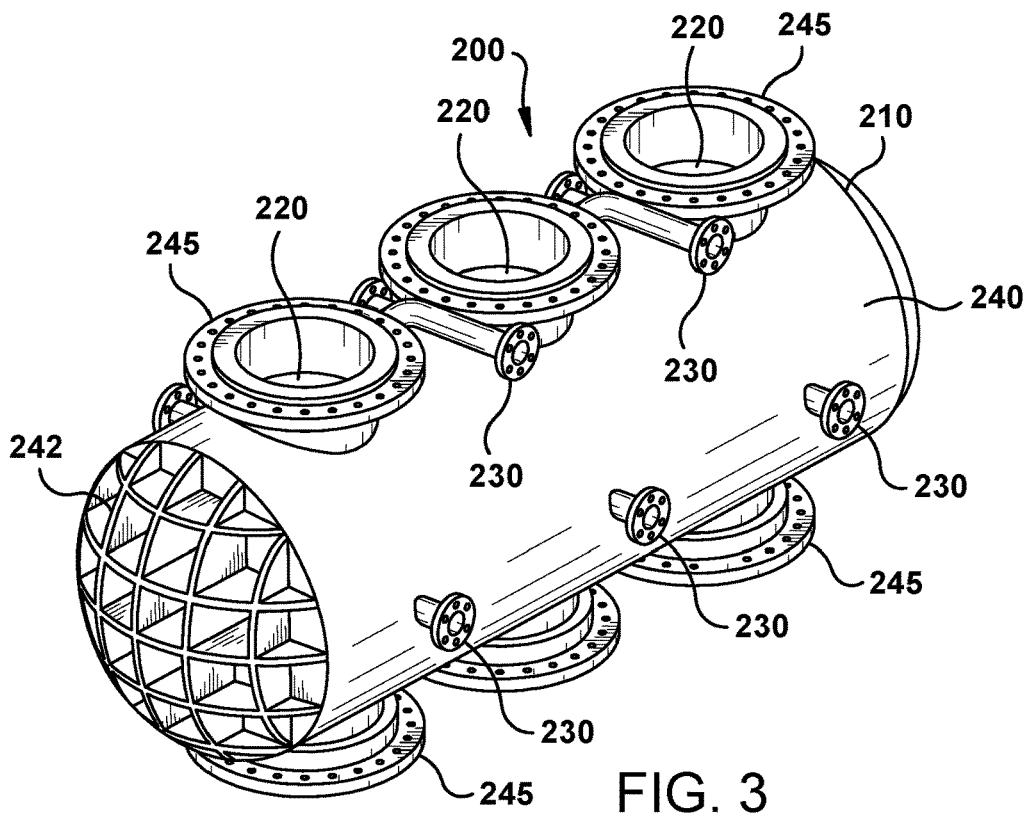
FIG. 3 is a schematic illustration of a microchannel reactor that can be used with the synthesis gas conversion processes referred to above.

The synthesis gas conversion microchannel reactor (e.g., Fischer-Tropsch microchannel reactor) that may be used is illustrated in FIG. 3. Referring to FIG. 3, microchannel reactor 200 comprises containment vessel 210 which contains or houses three microchannel reactor cores 220. Although FIG. 3 shows containment vessel 210 containing or housing three microchannel reactor cores 220, it is to be understood that any desired number of microchannel reactor cores 220 may be contained or housed within containment vessel 210. For example, containment vessel 210 may be used to contain or house from 1 to about 12 microchannel reactor cores, or from 1 to about 8 microchannel reactor cores, or from 1 to about 4 microchannel reactor cores. The containment vessel 210 may be a pressurizable vessel. The containment vessel 210 includes inlets and outlets 230 allowing for the flow of reactants into the microchannel reactor cores 220, product out of the microchannel reactor cores 220, and heat exchange fluid into and out of the microchannel reactor cores 220.

One of the inlets 230 may be connected to a header or manifold which is provided for flowing reactants to process microchannels in each of the microchannel reactor cores 220. One of the inlets 230 is connected to a header or manifold which is provided for flowing a heat exchange fluid to heat exchange channels in each of the microchannel reactor cores 220. One of the outlets 230 is connected to a manifold or footer which provides for product flowing out of the process microchannels in each of the microchannel reactor cores 220. One of the outlets 230 is connected to a manifold or footer to provide for the flow of the heat exchange fluid out of the heat exchange channels in each of the microchannel reactor cores 220.

The containment vessel 200 may be constructed using any suitable material sufficient for countering operating pressures that may develop within the microchannel reactor cores 220. For example, the shell 240 and reinforcing ribs 242 of the containment vessel 210 may be constructed of cast steel. The flanges 245, couplings and pipes may be constructed of 316 stainless steel. The containment vessel 210 may have any desired diameter, for example, from about 10 to about 1000 cm, or from about 50 to about 300 cm. The axial length of the containment vessel 210 may be of any desired value, for example, from about 0.5 to about 50 meters, or from about 1 to about 20 meters, or from about 1 to about 10 meters, or from about 1 to about 5 meters.

Figure 4:
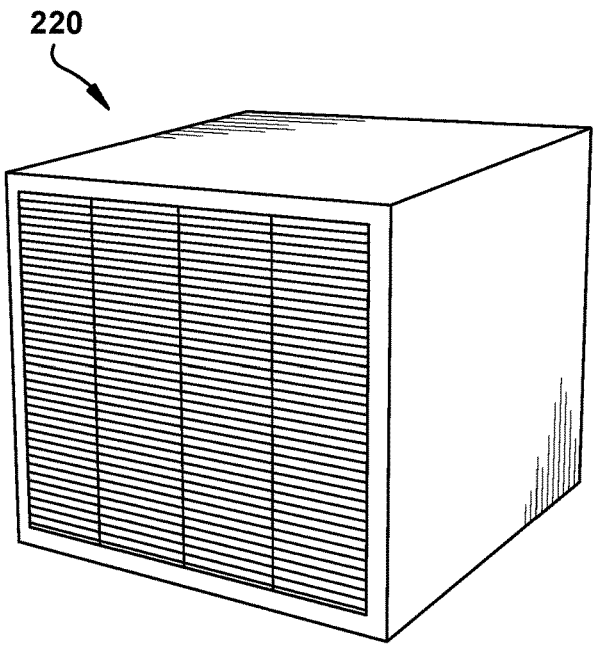
FIGS. 4 and 5 are schematic illustrations of a microchannel reactor core that can be used in the microchannel reactor illustrated in FIG. 3.
Figure 5:
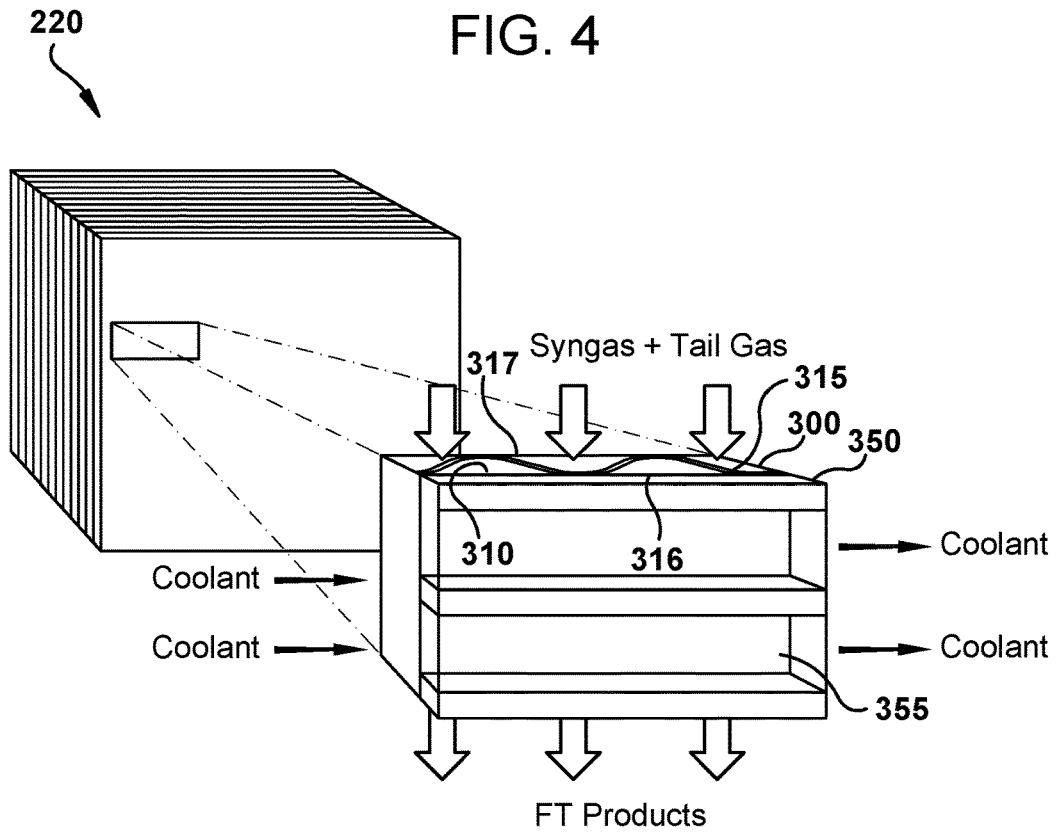

The microchannel reactor core 220 may comprise one or more layers of process microchannels and heat exchange channels stacked one above the other or positioned side-by-side to form a microchannel reactor core; see, FIGS. 4 and 5. The microchannel reactor core 220 may have the form of a three-dimensional block which has six faces that are squares or rectangles. The microchannel reactor core 220 may have the same cross-section along a length. The microchannel reactor core 220 may be in the form of a parallel or cubic block or prism. The microchannel reactor core 220 may have a length, width and height of any dimension, for example, a length in the range from about 0.1 to about 5 meters, about 0.01 to about 3 meters, or from about 0.1 to about 2 meters, or from about 0.1 to about 1.5 meters, or from about 0.1 to about 1 meter, or from about 0.1 to about 0.75 meter, or from about 0.1 to about 0.5 meter, or from about 0.1 to about 0.25 meter, or from about 0.1 to about 0.15 meter. The microchannel core 220 may have a width in the range from about 0.1 to about 5 meters, about 0.1 to about 3 meters, or from about 0.1 to about 2 meters, or from about 0.1 to about 1.5 meters, or from about 0.1 to about 1 meter, or from about 0.1 to about 0.75 meter, or from about 0.1 to about 0.5 meter, or from about 0.1 to about 0.25 meter, or from about 0.1 to about 0.15 meter. The microchannel reactor core 220 may have a height in the range from about 0.1 to about 5 meters, or about 0.1 to about 3 meters, or from about 0.1 to about 2 meters, or from about 0.1 to about 1.5 meters, or from about 0.1 to about 1 meter, or from about 0.1 to about 0.75 meter, or from about 0.1 to about 0.5 meter, or from about 0.1 to about 0.25 meter, or from about 0.1 to about 0.15 meter.

Figure 7:
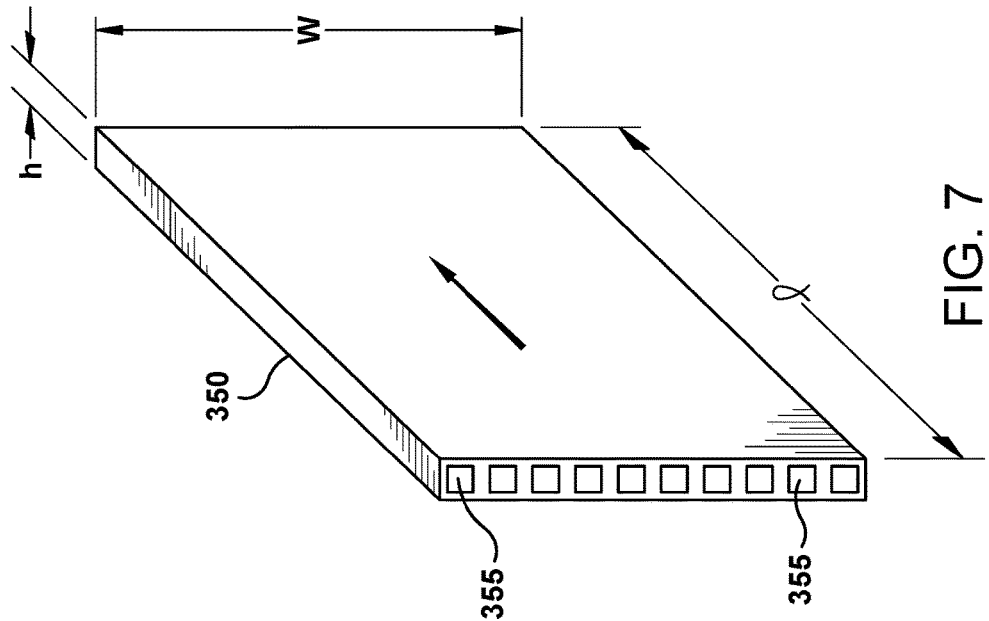
FIG. 7 is a schematic illustration of a layer of heat exchange channels that can be used in the microchannel reactor core illustrated in FIGS. 4 and 5. The heat exchange channels may be microchannels.
Figure 6:
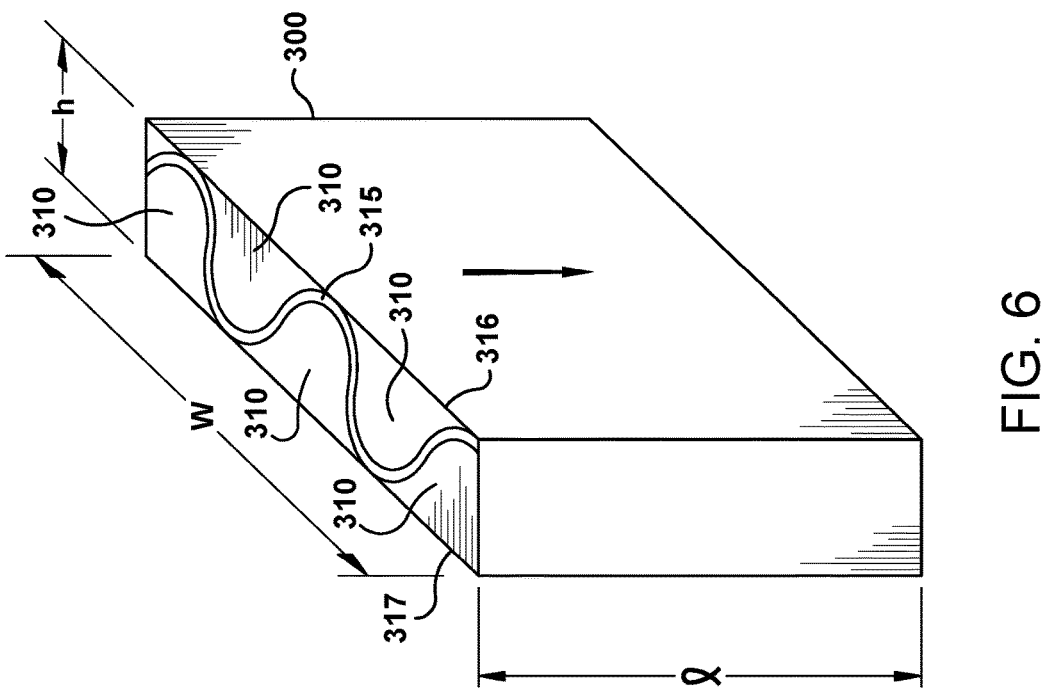
FIG. 6 is a schematic illustration of a layer of process microchannels that can be used in the microchannel reactor core illustrated in FIGS. 4 and 5. The layer of process microchannels comprises a waveform positioned in a space between planar plates. The process microchannels comprise channels formed by the sides of the waveform and the planar plates. The space between the planar plates may have the dimensions of a microchannel (i.e., a height of up to about 10 mm) and may also be referred to as a microchannel or a process microchannel. A synthesis gas conversion catalyst (e.g., a Fischer-Tropsch catalyst) may be positioned in the process microchannels.

The microchannel reactor core 220 may contain a plurality of layers of process microchannels and a plurality of layers of heat exchange channels. These are illustrated in FIGS. 5-7. Referring to FIGS. 5-7, microchannel reactor core 220 may contain from 1 to about 1000 layers 300 of process microchannels 310, or from about 1 to about 500, or from 1 to about 400, or from 1 to about 300, or from 1 to about 200, or from 1 to about 100, or from 1 to about 50, or from 1 to about 25, or from 1 to about 10, or from 1 to about 5 of such layers. The catalyst may be positioned in the process microchannels 310 and may be in any form including fixed beds of particulate solids or any of the various structured catalyst forms described below. The microchannel reactor core 220 may contain from 1 to about 1000 layers 350 of heat exchange channels 355, or from 1 to about 500, or from 1 to about 400, or from 1 to about 300, or from 1 to about 200, or from 1 to about 100, or from 1 to about 50, or from 1 to about 25, or from 1 to about 10, or from 1 to about 5 of such layers.

The layers 300 of process microchannels 310 may be constructed using waveforms in the form of right angled corrugated sheet inserts 315. These waveform inserts 315 may have rounded edges rather than sharp edges. These waveform inserts may have a sinusoidel form as shown in FIGS. 5 and 6. The waveform insert 315 may be positioned between opposing planar plates 316 and 317. This is shown in FIGS. 5 and 6. In this manner the microchannels may be defined on three sides by the waveform insert 315 and on the fourth side by one of the planar plates 316 or 317. The layers of process microchannels as well as the layers of heat exchange channels may be formed in this manner. Also, the space between opposed planar plates 316 and 317 containing the waveform 315 may have the dimensions of a micorchannel (e.g., a height of up to about 10 mm) and may therefore also be referred to as a microchannel. Microchannel reactors made using waveforms are disclosed in WO 2008/030467, which is incorporated herein by reference.

Each layer 300 of process microchannels 310 may have a height (h) in the range from about 0.1 to about 10 mm. Each layer 300 may have a width (w) in the range from about 0.1 to about 5 meters, or about 0.1 to about 3 meters, or about 0.1 to about 2 meters, or about 0.1 to about 1 meter, or about 0.1 to about 0.5 meter. The length (l) of each layer 300 may be up to about 5 meters, or from about 0.1 to about 5 meters, or from about 0.1 to about 3 meters, or from about 0.1 to about 2.5 meters, or from about 0.1 to about 2 meters, or from about 0.1 to about 1.5 meters, or from about 0.1 to about 1 meter, or from about 0.15 to about 5 meters, or from about 0.15 to about 5 meters, or from about 0.15 to about 3 meters, or from about 0.15 to about 2.5 meters, or from about 0.15 to about 2 meters, or from about 0.15 to about 1.5 meters, or from about 0.15 to about 1 meter. The length (l) may be in the range from about 0.1 to about 0.8 meter, or from about 0.1 to about 0.6 meter, or from about 0.1 to about 0.5 meter, or from about 0.1 to about 0.3 meter.

Each layer 350 of heat exchange channels 355 may have a height (h) in the range from about 0.1 to about 10 mm. Each layer 350 may have a width (w) in the range from 0.1 to about 5 meters, or 0.1 to about 3 meters, or 0.1 to about 2 meters, or about 0.1 to about 1 meter, or about 0.01 to about 0.5 meter. The length (l) of each layer 350 may be from about 0.1 to about 5 meters, or from about 0.1 to about 3 meters, or from about 0.1 to about 2.5 meters, or from about 0.1 to about 2 meters, or from about 0.1 to about 1.5 meters, or from about 0.1 to about 1 meter, or from about 0.15 to about 3 meters, or from about 0.15 to about 2.5 meters, or from about 0.15 to about 2 meters, or from about 0.15 to about 1.5 meters, or from about 0.15 to about 1 meter. The length (l) may be in the range from about 0.1 to about 0.8 meter, or from about 0.1 to about 0.6 meter, or from about 0.05 to about 0.5 meter, or from about 0.1 to about 0.3 meter.

Each layer 300 of process microchannels 310 may have from 1 to about 5000 process microchannels 310, or from 1 to about 2000 process microchannels, or from 1 to about 1000 process microchannels, or from 1 to about 500 process microchannels, or from 1 to about 250 process microchannels, or from 1 to about 100 process microchannels, or from 1 to about 50 process microchannels. The process microchannels 310 may have cross sections having any shape, for example, square, rectangle, circle, semi-circle, etc. The internal height of each process microchannel 310 may be considered to be the smaller of the internal dimensions normal to the direction of flow of reactants and product through the process microchannel. Each of the process microchannels 310 may have internal height or width in the range of up to about 10 mm, or from about 0.05 to about 10 mm, or from about 0.05 to about 8 mm, or from about 0.05 to about 7 mm, or from about 0.05 to about 5 mm, or from about 0.05 to about 3 mm, or from about 0.05 to about 2 mm, or from about 0.05 to about 1.5 mm, or from about 1 to about 10 mm, or from about 1 to about 8 mm, or from about 1 to about 7 mm, or from about 1 to about 5 mm, or from about 1 to about 3 mm, or from about 1 to about 2 mm, or from about 1 to about 1.5 mm. The other internal dimension of height or width may be of any dimension, for example, up to about 5 meters, or about 0.001 to about 5 meters, or about 0.001 to about 3 meters, or about 0.001 to about 2 meters, or about 0.001 to about 1 meter, or about 0.01 to about 0.5 meter, or about 1 to about 10 mm, or about 1 to about 8 mm, or about 1 to about 7 mm, or about 1 to about 5 mm, or about 1 to about 3 mm, or about 1 to about 2 mm. The length may be of any dimension, for example, up to about 5 meters, or from about 0.1 to about 5 meters, or from about 0.1 to about 3 meters, or from about 0.1 to about 2.5 meters, or from about 0.1 to about 2 meters, or from about 0.1 to about 1.5 meters, or from about 0.1 to about 1 meter, or from about 0.15 to about 5 meters, or from about 0.15 to about 3 meters, or from about 0.15 to about 2.5 meters, or from about 0.15 to about 2 meters, or from about 0.15 to about 1.5 meters, or from about 0.15 to about 1 meter. The length may be in the range from about 0.1 to about 0.8 meter, or from about 0.1 to about 0.6 meter, or from about 0.05 to about 0.5 meter, or from about 0.1 to about 0.3 meter.

Each layer 350 of heat exchange channels 355 may have from 1 to about 5000 heat exchange channels, or from 1 to about 2000 heat exchange channels, or from 1 to about 1000 heat exchange channels, or from 1 to about 500 heat exchange channels, or from 1 to about 250 heat exchange channels, or from 1 to about 100 heat exchange channels, or from 1 to about 50 heat exchange channels. The heat exchange channels 355 may be microchannels or they may have larger dimensions that would classify them as not being microchannels. Each of the heat exchange channels 355 may have a cross section having any shape, for example, a square, rectangle, circle, semi-circle, etc. The internal height of each heat exchange channel 355 may be considered to be the smaller of the internal dimensions normal to the direction of flow of heat exchange fluid in the heat exchange channels. Each of the heat exchange channels 355 may have internal height or width in the range of up to about 10 mm, or from about 0.05 to about 10 mm, or from about 0.05 to about 8 mm, or from about 0.05 to about 7 mm, or from about 0.05 to about 5 mm, or from about 0.05 to about 3 mm, or from about 0.05 to about 2 mm, or from about 0.05 to about 1.5 mm, or from about 1 to about 10 mm, or from about 1 to about 8 mm, or from about 1 to about 7 mm, or from about 1 to about 5 mm, or from about 1 to about 3 mm, or from about 1 to about 2 mm, or from about 1 to about 1.5 mm. The other internal dimension of height or width may be of any dimension, for example, up to about 5 meters, or about 0.001 to about 5 meters, or about 0.001 to about 3 meters, or about 0.001 to about 2 meters, or about 0.001 to about 1 meter, or about 0.01 to about 0.5 meter, or about 1 to about 10 mm, or about 1 to about 8 mm, or about 1 to about 7 mm, or about 1 to about 5 mm, or about 1 to about 3 mm, or about 1 to about 2 mm. The length may be of any dimension, for example, up to about 5 meters, or about 0.1 to about 5 meters, or from about 0.1 to about 3 meters, or from about 0.1 to about 2.5 meters, or from about 0.1 to about 2 meters, or from about 0.1 to about 1.5 meters, or from about 0.1 to about 1 meter, or from about 0.15 to about 5 meters, or from about 0.15 to about 3 meters, or from about 0.15 to about 2.5 meters, or from about 0.15 to about 2 meters, or from about 0.15 to about 1.5 meters, or from about 0.15 to about 1 meter. The length may be in the range from about 0.1 to about 0.8 meter, or from about 0.1 to about 0.6 meter, or from about 0.05 to about 0.5 meter, or from about 0.1 to about 0.3 meter.

The microchannel reactor core 220 may be made of any material that provides sufficient strength, dimensional stability and heat transfer characteristics to permit operation of the desired process. These materials may include aluminum; titanium; nickel; platinum; rhodium; copper; chromium; alloys of any of the foregoing metals; brass; steel (e.g., stainless steel); quartz; silicon; or a combination of two or more thereof. Each microchannel reactor may be constructed of stainless steel with one or more copper or aluminum waveforms being used for forming the channels.

The microchannel reactor core 220 may be fabricated using known techniques including wire electrodischarge machining, conventional machining, laser cutting, photochemical machining, electrochemical machining, molding, water jet, stamping, etching (for example, chemical, photochemical or plasma etching) and combinations thereof.

The microchannel reactor core 220 may be constructed by forming plates with portions removed that allow flow passage. A stack of plates may be assembled via diffusion bonding, laser welding, diffusion brazing, and similar methods to form an integrated device. The microchannel reactors may be assembled using a combination of plates and partial plates or strips. In this method, the channels or void areas may be formed by assembling strips or partial plates to reduce the amount of material required.

The microchannel reactor core 220 may comprise a plurality of plates in a stack defining a plurality of process layers and a plurality of heat exchange layers, each plate having a peripheral edge, the peripheral edge of each plate or shim being welded to the peripheral edge of the next adjacent plate to provide a perimeter seal for the stack. This is shown in US 2012/0095268 A1, which is incorporated herein by reference.

The containment vessel 210 may include a control mechanism to maintain the pressure within the containment vessel at a level that is at least as high as the internal pressure within the microchannel reactor cores 220. The internal pressure within the containment vessel 210 may be in the range from about 10 to about 60 atmospheres, or from about 15 to about 30 atmospheres during the operation of a synthesis gas conversion process (e.g., Fischer-Tropsch process). The control mechanism for maintaining pressure within the containment vessel may comprise a check valve and/or a pressure regulator. The check valve or regulator may be programmed to activate at any desired internal pressure for the containment vessel. Either or both of these may be used in combination with a system of pipes, valves, controllers, and the like, to ensure that the pressure in the containment vessel 210 is maintained at a level that is at least as high as the internal pressure within the microchannel reactor cores 220. This is done in part to protect welds used to form the microchannel cores 220. A significant decrease in the pressure within the containment vessel 210 without a corresponding decrease of the internal pressure within the microchannel reactor cores 220 could result in a costly rupture of the welds within the microchannel reactor cores 220. The control mechanism may be designed to allow for diversion of one or more process gases into the containment vessel in the event the pressure exerted by the containment gas decreases.

In the design of a microchannel reactor it may be advantageous to provide a tailored heat exchange profile along the length of the process microchannels in order to optimize the reaction. This may be accomplished by matching the local release of heat given off by the synthesis gas conversion reaction (e.g., Fischer-Tropsch reaction) conducted in the process microchannels with heat removal or cooling provided by heat exchange fluid in heat exchange channels in the microchannel reactor. The extent of the synthesis gas conversion reaction (e.g., Fischer-Tropsch reaction) and the consequent heat release provided by the reaction may be higher in the front or upstream sections of the reaction zones in the process microchannels as compared to the back or downstream sections of the reaction zones. Consequently, the matching cooling requirements may be higher in the upstream section of the reaction zones as compared to the downstream sections of the reaction zones. Tailored heat exchange may be accomplished by providing more heat exchange or cooling channels, and consequently the flow of more heat exchange or cooling fluid, in thermal contact with upstream sections of the reaction zones in the process microchannels as compared to the downstream sections of the reaction zones. Alternatively or additionally, a tailored heat exchange profile may be provided by varying the flow rate of heat exchange fluid in the heat exchange channels. In areas where additional heat exchange or cooling is desired, the flow rate of the heat exchange fluid may be increased as compared to areas where less heat exchange or cooling is required. For example, a higher rate of flow of heat exchange fluid may be advantageous in the heat exchange channels in thermal contact with the upstream sections of the reaction zones in the process microchannels as compared to the heat exchange channels in thermal contact with the downstream sections of the reaction zones. Heat transfer from the process microchannels to the heat exchange channels may be designed for optimum performance by selecting optimum heat exchange channel dimensions and/or the rate of flow of heat exchange fluid per individual or groups of heat exchange channels. Additional design alternatives for tailoring heat exchange may relate to the selection and design of the synthesis gas conversion catalyst (e.g., Fischer-Tropsch catalyst) such as, particle size, catalyst formulation, packing density, use of a graded catalyst, or other chemical or physical characteristics, at specific locations within the process microchannels. These design alternatives may impact both heat release from the process microchannels as well as heat transfer to the heat exchange fluid. Temperature differentials between the process microchannels and the heat exchange channels, which may provide a driving force for heat transfer, may be constant or may vary along the length of the process microchannels.

The process microchannels may contain one or more surface features in the form of depressions in and/or projections from one or more interior walls of the process microchannels. The surface features may be used to disrupt the flow of fluid flowing in the channels. These disruptions in flow may enhance mixing and/or heat transfer. The surface features may be in the form of patterned surfaces. The microchannel reactor core 220 may be made by laminating a plurality of plates together. One or both major surfaces of the plates may contain surface features. Alternatively, the microchannel reactor core 220 may be assembled using some plates and some strips, or partial plates to reduce the total amount of metal required to construct the device. A plate containing surface features may be paired (on opposite sides of a microchannel) with another plate containing surface features. Pairing may create better mixing or heat transfer enhancement as compared to channels with surface features on only one major surface. The patterning may comprise diagonal recesses that are disposed over substantially the entire width of a microchannel surface. The patterned surface feature area of a wall may occupy part of or the entire length of a microchannel surface. Surface features may be positioned over at least about 10%, or at least about 20%, or at least about 50%, or at least about 80% of the length of a channel surface. Each diagonal recesses may comprise one or more angles relative to the flow direction. Successive recessed surface features may comprise similar or alternate angles relative to other recessed surface features.

The synthesis gas conversion process (e.g., Fischer-Tropsch process microchannels) may be characterized by having bulk flow paths. The term "bulk flow path" refers to an open path (contiguous bulk flow region) within the process microchannels or combustion channel. A contiguous bulk flow region allows rapid fluid flow through the channels without large pressure drops. In one embodiment, the flow of fluid in the bulk flow region is laminar. Bulk flow regions within each process microchannel or combustion channel may have a cross-sectional area of about 0.05 to about 10,000 mm$^2$, or about 0.05 to about 5000 mm$^2$, or about 0.1 to about 2500 mm$^2$. The bulk flow regions may comprise from about 5% to about 95%, or about 30% to about 80% of the cross-section of the process microchannels or combustion channel.

The contact time of the reactants with the catalyst may range up to about 3600 milliseconds (ms), or up to about 2000 ms, or in the range from about 10 to about 2600 ms, or from about 10 ms to about 2000 ms, or about 20 ms to about 500 ms, or from about 200 to about 400 ms, or from about 240 to about 350 ms.

The space velocity (or gas hourly space velocity (GHSV)) for the flow of fluid in the process microchannels may be at least about 1000 hr$^{-1}$ (normal liters of feed/hour/liter of volume within the process microchannels), or at least about 1800 hr$^{-1}$, or from about 1000 to about 1,000,000 hr$^{-1}$, or from about 5000 to about 20,000 hr$^{-1}$.

The pressure within the process microchannels may be up to about 100 atmospheres, or in the range from about 1 to about 100 atmospheres, or from about 1 to about 75 atmospheres, or from about 2 to about 40 atmospheres, or from about 2 to about 10 atmospheres, or from about 10 to about 50 atmospheres, or from about 20 to about 30 atmospheres.

The pressure drop of fluids as they flow in the process microchannels may range up to about 30 atmospheres per meter of length of channel (atm/m), or up to about 25 atm/m, or up to about 20 atm/m. The pressure drop may be in the range from about 10 to about 20 atm/m.

The Reynolds Number for the flow of fluid in the process microchannels may be in the range of about 10 to about 4000, or about 100 to about 2000.

The average temperature in the process microchannels may be in the range from about 150 to about 300° C., or in the range from about 175 to about 225° C., of in the range from about 190 to about 220° C., or from about 195 to about 215° C.

The heat exchange fluid entering the heat exchange channels of the microchannel reactor core 220 may be at a temperature in the range of about 100° C. to about 400° C., or about 200° C. to about 300° C. The heat exchange fluid exiting the heat exchange channels may be at a temperature in the range of about 150° C. to about 400° C., or about 200° C. to about 350° C. The residence time of the heat exchange fluid in the heat exchange channels may range from about 1 to about 2000 ms, or about 10 to about 500 ms. The pressure drop for the heat exchange fluid as it flows through the heat exchange channels may range up to about 10 atm/m, or from about 1 to about 10 atm/m, or from about 3 to about 7 atm/m, or about 5 atm/m. The heat exchange fluid may be in the form of a vapor, a liquid, or a mixture of vapor and liquid. The Reynolds Number for the flow of the heat exchange fluid in heat exchange channels may be from about 10 to about 4000, or about 100 to about 2000.

The heat exchange fluid used in the heat exchange channels in the microchannel reactor core 220 may be any heat exchange fluid suitable for cooling an exothermic synthesis gas conversion reaction (e.g., Fischer-Tropsch exothermic reaction). These may include air, steam, liquid water, gaseous nitrogen, other gases including inert gases, carbon monoxide, oils such as mineral oil, and heat exchange fluids such as Dowtherm A and Therminol which are available from Dow-Union Carbide.

The heat exchange channels used in the microchannel reactor core 220 may comprise process channels wherein an endothermic process is conducted. These heat exchange process channels may be microchannels. Examples of endothermic processes that may be conducted in the heat exchange channels include steam reforming and dehydrogenation reactions. Steam reforming of an alcohol that occurs at a temperature in the range from about 200° C. to about 300° C. is an example of an endothermic process that may be used. The incorporation of a simultaneous endothermic reaction to provide an improved cooling may enable a typical heat flux of roughly an order of magnitude above convective cooling.

The heat exchange fluid may undergo a partial or full phase change as it flows in the heat exchange channels of the microchannel reactor core 220. This phase change may provide additional heat removal from the process microchannels beyond that provided by convective cooling. For a liquid heat exchange fluid being vaporized, the additional heat being transferred from the Fischer-Tropsch process microchannels may result from the latent heat of vaporization required by the heat exchange fluid. In one embodiment, about 50% by weight of the heat exchange fluid may be vaporized, or about 35% by weight may be vaporized, or about 20% by weight may be vaporized, or about 10% by weight, or about 5% by weight may be vaporized, or about 2 to about 3% by weight may be vaporized.

The heat flux for heat exchange in the microchannel reactor core 220 may be in the range from about 0.01 to about 500 watts per square centimeter of surface area of the one or more heat transfer walls of the process microchannels (W/cm$^2$) in the microchannel reactor, or in the range from about 0.1 to about 250 W/cm$^2$, or from about 1 to about 125 W/cm$^2$, or from about 1 to about 100 W/cm$^2$, or from about 1 to about 50 W/cm$^2$, or from about 1 to about 25 W/cm$^2$, or from about 1 to about 10 W/cm$^2$. The range may be from about 0.2 to about 5 W/cm$^2$, or about 0.5 to about 3 W/cm$^2$, or from about 1 to about 2 W/cm$^2$.

The control of heat exchange during the synthesis gas conversion process (e.g., Fischer-Tropsch reaction process) may be advantageous for controlling selectivity towards the desired product due to the fact that such added cooling may reduce or eliminate the formation of undesired by-products from undesired parallel reactions with higher activation energies.

The pressure within each individual heat exchange channel in the microchannel reactor core 220 may be controlled using passive structures (e.g., obstructions), orifices and/or mechanisms upstream of the heat exchange channels or in the channels. By controlling the pressure within each heat exchange channel, the temperature within each heat exchange channel can be controlled. A higher inlet pressure for each heat exchange channel may be used where the passive structures, orifices and/or mechanisms let down the pressure to the desired pressure. By controlling the temperature within each heat exchange channel, the temperature in the process microchannels can be controlled. Thus, for example, each process microchannel may be operated at a desired temperature by employing a specific pressure in the heat exchange channel adjacent to or in thermal contact with the process microchannel. This provides the advantage of precisely controlled temperatures for each process microchannel. The use of precisely controlled temperatures for each process microchannel provides the advantage of a tailored temperature profile and an overall reduction in the energy requirements for the process.

In a scale up device, for certain applications, it may be required that the mass of the process fluid be distributed uniformly among the microchannels. Such an application may be when the process fluid is required to be heated or cooled down with adjacent heat exchange channels. The uniform mass flow distribution may be obtained by changing the cross-sectional area from one parallel microchannel to another microchannel. The uniformity of mass flow distribution may be defined by Quality Index Factor (Q-factor) as indicated below. A Q-factor of 0% means absolute uniform distribution.

$$Q = \frac{\dot{m}_{max} - \dot{m}_{min}}{\dot{m}_{max}} \times 100$$

A change in the cross-sectional area may result in a difference in shear stress on the wall. In one embodiment, the Q-factor for the microchannel reactor 110 may be less than about 50%, or less than about 20%, or less than about 5%, or less than about 1%.

The superficial velocity for fluid flowing in the process microchannels may be at least about 0.01 meters per second (m/s), or at least about 0.1 m/s, or in the range from about 0.01 to about 100 m/s, or in the range from about 0.01 to about 10 m/s, or in the range from about 0.1 to about 10 m/s, or in the range from about 1 to about 100 m/s, or in the range from about 1 to about 10 m/s.

The free stream velocity for fluid flowing in the process microchannels may be at least about 0.001 m/s, or at least about 0.01 m/s, or in the range from about 0.001 to about 200 m/s, or in the range from about 0.01 to about 100 m/s, or in the range from about 0.01 to about 200 m/s.

The conversion of CO from the fresh synthesis gas may be about 70% or higher, or about 75% or higher, or about 80% or higher, or about 90% or higher, or about 91% or higher, or about 92% or higher, or from about 88% to about 95%, or from about 90% to about 94%, or from about 91% to about 93%. If a tail gas recycle is used, the one-pass conversion of CO for the CO in the reactant mixture (i.e., fresh synthesis gas plus recycled tail gas) may be in the range from about 50% to about 90%, or from about 65% to about 85%.

The selectivity to methane in the Fischer-Tropsch (FT) product may be in the range from about 0.01 to about 10%, or about 1% to about 5%, or about 1% to about 10%, or about 3% to about 9%, or about 4% to about 8%.

The Fischer-Tropsch product may comprise a gaseous product fraction and a liquid product fraction. The gaseous product fraction may include hydrocarbons boiling below about 350° C. at atmospheric pressure (e.g., tail gases through middle distillates). The liquid product fraction (the condensate fraction) may include hydrocarbons boiling above about 350° C. (e.g., vacuum gas oil through heavy paraffins).

The Fischer-Tropsch product fraction boiling below about 350° C. may be separated into a tail gas fraction and a condensate fraction, e.g., normal paraffins of about 5 to about 20 carbon atoms and higher boiling hydrocarbons, using, for example, a high pressure and/or lower temperature vapor-liquid separator, or low pressure separators or a combination of separators. The fraction boiling above about 350° C. (the condensate fraction) may be separated into a wax fraction boiling in the range of about 350° C. to about 650° C. after removing one or more fractions boiling above about 650° C. The wax fraction may contain linear paraffins of about 20 to about 50 carbon atoms with relatively small amounts of higher boiling branched paraffins. The separation may be effected using fractional distillation.

The Fischer-Tropsch product may include methane, wax and other heavy high molecular weight products. The product may include olefins such as ethylene, normal and iso-paraffins, and combinations thereof. These may include hydrocarbons in the distillate fuel ranges, including the jet or diesel fuel ranges.

Branching may be advantageous in a number of end-uses, particularly when increased octane values and/or decreased pour points are desired. The degree of isomerization may be greater than about 1 mole of isoparaffin per mole of n-paraffin, or about 3 moles of isoparaffin per mole of n-paraffin. When used in a diesel fuel composition, the product may comprise a hydrocarbon mixture having a cetane number of at least about 60.

The Fischer-Tropsch catalyst may comprise cobalt and a support. The catalyst may have a Co loading in the range from about 10 to about 60% by weight, or from about 15 to about 60% by weight, or from about 20 to about 60% by weight, or from about 25 to about 60% by weight, or from about 30 to about 60% by weight, or from about 32 to about 60% by weight, or from about 35 to about 60% by weight, or from about 38 to about 60% by weight, or from about 40 to about 60% by weight, or from about 40 to about 55% by weight, or about 40 to about 50% of cobalt.

The Fischer-Tropsch catalyst may further comprise a noble metal. The noble support metal may be one or more of Pd, Pt, Rh, Ru, Re, Ir, Au, Ag and Os. The noble metal may be one or more of Pd, Pt, Rh, Ru, Ir, Au, Ag and Os. The noble metal may be one or more of Pt, Ru and Re. The noble metal may be Ru. As an alternative, or in addition, the noble metal may be Pt. The Fischer-Tropsch catalyst may comprise from about 0.01 to about 30% in total of noble metal(s) (based on the total weight of all noble metals present as a percentage of the total weight of the catalyst precursor or activated catalyst), or from about 0.05 to about 20% in total of noble metal(s), or from about 0.1 to about 5% in total of noble metal(s), or about 0.2% in total of noble metal(s).

The Fischer-Tropsch catalyst may include one or more other metal-based components as promoters or modifiers. These metal-based components may also be present in the catalyst precursor and/or activated catalyst as carbides, oxides or elemental metals. A suitable metal for the one or more other metal-based components may be one or more of Zr, Ti, V, Cr, Mn, Ni, Cu, Zn, Nb, Mo, Tc, Cd, Hf, Ta, W, Re, Hg, Tl and the 4f-block lanthanides. Suitable 4f-block lanthanides may be La, Ce, Pr, Nd, Pm, Sm, Eu, Gd, Tb, Dy, Ho, Er, Tm, Yb and/or Lu. The metal for the one or more other metal-based components may be one or more of Zn, Cu, Mn, Mo and W. The metal for the one or more other metal-based components may be one or more of Re and Pt. The catalyst may comprise from about 0.01 to about 10% in total of other metal(s) (based on the total weight of all the other metals as a percentage of the total weight of the catalyst precursor or activated catalyst), or from about 0.1 to about 5% in total of other metals, or about 3% in total of other metals.

The Fischer-Tropsch catalyst may be derived from a catalyst precursor which may be activated to produce the Fischer-Tropsch catalyst, for instance by heating the catalyst precursor in hydrogen and/or a hydrocarbon gas (e.g., methane), or in a hydrogen or hydrocarbon gas diluted with another gas, such as nitrogen and/or methane, to convert at least some of the carbides or oxides to elemental metal. In the active catalyst, the cobalt may optionally be at least partially in the form of its carbide or oxide.

The Fischer-Tropsch catalyst precursor may be activated using a carboxylic acid as the reducing agent. The carboxylic acid may be chosen such that it minimizes the fracturing of the catalyst precursor whilst still ultimately producing an effective catalyst. A mixture of two or more carboxylic acids may be used. The carboxylic acid may be an alpha-hydroxy carboxylic acid, such as citric acid, glycolic acid, lactic acid, mandelic acid, or a mixture of two or more thereof.

The Fischer-Tropsch catalyst may include a catalyst support. The support may comprise a refractory metal oxide, carbide, carbon, nitride, or mixture of two or more thereof. The support may comprise alumina, zirconia, silica, titania, or a mixture of two or more thereof. The surface of the support may be modified by treating it with silica, titania, zirconia, magnesia, chromia, alumina, or a mixture of two or more thereof. The material used for the support and the material used for modifying the support may be different. The support may comprise silica and the surface of the silica may be treated with an oxide refractory solid oxide such as titania. The material used to modify the support may be used to increase the stability (e.g. by decreasing deactivation) of the supported catalyst. The catalyst support may comprise up to about 30% by weight of the oxide (e.g., silica, titania, magnesia, chromia, alumina, or a mixture of two or more thereof) used to modify the surface of the support, or from about 1% to about 30% by weight, or from about 5% to about 30% by weight, or from about 5% to about 25% by weight, or from about 10% to about 20% by weight, or from about 12% to about 18% by weight. The catalyst support may be in the form of a structured shape, pellets or a powder. The catalyst support may be in the form of particulate solids. While not wishing to be bound by theory, it is believed that the surface treatment provided for herein helps keep the Co from sintering during operation of the inventive Fischer-Tropsch process.

The deactivation rate of the Fischer-Tropsch catalyst may be such that it can be used in a Fischer-Tropsch synthesis for more than about 300 hours, or more than about 3,000 hours, or more than about 12,000 hours, or more than about 15,000 hours, all before a catalyst rejuvenation or regeneration is required.

The Fischer-Tropsch catalyst may be used for an extended period (e.g. >300 hours) with a deactivation rate of less than about 1.4% per day, or less than about 1.2% per day, or between about 0.1% and about 1% per day, or between about 0.03 and about 0.15% per day.

The synthesis gas conversion catalyst (e.g., the Fischer-Tropsch catalyst) may have any size and geometric configuration that fits within the reactor, e.g., the process microchannels. The catalyst may be in the form of particulate solids (e.g., pellets, powder, fibers, and the like) having a median particle diameter of about 1 to about 1000 µm (microns), or about 10 to about 750 µm, or about 25 to about 500 µm. The median particle diameter may be in the range from 50 to about 500 µm or about 100 to about 500 µm, or about 125 to about 400 µm, or about 170 to about 300 µm. In one embodiment, the catalyst may be in the form of a fixed bed of particulate solids.

The catalyst for the methanol and dimethyl ether reactions may comprise any catalyst suitable for synthesizing methanol or dimethyl ether from synthesis gas. These may include catalysts comprising copper, zinc and aluminum oxides (e.g., gamma-alumina), and optionally further containing, for example, oxides of one or more rare earth elements (i.e., elements 57-71), zirconium, yttrium, chromium, silver, gallium, vanadium, molybdenum, tungsten or titanium. The ranges of proportions may be from about 30 to about 70% by weight as copper, from about 20 to about 70% by weight as zinc, and up to about 15% by weight as aluminum. Examples of methanol synthesis catalysts that may be used may include those disclosed in U.S. Pat. Nos. 4,596,782; 5,238,895; 5,254,520; 5,384,335; 5,610,202; 5,767,039; 6,114,279; 6,342,538 B1; 6,433,029 B1; and 6,486,219 B1; and U.S. Patent Publication 2002/0177741 A1.

The dimethyl ether catalysts that may be used may include those disclosed in U.S. Pat. Nos. 4,011,275; 6,069,180; 6,147,125; 6,248,795; 6,638,892; and J. L. Dubois et al., "Conversion of Carbon Dioxide to Dimethyl Ether and Methanol Over Hybrid Catalysts," Chem. Lett., (7) 1115-1118 (1992). These patents and publications are incorporated herein by reference.

The methanol forming catalyst may be used in combination with a dehydration catalyst to provide a synthesis-gas-to-dimethylether route. Examples of the dehydration catalyst that may be used include acidic oxides such as alumina, silica-alumina, zeolite, and silico-alumino-phosphate synthetic molecular sieves. These are disclosed in U.S. 2006/0020155A1 and US 2007/0244000A1, which are incorporated herein by reference. The methanol forming catalyst and the dehydration catalyst may be mixed or combined together in the same reaction zone. Alternatively, the dehydration catalyst may be positioned downstream of the methanol forming catalyst, either in the same microchannel reactor or in a separate microchannel reactor.

The catalyst used for the methane forming reactions may comprise any catalyst suitable for converting synthesis gas to methane. The catalyst may comprise nickel, iron, cobalt, ruthenium, molybdenum, vanadium, titanium, or a mixture of two or more thereof. The catalyst may comprise an oxide of any of the foregoing metals. The catalyst may comprise vanadium and/or molybdenum in the form of free metal, salt, oxide and/or sulfide on a porous, oxidic support comprising titanium dioxide. The catalyst may be promoted with one or more salts, hydroxides, oxides or sulfides of one or more metals belonging to Groups IA, IIA or IIIB of the Periodic Table. The catalyst may comprise vanadium sulfide promoted with ceruim sulfide on a porous support comprising titanium dioxide. The catalysts that may be used are described in U.S. Pat. No. 4,540,714, which is incorporated herein by reference.

Figure 8:
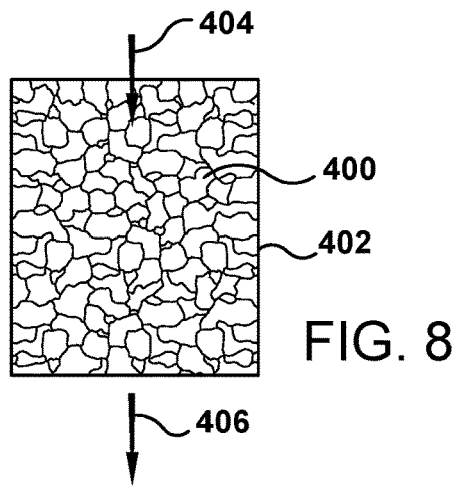
FIGS. 8-13 are schematic illustrations of catalysts or catalyst supports that may be used in the synthesis gas conversion reactor (e.g., Fischer-Tropsch reactor). The catalyst illustrated in FIG. 8 is in the form of a fixed bed of particulate solids. The catalyst illustrated in FIG. 9 has a flow-by structure design. The catalyst illustrated in FIG. 10 has a flow-through structure.

The catalyst may be in the form of a fixed bed of particulate solids (as shown in FIG. 8). Referring to FIG. 8, the catalyst 400, which is in the form of a bed of particulate solids, is contained in process microchannel 402. Reactants enter the fixed bed as indicated by arrow 404, undergo reaction, and product flows out of the fixed bed as indicated by arrow 406.

The catalyst may be supported on a catalyst support structure such as a foam, felt, wad or a combination thereof. The catalyst support structure may comprise a fin assembly or corrugated inserts suitable for insertion into slots in the microchannel reactor.

The term "foam" is used herein to refer to a structure with continuous walls defining pores throughout the structure. The term "felt" is used herein to refer to a structure of fibers with interstitial spaces therebetween. The term "wad" is used herein to refer to a structure of tangled strands, like steel wool. The catalyst may be supported on a honeycomb structure. The catalyst may be supported on a flow-by support structure such as a felt with an adjacent gap, a foam with an adjacent gap, a fin structure with gaps, a washcoat on any inserted substrate, or a gauze that is parallel to the flow direction with a corresponding gap for flow.

Figure 9:
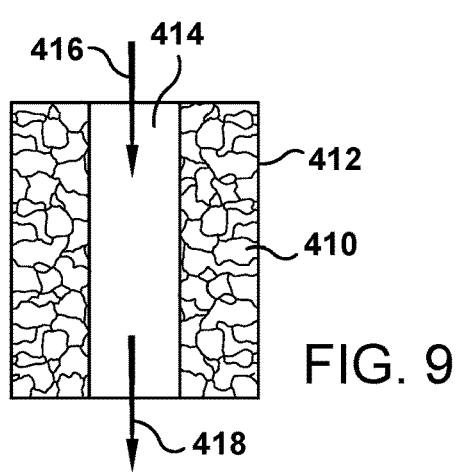

An example of a flow-by structure is illustrated in FIG. 9. In FIG. 9, the catalyst 410 is contained within process microchannel 412. An open passage way 414 permits the flow of fluid through the process microchannel 412 as indicated by arrows 416 and 418. The reactants contact the catalyst and undergo reaction to form product.

Figure 10:
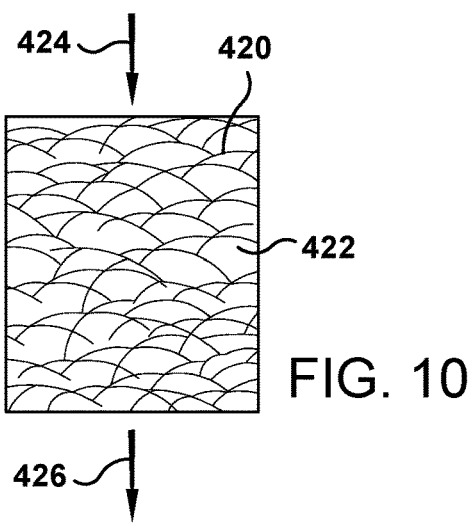

The catalyst may be supported on a flow-through support structure such as a foam, wad, pellet, powder, or gauze. An example of a flow-through structure is illustrated in FIG. 10. In FIG. 10, the flow-through catalyst 420 is contained within process microchannel 422, the reactants flow through the catalyst 420 as indicated by arrow 424, and undergo reaction to form the product 426.

The support structure for a flow-through catalyst may be formed from a material comprising silica gel, foamed copper, sintered stainless steel fiber, steel wool, alumina, or a combination of two or more thereof. The support structure may be made of a heat conducting material, such as a metal, to enhance the transfer of heat to or from the catalyst.

Figure 11:
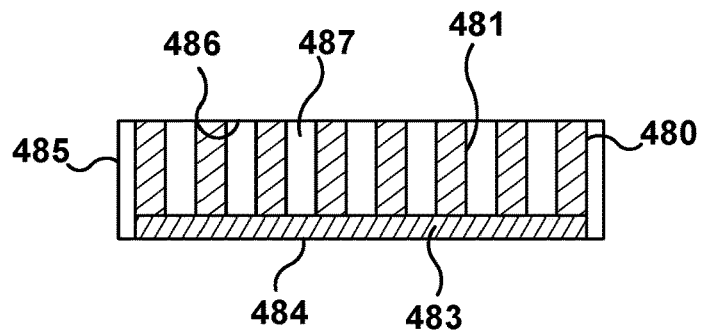
Figure 12:
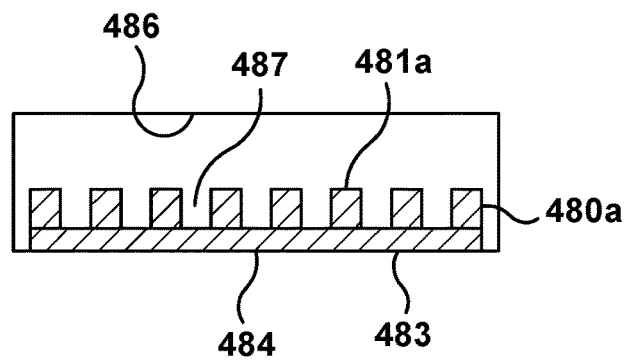
Figure 13:
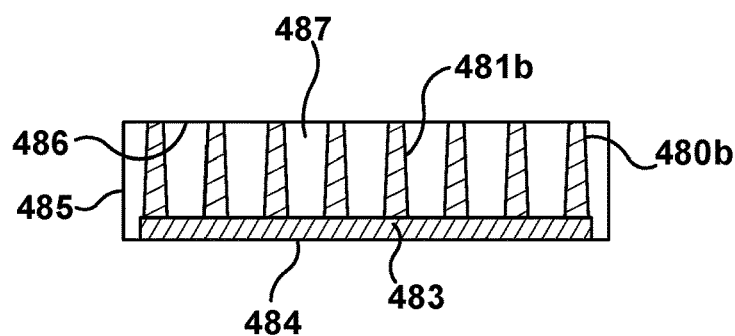

The catalyst may be supported on a fin assembly comprising one or more fins positioned within the process microchannels. Examples are illustrated in FIGS. 11-13. Referring to FIG. 11, fin assembly 480 includes fins 481 which are mounted on fin support 483 which overlies base wall 484 of process microchannel 485. The fins 481 project from the fin support 483 into the interior of the process microchannel 485. The fins 481 may extend to and contact the interior surface of upper wall 486 of process microchannel 485. Fin channels 487 between the fins 481 provide passage ways for reactant and product to flow through the process microchannel 485 parallel to its length. Each of the fins 481 has an exterior surface on each of its sides. The exterior surface provides a support base for the catalyst. The reactants may flow through the fin channels 487, contact the catalyst supported on the exterior surface of the fins 481, and react to form product. The fin assembly 480a illustrated in FIG. 12 is similar to the fin assembly 480 illustrated in FIG. 11 except that the fins 481a do not extend all the way to the interior surface of the upper wall 486 of the microchannel 485. The fin assembly 480b illustrated in FIG. 13 is similar to the fin assembly 480 illustrated in FIG. 11 except that the fins 481b in the fin assembly 280b have cross sectional shapes in the form of trapezoids. Each of the fins may have a height ranging from about 0.02 mm up to the height of the process microchannel 485, or from about 0.02 to about 10 mm, or from about 0.02 to about 5 mm, or from about 0.02 to about 2 mm. The width of each fin may range from about 0.02 to about 5 mm, or from about 0.02 to about 2 mm, or about 0.02 to about 1 mm. The length of each fin may be of any length up to the length of the process microchannel 485, or up to about 3 m, or about 0.03 to about 3 m, or about 0.03 to about 2.5 m, or about 0.03 to about 2 m. The gap between each of the fins may be of any value and may range from about 0.02 to about 5 mm, or from about 0.02 to about 2 mm, or from about 0.02 to about 1 mm. The number of fins in the process microchannel 485 may range from about 1 to about 50 fins per centimeter of width of the process microchannel 285, or from about 1 to about 30 fins per centimeter, or from about 1 to about 10 fins per centimeter, or from about 1 to about 5 fins per centimeter, or from about 1 to about 3 fins per centimeter. Each of the fins may have a cross-section in the form of a rectangle or square as illustrated in FIG. 11 or 12, or a trapezoid as illustrated in FIG. 13. When viewed along its length, each fin may be straight, tapered or have a serpentine configuration. The fin assembly may be made of any material that provides sufficient strength, dimensional stability and heat transfer characteristics to permit operation for which the process microchannel is intended. These materials include: steel (e.g., stainless steel, carbon steel, and the like); aluminum; titanium; nickel; platinum; rhodium; copper; chromium; alloys of any of the foregoing metals; monel; inconel; brass; polymers (e.g., thermoset resins); ceramics; glass; quartz; silicon; or a combination of two or more thereof. The fin assembly may be made of an $Al_2O_3$ or a $Cr_2O_3$ forming material wherein a layer of $Al_2O_3$ or a $Cr_2O_3$ forms on the surface of the fin assembly when the fin assembly is heat treated in air. The fin assembly may be made of an alloy comprising Fe, Cr, Al and Y, or an alloy comprising Ni, Cr and Fe.

Figure 14:
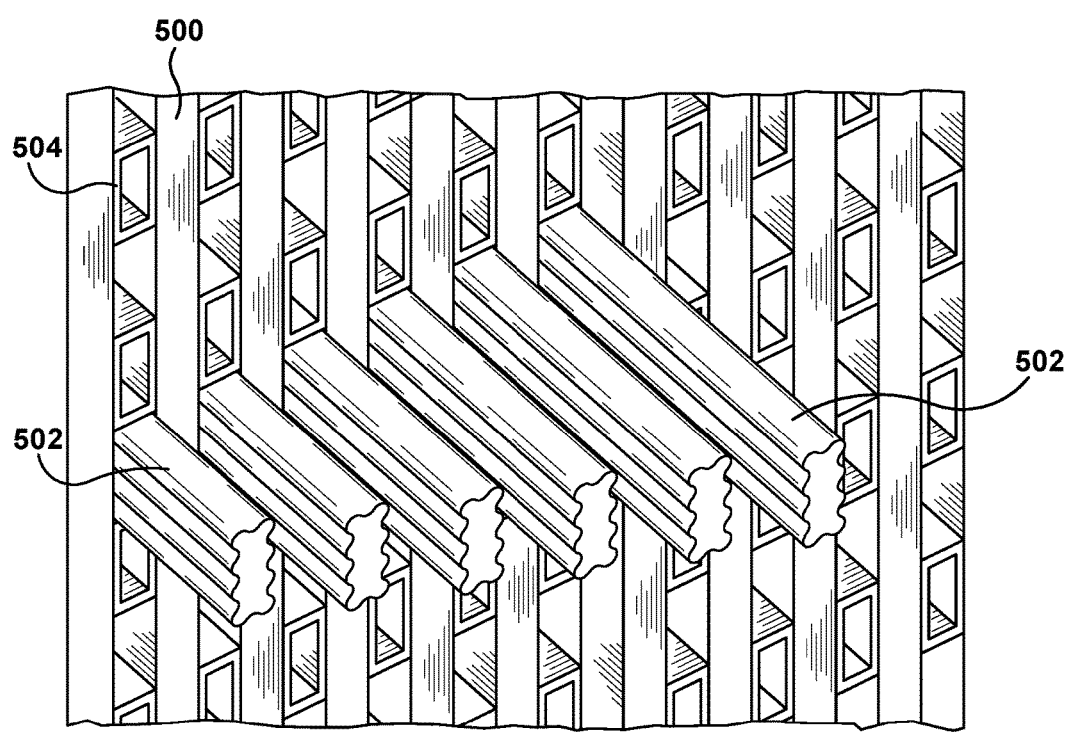
FIG. 14 is a schematic illustration of a synthesis gas conversion reactor (e.g., Fischer-Tropsch reactor) employing catalyst inserts in the form of corrugated structures.

The catalyst may be supported on one or more corrugated inserts positioned in slots within the microchannel reactor. This is illustrated in FIG. 14 wherein microchannel reactor 500 includes corrugated inserts 502 inserted in slots 504. The slots 504 may comprise microchannels, and have the dimensions indicated above as being microchannels. Alternatively, the slots 504 may have dimensions that would make them larger than microchannels. The process microchannels of the microchannel reactor may comprise the slots 504, or may be positioned within the corrugated inserts 502 and/or formed by openings between the interior sidewalls of the slots 504 and the inserts 502. Each of the corrugated inserts 502 may have a height ranging from about 0.02 mm up to the height of the slot 504, or from about 0.02 to about 10 mm, or from about 0.02 to about 5 mm, or from about 0.02 to about 2 mm. Each of the corrugated inserts 502 may have a width ranging from about 0.02 mm up to the width of the slot 504, or from about 0.02 to about 10 mm, or from about 0.02 to about 5 mm, or from about 0.02 to about 2 mm. The length of each corrugated insert may be of any length up to the length of the slot 504, or up to about 3 m, or about 0.03 to about 3 m, or about 0.03 to about 2 m, or about 0.03 to about 1 m. The corrugated inserts 502 may be made of any material that provides sufficient strength, dimensional stability and heat transfer characteristics to permit operation for which the microchannel reactor is intended. These materials include: steel (e.g., stainless steel, carbon steel, and the like); aluminum; titanium; nickel; platinum; rhodium; copper; chromium; alloys of any of the foregoing metals; monel; inconel; brass; polymers (e.g., thermoset resins); ceramics; glass; quartz; silicon; or a combination of two or more thereof. The corrugated inserts 502 may be made of an alloy that forms a layer of $Al_2O_3$ or $Cr_2O_3$ on the surface of the inserts when heat treated in air. The corrugated inserts 502 may be made of an alloy comprising Fe, Cr, Al and Y, or an alloy comprising Ni, Cr and Fe.

The catalyst may be directly washcoated or grown from solution on the interior walls of the process microchannels and/or on one or more of the above-described catalyst support structures. The catalyst may be in the form of a single piece of porous contiguous material, or a plurality of pieces in physical contact. The catalyst may comprise a contiguous material and have a contiguous porosity such that molecules can diffuse through the catalyst. In this embodiment, the fluids may flow through the catalyst rather than around it. The cross-sectional area of the catalyst may occupy from about 1 to about 99%, or about 10 to about 95% of the cross-sectional area of the process microchannels.

The catalyst may comprise a support, an interfacial layer on the support, and a catalyst material on or mixed with the interfacial layer. The support may comprise one or more of the above-described foams, felts, wads, fin structures, or corrugated inserts. The interfacial layer may be solution deposited on the support or it may be deposited by chemical vapor deposition or physical vapor deposition. The catalyst may comprise the support, a buffer layer, an interfacial layer, and the catalyst material. The support may be porous. Any of the foregoing layers may be continuous or discontinuous as in the form of spots or dots, or in the form of a layer with gaps or holes. The support may have a porosity of at least about 5% as measured by mercury porosimetry and an average pore size (sum of pore diameters divided by number of pores) of about 1 to about 2000 microns, or from about 1 to about 1000 microns. The support may be a porous ceramic or a metal foam. Other supports that may be used may include carbides, nitrides, and composite materials. The support may have a porosity of about 30% to about 99%, or about 60% to about 98%. The support may be in the form of a foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the support and the interfacial layers, and in one embodiment has a coefficient of thermal expansion that is intermediate the thermal expansion coefficients of the porous support and the interfacial layer. The buffer layer may be a metal oxide or metal carbide. The buffer layer may comprise $Al_2O_3$, $TiO_2$, $SiO_2$, $ZrO_2$, or combination thereof. The $Al_2O_3$ may be $\alpha$-$Al_2O_3$, $\gamma$-$Al_2O_3$ or a combination thereof. The buffer layer may comprise an oxide layer (e.g. $Al_2O_3$ or $Cr_2O_3$) formed by heat treating the support in air. The buffer layer may be formed of two or more compositionally different sublayers. For example, when the porous support is metal, for example a stainless steel foam, a buffer layer formed of two compositionally different sub-layers may be used. The first sublayer (in contact with the porous support) may be $TiO_2$. The second sublayer may be $\alpha$-$Al_2O_3$ which is placed upon the $TiO_2$. In one embodiment, the $\alpha$-$Al_2O_3$ sublayer is a dense layer that provides protection of the underlying metal surface. A less dense, high surface area interfacial layer such as alumina may then be deposited as support for a catalytically active layer.

The support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 µm, or about 0.05 to about 5 µm.

In an embodiment adequate adhesion and chemical stability may be obtained without a buffer layer. In this embodiment the buffer layer may be omitted.

The interfacial layer may comprise nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may comprise a metal oxide. Examples of metal oxides that may be used include $\alpha$-$Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. The interfacial layer may be used in combination with a catalytically active layer. The catalyst may be mixed with the interfacial layer. The interfacial layer may also be formed of two or more compositionally different sublayers. The interfacial layer may have a thickness that is less than one half of the average pore size of the porous support. The interfacial layer thickness may range from about 0.5 to about 100 µm, and in one embodiment from about 1 to about 50 microns. The interfacial layer may be either crystalline or amorphous. The interfacial layer may have a BET surface area of at least about 1 $m^2/g$.

The catalyst may be deposited on the interfacial layer. Alternatively, the catalyst may be simultaneously deposited with the interfacial layer. The catalyst layer may be intimately dispersed on the interfacial layer. That the catalyst layer is "dispersed on" or "deposited on" the interfacial layer includes the conventional understanding that microscopic catalyst particles are dispersed: on the support layer (i.e., interfacial layer) surface, in crevices in the support layer, and in open pores in the support layer.

The catalyst may be in the form of a bed of particulates. The catalytic bed of particulate solids may be graded in composition or graded with a thermally conductive inert material. The thermally conductive inert material may be interspersed with the active catalyst. Examples of thermally conductive inert materials that may be used include diamond powder, silicon carbide, aluminum, alumina, copper, graphite, and the like. The catalyst bed fraction may range from about 100% by weight active catalyst to less than about 50% by weight active catalyst. The catalyst bed fraction may range from about 10% to about 90% by weight active catalyst, and in one embodiment from about 25% to about 75% by weight. In an alternate embodiment the thermally conductive inert material may be deployed at the center of the catalyst or within the catalyst particles. The active catalyst may be deposited on the outside, inside or intermittent within a composite structure that includes the thermally conductive inert. The resultant catalyst composite structure may have an effective thermal conductivity when placed in a process microchannel or combustion channel that is at least about 0.3 W/m/K, and in one embodiment at least about 1 W/m/K, and in one embodiment at least about 2 W/m/K.

The catalyst bed may be graded only locally within the process microchannel. For example, a process microchannel may contain a catalyst bed with a first reaction zone and a second reaction zone. The top or bottom (or front or back) of the catalyst bed may be graded in composition whereby a more or less active catalyst is employed in all or part of the first or second reaction zone. The composition that is reduced in one reaction zone may generate less heat per unit volume and thus reduce the hot spot and potential for the production of undesirable by-products, such as methane in a Fischer-Tropsch reaction. The catalyst may be graded with an inert material in the first and/or second reaction zone, in full or in part. The first reaction zone may contain a first composition of catalyst or inert material, while the second reaction zone may contain a second composition of catalyst or inert material.

Different particle sizes may be used in different axial regions of the process microchannels to provide for graded catalyst beds. For example, very small particles may be used in a first reaction zone while larger particles may be used in a second reaction zone. The average particle diameters may be less than half the height or gap of the process microchannels. The very small particles may be less than one-fourth of the process microchannel height or gap. Larger particles may cause lower pressure drops per unit length of the process microchannels and may also reduce the catalyst effectiveness. The effective thermal conductivity of a catalyst bed may be lower for larger size particles. Smaller particles may be used in regions where improved heat transfer is sought throughout the catalyst bed or alternatively larger particles may be used to reduce the local rate of heat generation.

Relatively short contact times, high selectivity to the desired product and relatively low rates of deactivation of the catalyst may be achieved by limiting the diffusion path required for the catalyst. This may be achieved when the catalyst is in the form of a thin layer on an engineered support such as a metallic foam or on the wall of the process microchannel. This may allow for increased space velocities. The thin layer of catalyst may be produced using chemical vapor deposition. This thin layer may have a thickness in the range up to about 1 micron, and in one embodiment in the range from about 0.1 to about 1 micron, and in one embodiment in the range from about 0.1 to about 0.5 micron, and in one embodiment about 0.25 micron. These thin layers may reduce the time the reactants are within the active catalyst structure by reducing the diffusional path. This may decrease the time the reactants spend in the active portion of the catalyst. The result may be increased selectivity to the product and reduced unwanted by-products. An advantage of this mode of catalyst deployment may be that, unlike conventional catalysts in which the active portion of the catalyst may be bound up in an inert low thermal conductivity binder, the active catalyst film may be in intimate contact with either an engineered structure or a wall of the process microchannel. This may leverage high heat transfer rates attainable in the microchannel reactor and allow for close control of temperature. This may result in the ability to operate at increased temperature (faster kinetics) without promoting the formation of undesired by-products, thus producing higher productivity and yield and prolonging catalyst life.

The configuration of the microchannel reactor may be tailored to match the reaction kinetics. Near the entrance or top of a first reaction zone of a process microchannel, the microchannel height or gap may be smaller than in a second reaction zone near the exit or bottom of the process microchannel. Alternatively, the reaction zones may be smaller than half the process microchannel length. For example, a first process microchannel height or gap may be used for the first 25%, 50%, 75%, or 90% of the length of the process microchannel for a first reaction zone, while a larger second height or gap may be used in a second reaction zone downstream from the first reaction zone. This configuration may be suitable for conducting Fischer-Tropsch reactions. Other gradations in the process microchannel height or gap may be used. For example, a first height or gap may be used near the entrance of the microchannel to provide a first reaction zone, a second height or gap downstream from the first reaction zone may be used to provide a second reaction zone, and a third height or gap may be used to provide a third reaction zone near the exit of the microchannel. The first and third heights or gaps may be the same or different. The first and third heights or gaps may be larger or smaller than the second height or gap. The third height or gap may be smaller or larger than the second height or gap. The second height or gap may be larger or smaller than the third height or gap.

The catalyst may be rejuvenated or regenerated by flowing a rejuvinating or regenerating fluid through the process microchannels in contact with the catalyst. The rejuvenating or regenerating fluid may comprise hydrogen or a diluted hydrogen stream. The diluent may comprise nitrogen, argon, helium, methane, carbon dioxide, steam, or a mixture of two or more thereof. The temperature of the rejuvenating or regenerating fluid may be from about 50 to about 400° C., and in one embodiment about 200 to about 350° C. The pressure within the channels during this rejuvenation or regeneration step may range from about 1 to about 40 atmospheres, and in one embodiment about 1 to about 20 atmospheres, and in one embodiment about 1 to about 5 atmospheres. To complete the regeneration of the catalyst, after the rejuvenating or regenerating fluid flows in contact with the catalyst, the catalyst may be oxidized and then reduced. The residence time for the rejuvenating or regenerating fluid in the channels may range from about 0.01 to about 1000 seconds, and in one embodiment about 0.1 second to about 100 seconds. The microchannel reactor may comprise a reactant header, a product footer and a plurality of process microchannels connecting to the header and footer. The rejuvenating or regenerating fluid may flow from the header through the process microchannels to the footer. Alternatively, the rejuvenating or the regenerating fluid may flow from the footer through the process microchannels to the header.

The catalyst may be rejuvenated by removing wax and other hydrocarbons from the catalyst. The catalyst may be regenerated by removing wax and other hydrocarbons from the catalyst (typically by stripping with $H_2$), oxidizing the catalyst with air or other $O_2$ containing gas at an elevated temperature, re-reducing the catalyst, and then activating the catalyst.

A synthesis gas conversion production run (e.g., Fischer-Tropsch production run) will typically be conducted over an extended period of time, for example, at least about 300 hours, or at least about 3000 hours, or at least about 12,000 hours, or at least about 15,000 hours. The reactivity of the catalyst will typically decline over time and to make up for this decline the temperature of the reaction is usually increased in order to maintain a constant level of production. However, at some point in time the production run will be stopped, either purposely or accidentally, and the problem addressed with this invention relates to providing a rapid restart of the production run. With this invention, the production run may be restarted within a period of, for example, up to about 3 hours, or up to about 2 hours, or up to about 1 hour, or up to about 0.1 hour from the time the flow of synthesis gas into the reactor is restarted.

In an embodiment, this invention relates to a synthesis gas conversion process (e.g., Fischer-Tropsch process) which comprises flowing synthesis gas into a reactor in contact with a Fischer-Tropsch catalyst at a reaction temperature and pressure to produce a Fischer-Tropsch product. The flow of synthesis gas entering the reactor may be stopped for up to about 48 hours, or up to about 36 hours, or up to about 24 hours, or up to about 12 hours, or up to about 3 hours, or up to about 1 hour. This may be referred to as a bottled period. The Fischer-Tropsch process may then be restarted by a method comprising: restoring the pressure within the reactor at the reaction pressure, maintaining the temperature within the reactor between the coolant temperature and the reaction temperature with the coolant temperature set close (e.g., within about 15° C., or about 10° C., or about 5° C., or about 1° C. below) to the original reaction temperature; and restarting the flow of synthesis gas into the reactor, and the flow of effluent out of the reactor. In this embodiment the return to full production may be almost instantaneous. The reaction temperature may be controlled with a coolant flowing in a heat exchanger in thermal contact with the reactor. The bottling may be followed by purging with hydrogen, nitrogen or desulfurized natural gas and reintroduction of synthesis gas into the reactor.

In an embodiment, the flow of synthesis gas entering the reactor is stopped. The Fischer-Tropsch process may be restarted by a method comprising: restoring the pressure within the reactor at the reaction pressure, and restarting the flow of synthesis gas into the reactor. The reactor temperature may then be ramped up to the original operating temperature, prior to the stop, within a period of time in the range from 0.1 to about 24 hours, or about 1 to about 3 hours, by heating the reactor at a rate of up to about 5° C. per hour, or up to about 10° C. per hour, or up to about 15° C. per hour, or up to about 30° C. per hour, or up to about 60° C. per hour. The reaction temperature may be controlled with a heat exchange fluid flowing in a heat exchanger in thermal contact with the reactor In an embodiment, the flow of synthesis gas entering the reactor is stopped. The Fischer-Tropsch process may be restarted by a method comprising: flowing hydrogen into the reactor to purge the reactor of reactants and effluent, holding the reactor in a hydrogen environment for a period of time of up to about 48 hours, or up to about 36 hours, or up to about 24 hours, or up to about 12 hours, and then restarting the flow of synthesis gas into the reactor. The reaction temperature may be in the range from about 150° C. to about 300° C., and during the step of flowing hydrogen into the reactor the temperature within the reactor may be increased to a temperature above the reaction temperature, for example, up to about 350° C., or up to about 400° C. This may rejuvenate the catalyst. The reaction temperature may be controlled with a heat exchange fluid flowing in a heat exchanger in thermal contact with the reactor.

In an embodiment, the flow of synthesis gas into the reactor is stopped. The Fischer-Tropsch process may be restarted by a method comprising: flowing desulfurized natural gas into the reactor to purge the reactor of reactants and effluent, holding the reactor in a natural gas environment for a period of time of up to about 48 hours, or up to about 36 hours, or up to about 24 hours, or up to about 12 hours, or up to about 6 hours, or up to about 3 hours, or up to about 1 hour and then restarting the flow of synthesis gas into the reactor and the flow of effluent out of the reactor.

In an embodiment, the flow of synthesis gas into the reactor is stopped. The Fischer-Tropsch process may be restarted by a method comprising: maintaining the reactor at the pre-stop operating temperature for a period of time of up to about 48 hours, or up to about 36 hours, or up to about 24 hours, or up to about 12 hours, or up to about 6 hours, or up to about 3 hours, or up to about 1 hour; restoring the pressure to the operating pressure (if needed); and flowing hydrogen, nitrogen, or desulfurized natural gas into the reactor to purge the reactor of reactants and effluent; holding the reactor in a purge gas environment for a period of time of up to about 48 hours, or up to about 36 hours, or up to about 24 hours, or up to about 12 hours, or up to about 6 hours, or up to about 3 hours, or up to about 1 hour; and then restarting the flow of synthesis gas into the reactor and the flow of effluent out of the reactor. In an embodiment, the purge gas is introduced into the reactor as close to the catalyst bed as possible to minimize the additional fresh reactant supply in contact with the catalyst.

In an embodiment, the flow of synthesis gas entering the reactor is stopped. The Fischer-Tropsch process may be restarted by a method comprising: maintaining the reactor at the pre-stop operating temperature for a period of up to about 48 hours, or up to about 36 hours, or up to about 24 hours, or up to about 12 hours, or up to about 6 hours, or up to about 3 hours, or up to about 1 hour; restoring the pressure to the operating pressure (if needed); and flowing hydrogen, nitrogen, or desulfurized natural gas into the reactor to purge the reactor of reactants and effluent; holding the reactor in a purge gas environment for a period of time of up to about 48 hours, or up to about 36 hours, or up to about 24 hours, or up to about 12 hours, or up to about 6 hours, or up to about 3 hours, or up to about 1 hour; cooling the reactor to a temperature lower than the operating temperature; and then restarting the flow of synthesis gas into the reactor and the flow of effluent out of the reactor. The reactor temperature may then be ramped up to the operating temperature used prior to the stop within a period of time of up to about 24 hours, or up to about 12 hours, or up to about 6 hours, or up to about 3 hours, or up to about 1 hour, or up to about 0.1 hour, by heating the reactor at a rate of up to about 5° C. per hour, or up to about 10° C. per hour, or up to about 15° C. per hour, or up to about 30° C. per hour, or up to about 60° C. per hour. Optionally, purging at a pressure less than operating pressure may be conducted, with the operating pressure restored when introducing synthesis gas.

In an embodiment, the flow of synthesis gas into the reactor is stopped. The Fischer-Tropsch process may be restarted by a method comprising: maintaining the reactor at the pre-stop operating temperature for a period of time of up to about 48 hours, or up to about 36 hours, or up to about 24 hours, or up to about 12 hours, or up to about 6 hours, or up to about 3 hours, or up to about 1 hour; depressurizing the reactor to a pressure (lower than the operating pressure) of up to about 20 atmospheres, or up to about 10 atmospheres, or up to about 5 atmospheres; and flowing hydrogen, nitrogen, or desulfurized natural gas into the reactor to purge the reactor of reactants and effluent; holding the reactor in a purge gas environment for a period of time of up to about 48 hours, or up to about 36 hours, or up to about 24 hours, or up to about 12 hours, or up to about 6 hours, or up to about 3 hours, or up to about 1 hour; restarting the flow of synthesis gas into the reactor and effluent out of the reactor; and pressurizing the reactor to the target operating pressure. If the reactor temperature is reduced to that below the pre-stop operating temperature, the reactor temperature may then be ramped up to the operating temperature prior to the stop within a period of time of up to about 48 hours, or up to about 36 hours, or up to about 24 hours, or up to about 12 hours, or up to about 6 hours, or up to about 3 hours, or up to about 1 hour, or up to about 0.1 hour, by heating at a rate of up to about 15° C. per hour, or up to about 30° C. per hour, or up to about 60° C. per hour.

In an embodiment, the flow of synthesis gas entering the reactor is stopped. The Fischer-Tropsch process may be restarted by a method comprising: restarting the flow of synthesis gas into the reactor and the flow of effluent out of the reactor, the temperature of the synthesis gas flowing into the reactor being within about 10° C. of the reaction temperature in the reactor, or within about 5° C. of the reaction temperature. The reaction temperature may be controlled with a heat exchange fluid flowing in a heat exchanger in thermal contact with the reactor, and during the step of restarting the flow of synthesis gas into the reactor and the flow of effluent out of the reactor, the temperature of the heat exchange fluid in the heat exchanger may be less than about 10° C., or less than about 5° C., of the reaction temperature in the reactor. In this embodiment, the Fischer-Tropsch catalyst may comprise a wet catalyst.

In an embodiment, the flow of synthesis gas into the reactor is stopped. The Fischer-Tropsch process may be restarted by a method comprising: rejuvenating the catalyst in a hydrogen environment, or regenerating the catalyst by de-waxing the catalyst followed by oxidation and reduction of the catalyst; and restarting the flow of synthesis gas into the reactor and the flow of effluent out of the reactor, the temperature of the synthesis gas flowing into the reactor being at the reaction temperature. The reaction temperature in the reactor may be controlled with a heat exchange fluid flowing in a heat exchanger in thermal contact with the reactor, and during the restarting of the flow of synthesis gas into the reactor, the temperature of the heat exchange fluid in the heat exchanger may be lower than the reaction temperature in the reactor, for example, up to about 10° C. lower, or up to about 5° C. lower, than the reaction temperature in the reactor.

In an embodiment, the flow of synthesis gas into the reactor is stopped. The catalyst in the reactor is a wet catalyst. The Fischer-Tropsch process may be restarted by a method comprising: flowing hydrogen at a temperature of up to about 400° C. to regenerate the catalyst, followed by an oxidation treatment involving flowing an oxygen containing gas mixture, such as air (21% $O_2$), into the reactor in contact with the Fischer-Tropsch catalyst at a temperature from about 70° C. to about 350° C., or from about 250° C. to about 300° C. for a period of time in the range from about 1 to about 12 hours. This may be followed by a catalyst reduction treatment involving flowing hydrogen at a temperature of up to about 400° C. in contact with the catalyst to regenerate the Fischer-Tropsch catalyst. The flow of synthesis gas into the reactor in contact with the regenerated catalyst and the flow of effluent out of the reactor may then be started. The reaction temperature in the reactor may be controlled with a heat exchange fluid flowing in a heat exchanger in thermal contact with the reactor, and during the restarting of the flow of synthesis gas into the reactor, the temperature of the heat exchange fluid in the heat exchanger may be lower than the reaction temperature in the reactor, for example, up to about 10° C. lower, or up to about 5° C. lower, than the reaction temperature in the reactor.

In an embodiment, the flow of synthesis gas entering the reactor is stopped. The Fischer-Tropsch process may be restarted by a method comprising: selectively infusing hydrogen into the reactor without the purging of the synthesis gas in contact with the catalyst and/or selectively defusing (removing) water vapor from the process gas mixture in the reactor and then restarting the flow of synthesis gas into the reactor and the flow of effluent out of the reactor and adjusting the process pressures and temperatures to the pre-stoppage levels. Conditions should be avoided which would cause the condensation of liquid water in the reactor at the reactor temperature and pressure. For example, the partial pressure of water in the mixture should not exceed the saturation vapor pressure of water (at reactor temperature and pressure) even if all CO present in the mixture is converted, forming a mole of water for every mole of CO initially present in the feed.

In an embodiment, the flow of synthesis gas entering the reactor is stopped and the flow of effluent exiting the reactor is stopped. The process (e.g., Fischer-Tropsch process) may be restarted by a method comprising: flowing hydrogen into the reactor to purge the reactor of reactants and effluent at a volumetric flow rate which is equal to or higher than the volumetric flow rate of synthesis gas prior to the synthesis gas flow stoppage. Maintaining such a flow rate until the reactor has been purged helps prevent high conversion products from forming which could negatively affect apparent catalyst activity. The flow of synthesis gas into the reactor and the flow of effluent out of the reactor is then restarted.

In an embodiment, the flow of synthesis gas entering the reactor is stopped and the flow of effluent exiting the reactor is stopped. The process (e.g., Fischer-Tropsch process) may be restarted by a method comprising: flowing nitrogen gas into the reactor to purge the reactor of reactants and effluent at a volumetric flow rate which is equal to or higher than the volumetric flow rate of synthesis gas prior to the synthesis gas flow stoppage. The flow of synthesis gas into the reactor and the flow of effluent out of the reactor is then restarted.

In an embodiment, the flow of synthesis gas entering the reactor is stopped and the flow of effluent exiting the reactor is stopped. The process (e.g., Fischer-Tropsch process) may be restarted by a method comprising: flowing natural gas (e.g., desulfurized natural gas) into the reactor to purge the reactor of reactants and effluent at a volumetric flow rate which is equal to or higher than the volumetric flow rate of synthesis gas prior to the synthesis gas flow stoppage. The flow of synthesis gas into the reactor and the flow of effluent out of the reactor is then restarted.

In an embodiment, the flow of synthesis gas entering the reactor is stopped. This is followed by flowing hydrogen at a temperature lower than the temperature of the reactor into the reactor to purge the reactor of reactants and effluent. The flow of synthesis gas into the reactor is then restarted.

In an embodiment, the flow of synthesis gas entering the reactor is stopped. This is followed by flowing nitrogen gas at a temperature lower than the temperature of the reactor into the reactor to purge the reactor of reactants and effluent. The flow of synthesis gas into the reactor is then restarted.

In an embodiment, the flow of synthesis gas entering the reactor is stopped. This is followed by flowing natural gas (e.g., desulfurized natural gas) at a temperature lower than the temperature of the reactor into the reactor to purge the reactor of reactants and effluent. The flow of synthesis gas into the reactor is then restarted.

In an embodiment, the flow of synthesis gas entering the reactor is stopped and the flow of effluent exiting the reactor is stopped. This is followed by flowing hydrogen gas into the reactor to purge the reactor of reactants and effluent where the volume of purge gas used is equal to or higher than the volume of synthesis gas in the system between the locations for stopping the flow of synthesis gas into the reactor and the stopping the flow of effluent out of the reactor. This is followed by restarting the flow of synthesis gas into the reactor and the flow of effluent out of the reactor.

In an embodiment, the flow of synthesis gas entering the reactor is stopped and the flow of effluent exiting the reactor is stopped. This is followed by flowing nitrogen gas into the reactor to purge the reactor of reactants and effluent where the volume of purge gas used is equal to or higher than the volume of synthesis gas in the system between the locations for stopping the flow of synthesis gas into the reactor and stopping the flow of the effluent out of the reactor. This is followed by restarting the flow of synthesis gas into the reactor and the flow of effluent out of the reactor.

In an embodiment, the flow of synthesis gas entering the reactor is stopped and the flow of effluent exiting the reactor is stopped. This is followed by flowing natural gas (e.g., desulfurized natural gas) into the reactor to purge the reactor of reactants and effluent where the volume of purge gas used is equal to or higher than the volume of synthesis gas in the system between the locations for stopping the flow of synthesis gas into the reactor and stopping the flow of the effluent out of the reactor. This is followed by restarting the flow of synthesis gas into the reactor and the flow of effluent out of the reactor.

This invention relates to a method of operating a Fischer-Tropsch process wherein the process is conducted in a plant comprising a plurality of reaction trains. Each reaction train may comprise at least one Fischer-Tropsch reactor containing a Fischer-Tropsch catalyst, the reaction trains being connected to a common reactant feed stream comprising fresh synthesis gas, and the flow of synthesis gas into the Fischer-Tropsch reactor and the flow of effluent out of the Fischer-Tropsch reactor of one or more of the reaction trains is stopped, while the flow of synthesis gas into and the flow of effluent out of the remainder of the reaction trains in the plant is continued. The method comprises: (A) flowing the reactant feed stream at an overall process flow rate to the plurality of reaction trains in the plant; (B) dividing the reactant feed stream into a plurality of reactant substreams; (C) flowing each reactant substream through a separate reaction train to convert the reactants in the reactant substream to a Fischer-Tropsch product; (D) stopping the flow of a reactant substream to one or more of the reaction trains; and (E) continuing to flow the reactant feed stream to the remainder of reaction trains in the plant at the same overall process flow rate. During step (C) a mixture of fresh synthesis gas and a recycled tail gas may flow into the Fischer-Tropsch reactor of each reaction train. During step (E) the flow of recycled tail gas into the Fischer-Tropsch reactor of the one or more of the remainder of the reaction trains in the plant may be stopped or reduced in order to allow for maintaining the overall flow of fresh synthesis gas into the plant at a constant level.

This invention relates to a method of operating a Fischer-Tropsch process wherein the process is conducted in a plant comprising a plurality of reaction trains, each reaction train comprising at least one Fischer-Tropsch reactor containing a Fischer-Tropsch catalyst, the reaction trains being connected to a reactant feed stream comprising fresh synthesis gas, and the flow of synthesis gas into and the flow of effluent out of the Fischer-Tropsch reactor of one or more of the reaction trains is stopped, while the flow of synthesis gas into and the flow of effluent out of the Fischer-Tropsch reactor of the other reaction trains in the plant is continued. The method comprises: flowing the reactant feed stream to the plurality of reaction trains; dividing the reactant feed stream into a reactant substream for each reaction train; and flowing each reactant substream through a reaction train to convert the reactants in the reactant substream to a Fischer-Tropsch product. In an embodiment, the temperature of the Fischer-Tropsch product flowing out of one reaction train (as measured by the reactor process outlet or as measured by the reactor heat exchange fluid outlet temperature) of at least one reactor trains is within about 20° C. or about 10° C., or about 5° C., or about 2° C., or about 1° C., of the temperature of the product flowing out of another reaction train within the plant.

The Fischer-Tropsch product may be further processed to form a lubricating base oil or diesel fuel. For example, the product made in the microchannel reactor 110 may be hydrocracked and then subjected to distillation and/or catalytic isomerization to provide a lubricating base oil, diesel fuel, aviation fuel, and the like. The Fischer-Tropsch product may be hydroisomerized using the process disclosed in U.S. Pat. No. 6,103,099 or 6,180,575; hydrocracked and hydroisomerized using the process disclosed in U.S. Pat. No. 4,943,672 or 6,096,940; dewaxed using the process disclosed in U.S. Pat. No. 5,882,505; or hydroisomerized and dewaxed using the process disclosed in U.S. Pat. Nos. 6,013,171, 6,080,301 or 6,165,949. These patents are incorporated herein by reference for their disclosures of processes for treating Fischer-Tropsch synthesized hydrocarbons and the resulting products made from such processes.

The hydrocracking reaction may be conducted in a hydrocracking microchannel reactor and may involve a reaction between hydrogen and the Fischer-Tropsch product flowing from the microchannel reactor 200, or one or more hydrocarbons separated from the Fischer-Tropsch product (e.g., one or more liquid or wax Fischer-Tropsch hydrocarbons). The Fischer-Tropsch product may comprise one or more long chain hydrocarbons. The Fischer-Tropsch product may comprise a Fischer-Tropsch wax. In the hydrocracking process, a desired diesel fraction, for example, may be increased by cracking a $C_{23+}$ fraction to mid range carbon numbers of $C_{12}$ to $C_{22}$. A wax fraction produced from the Fischer-Tropsch microchannel reactor 200 may be fed to the hydrocracking microchannel reactor with excess hydrogen for a triple phase reaction. Under reaction conditions at elevated temperatures and pressures, a fraction of the liquid feed may convert to a gas phase, while the remaining liquid fraction may flow along the catalyst. In conventional hydrocracking systems, a liquid stream forms. The use of a microchannel reactor for the hydrocracking reaction enables unique advantages on a number of fronts. These may include kinetics, pressure drop, heat transfer, and mass transfer.

In an embodiment, the hydrogen, which is in the form of a gas, flows in the microchannel reactor, and the Fischer-Tropsch product, which is in the form of a liquid, flows into the gas in the microchannel reactor to form a hydrocracking reactant mixture. This flow pattern facilitates shearing of the interface between the reactants.

The operating temperature within the hydrocracking microchannel reactor may be in the range of about 200° C. to about 490° C., or about 250° C. to about 450° C., and the temperature of the Fischer-Tropsch synthesis product entering the hydrocracking microchannel reactor may be at a relatively low temperature in the range of about 150° C. to about 300° C., or about 150° C. to about 250° C. This relatively low temperature is useful in preventing coking or clogging in the hydrocarbon microchannel reactor.

The Fischer-Tropsch hydrocarbon products that may be hydrocracked in the hydrocracking microchannel reactor may comprise any hydrocarbon that may be hydrocracked. These may include hydrocarbons that contain one or more C—C bonds capable of being broken in a hydrocracking process. The Fischer-Tropsch product that may be hydrocracked may comprise a Fischer-Tropsch wax. The hydrocarbons that may be hydrocracked may include saturated aliphatic compounds (e.g., alkanes), unsaturated aliphatic compounds (e.g., alkenes, alkynes), hydrocarbyl (e.g., alkyl) substituted aromatic compounds, hydrocarbylene (e.g., alkylene) substituted aromatic compounds, and the like.

The feed composition for the hydrocracking microchannel reactor may include one or more diluent materials. Examples of such diluents may include non-reactive hydrocarbon diluents, and the like. The diluent concentration may be in the range from zero to about 99% by weight based on the weight of the Fischer-Tropsch product, or from zero to about 75% by weight, or from zero to about 50% by weight. The diluents may be used to reduce the viscosity of viscous liquid reactants. The viscosity of the feed composition in the hydrocracking microchannel reactor may be in the range from about 0.001 to about 1 centipoise, or from about 0.01 to about 1 centipoise, or from about 0.1 to about 1 centipoise.

The ratio of hydrogen to Fischer-Tropsch product in the feed composition entering the hydrocracking microchannel reactor may be in the range from about 10 to about 2000 standard cubic centimeters (sccm) of hydrogen per cubic centimeter (ccm) of Fischer-Tropsch product, or from about 100 to about 1800 sccm/ccm, or from about 350 to about 1200 sccm/ccm. The hydrogen feed may further comprise water, methane, carbon dioxide, carbon monoxide and/or nitrogen.

The $H_2$ in the hydrogen feed may be derived from another process such as a steam reforming process (product stream with $H_2/CO$ mole ratio of about 3), a partial oxidation process (product stream with $H_2/CO$ mole ration of about 2), an autothermal reforming process (product stream with $H_2/CO$ mole ratio of about 2.5), a $CO_2$ reforming process (product stream with $H_2/CO$ mole ratio of about 1), a coal gassification process (product stream with $H_2/CO$ mole ratio of about 1), and combinations thereof. With each of these feed streams the $H_2$ may be separated from the remaining ingredients using conventional techniques such as membranes or adsorption.

The hydrocracked Fischer-Tropsch product may comprise a middle distillate fraction boiling in the range of about 260-700° F. (127-371° C.). The term "middle distillate" is intended to include the diesel, jet fuel and kerosene boiling range fractions. The terms "kerosene" and "jet fuel" boiling range are intended to refer to a temperature range of 260-550° F. (127-288° C.) and "diesel" boiling range is intended to refer to hydrocarbon boiling points between about 260 to about 700° F. (127-371° C.). The hydrocracked Fischer-Tropsch product may comprise a gasoline or naphtha fraction. These may be considered to be the $C_5$ to 400° F. (204° C.) endpoint fractions.

Examples 1-5

A series of synthesis gas interruption tests reported below as Examples 1-5 are conducted using a Fischer-Tropsch microchannel reactor. The results are reported in Tables 1-5 and 7, and in the attached FIGS. 15-20.

The Fischer-Tropsch microchannel reactor has a process microchannel with a height of 1 mm, a width of 0.6 cm, and a length of 63.5 cm. A 1.9 cm long SiC bed is positioned in the process microchannel upstream of the catalyst. The catalyst is a supported cobalt catalyst in the form of a fixed bed of particulate solids. The catalyst bed has a length 61.6 cm. Two heat exchange or coolant channels of dimensions 0.2 cm×1.27 cm run parallel to the process channel along its entire length, one coolant channel on either side of the process microchannel. A hot oil (Marlotherm SH) flow is maintained in both the coolant channels, co-current to the direction of flow of synthesis gas in the process microchannel, using a Julabo pump at a minimum flow rate of 8 liters per minute (LPM). The reactor temperature is measured by a set of Omega K-type thermocouples inserted in thermowells in the metal webs between the process microchannel and coolant channels.

The packed apparent bed density (PABD) of the SiC and the catalyst is measured ex-situ by measuring the mass of SiC and catalyst filled in a Class-A 10 ml "to contain" graduated cylinder and densified using a Quantachrome Autotap set to 1500 taps. After installing a retention assembly at the reactor outlet, the catalyst is first loaded to a bed length of 61.6 cm followed by SiC to top off the process microchannel. The bed is densified. The PABD of the catalyst and SiC in the process microchannel is within about ±5% of the ex-situ measured PABD. This is followed by installation of a catalyst retention assembly at the reactor inlet.

The reactor is installed in a test stand and connections are provided for feeding synthesis gas into the process microchannel and flowing effluent out of the process microchannel. Similarly, connections are provided for feeding hot oil into and out of the heat exchange channels. The catalyst is activated using hydrogen with a gas hourly space velocity (GHSV) of 7000 hr$^{-1}$ based on the loaded volume of catalyst in the reactor. The temperature is ramped from ambient to an activation temperature of 350° C. After the completion of an activation hold, the reactor is cooled to a temperature of 150-170° C. and a synthesis gas feed is introduced to the reactor. The reactor pressure is adjusted to the target value and the temperature is ramped up to achieve the desired CO conversion. The reactor performance (CO conversion, $CH_4$ selectivity, etc) is monitored by measuring the tail gas flow and effluent composition from the reactor outlet.

Figure 21:
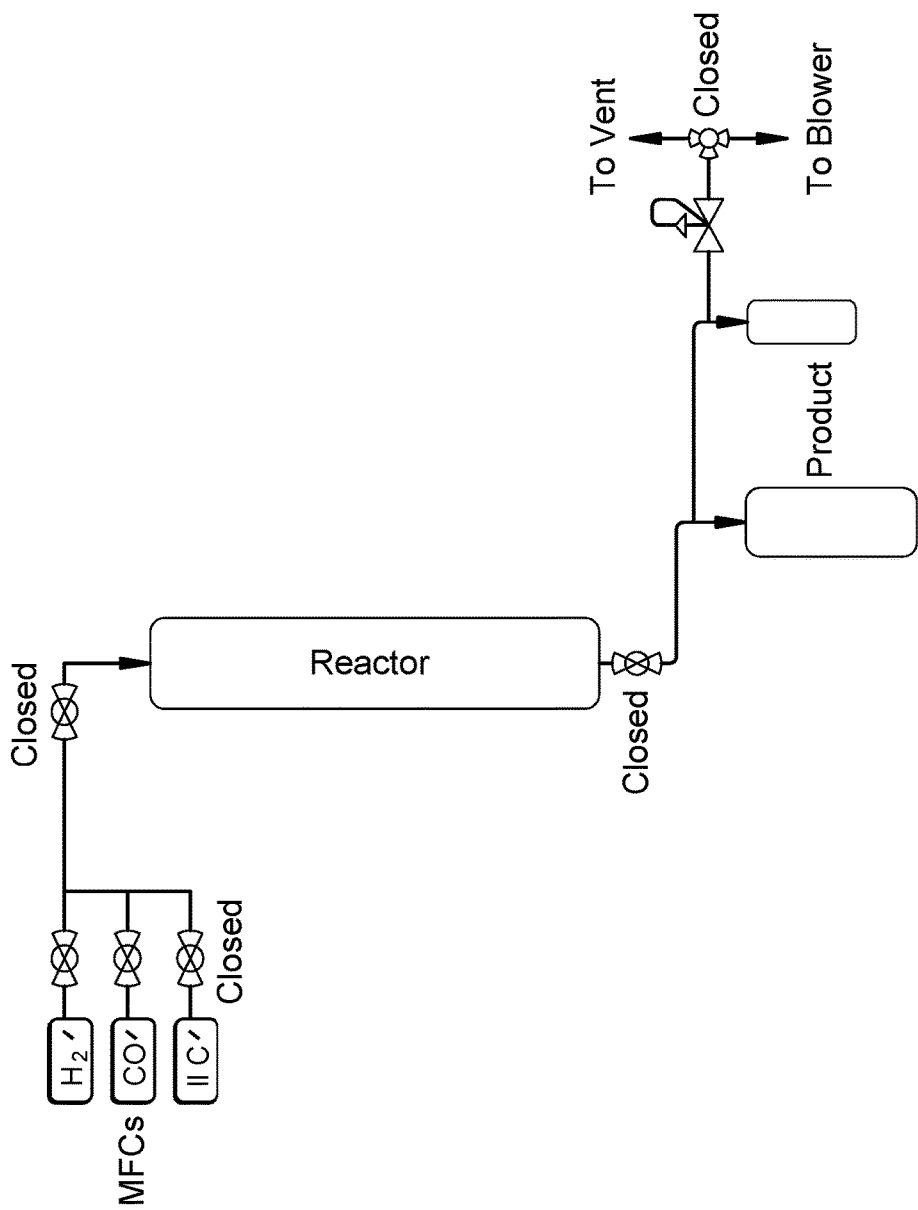
FIG. 21 is a flow sheet showing apparatus for conducting a synthesis gas conversion process which can be stopped and restarted.

The bottling procedure may be performed using the apparatus illustrated in FIG. 21. Referring to FIG. 21, before initiating the bottling sequence, the pressure related (PT) interlocks are disabled and the pressure control valve (PCV) is set in manual mode with output equal to the current operating value in automatic mode. The ball valves (BV) at the reactor outlet and reactor inlet are closed (in that sequence) to isolate the synthesis gas within the reactor. The three-way BV after the PCV is also closed to prevent depressurization of the product tanks. Finally, all gas flows to the reactor are turned off by closing the BVs after the mass flow controllers (MFCs) and then adjusting the MFC output to fully closed.

If depressurization is desired, the PCV output is set to the same value as it was prior to bottling the reactor. Then, the BV at the inlet of reactor is opened, the BV at the outlet of the reactor is opened, and the three-way BV after the PCV is opened (in that sequence). The PCV is set to ramp to desired rate to depressurize the reactor and system to the target pressure.

If purge is required, the mass flow controller (MFC) BV for the desired purge gas (e.g., hydrogen, natural gas, nitrogen) is opened and flows turned ON at the target flow rate and the gas is allowed to flow for the desired time. After the completion of the purge, the reactor is again bottled as described above.

If holding at temperature, no changes in reactor temperature setting are made. If cooling down, the reactor temperature is changed at the desired rate to the target value by setting a ramp rate for the average reactor temperature control.

The restart of operations from a bottled scenario can be achieved in the following manner: To unbottle the reactor, the inlet BV to the reactor is opened followed by the outlet BV to the reactor and the three-way BV after the PCV. Synthesis gas flow is restarted by setting the desired $N_2$, $H_2$, and CO flows, resulting in establishment of full flows within a few seconds. The reactor is then pressurized to the desired inlet pressure using the PCV. If needed, the reactor is heated to the target temperature by setting a ramp rate for the average reactor temperature control.

The reaction rate model for Fischer Tropsch synthesis on cobalt catalyst (Yates and Satterfield, 1991, referred to above) may be given by $$-R_{CO} = \frac{aP_O P_{H_2}}{(1+bP_{CO})^2}$$

where a and b are temperature-dependent constants; "a" representing a kinetic parameter and "b" an adsorption coefficient as shown below:

| Reactor Temperature (° C.) | $a\left(\dfrac{mmol}{min\ g_{cat} MPa^2}\right)$ | $b\left(\dfrac{1}{MPa}\right)$ |
|---|---|---|
| 240 | 75.76 | 11.61 |
| 220 | 53.11 | 22.26 |

Assuming:

$a = Ae^{E_3/RT}$ and $b = Be^{-H/RT}$

The kinetic rate equation parameters are estimated as, $a = 0.082505 e^{-27267/2.314T}$ in $\dfrac{\frac{mols}{s}}{gcat} / atm^2$ and $b = 1.259 \times 10^{-7} e^{68475/2.314T}$ in 1/atm.

Example 1

Figure 15:
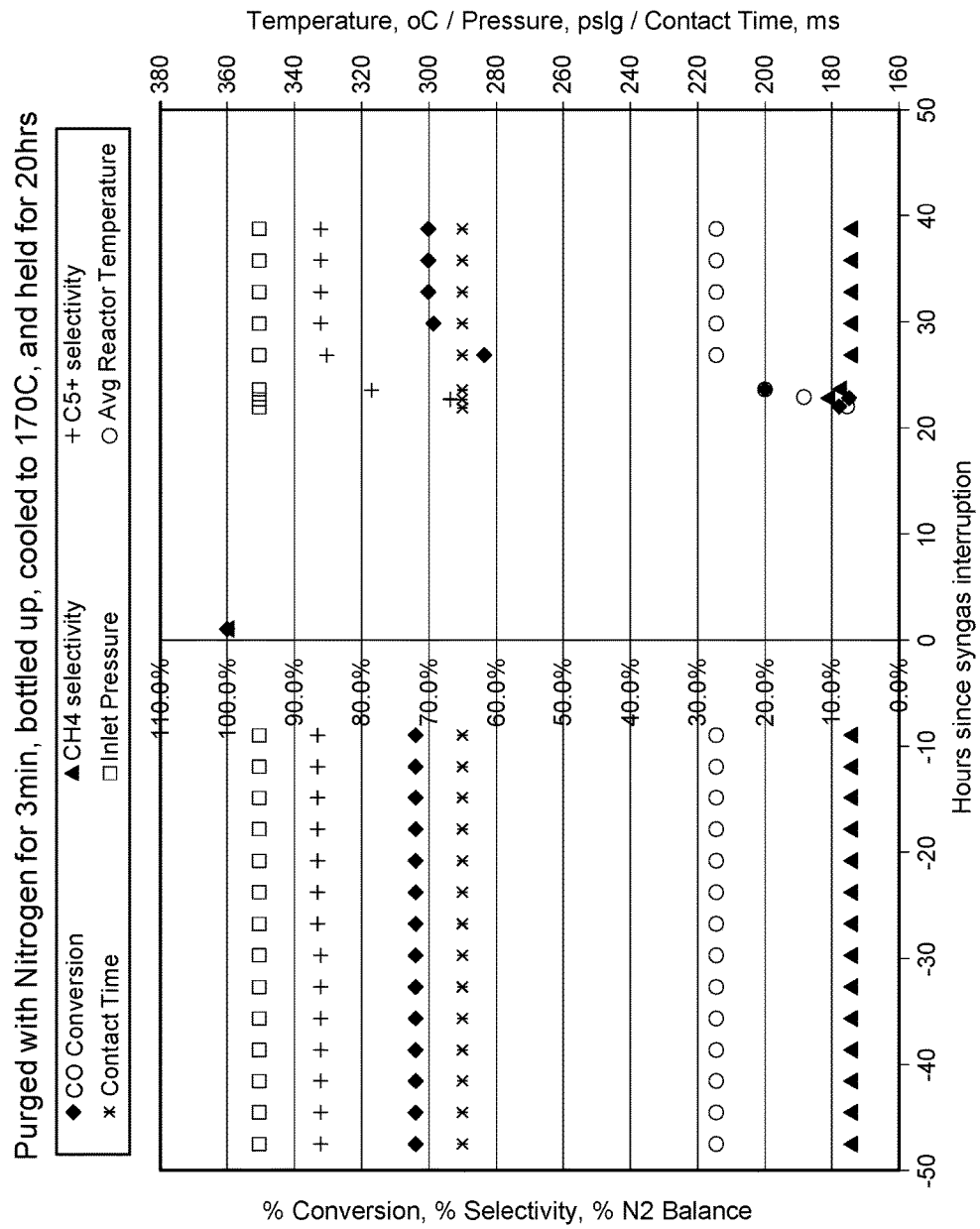
FIGS. 15-20 are charts showing the results of synthesis gas interruption tests discussed below in Examples 1-6.

Example 1 is provided for purposes of comparison. The test reported in Table 1 and FIG. 15, is conducted using a nitrogen purge followed by a fast reactor cool down to 170° C. Prior to the start of the stoppage, the microchannel reactor is operating under Fischer-Tropsch conditions with a synthesis gas feed having a $H_2$:CO molar ratio of 1.77, 32% by volume inerts with an inlet pressure of 350 psig (2413 kilopascals), and a contact time of 290 milliseconds. The average reactor operating temperature is 215° C. To perform synthesis stoppage, the synthesis gas feed is stopped and a nitrogen purge is introduced with a flow equivalent to a 1.6 second contact time for 3 minutes. The microchannel reactor is bottled and cooled to a temperature of 170° C. at a rate of 30° C. per hour. The temperature is held at 170° C. for 20 hours. The full flow of synthesis gas (290 milliseconds contact time) into the microchannel and the flow of effluent out of the reactor is then started. Once pre-synthesis stop conditions with feed gas at a $H_2$:CO molar ratio of 1.77 with 32% by volume inerts, inlet pressure of 350 psig (2413 kilopascals), and a contact time of 290 milliseconds are attained, the microchannel reactor is heated to the target (pre-stoppage) temperature at a rate of 15° C. per hour. This Example may be considered as representative of the prior art (with the exception of the temperature ramp rates used for reactor heat-up), and is provided for purposes of comparison. The results for this Example show a CO conversion loss of about 1.5% which would be equivalent to an activity temperature delta of 1.3° C. for the process. As calculated in Table 7, the relative activity ratio for this Example is 0.979.

TABLE 1

|  | 24 hrs avg before interrupt | 12-24 hrs avg after restart |
|---|---|---|
| CO conversion | 71.7% | 70.2% |
| $CH_4$ selectivity | 7.4% | 7.1% |
| $CO_2$ selectivity | 0.5% | 0.5% |
| $C_2$ selectivity | 0.8% | 1.0% |
| $C_3$ selectivity | 2.3% | 2.0% |
| $C_4$ selectivity | 2.8% | 3.0% |
| $C_5+$ selectivity | 86.2% | 85.9% |

Example 2

Figure 16:
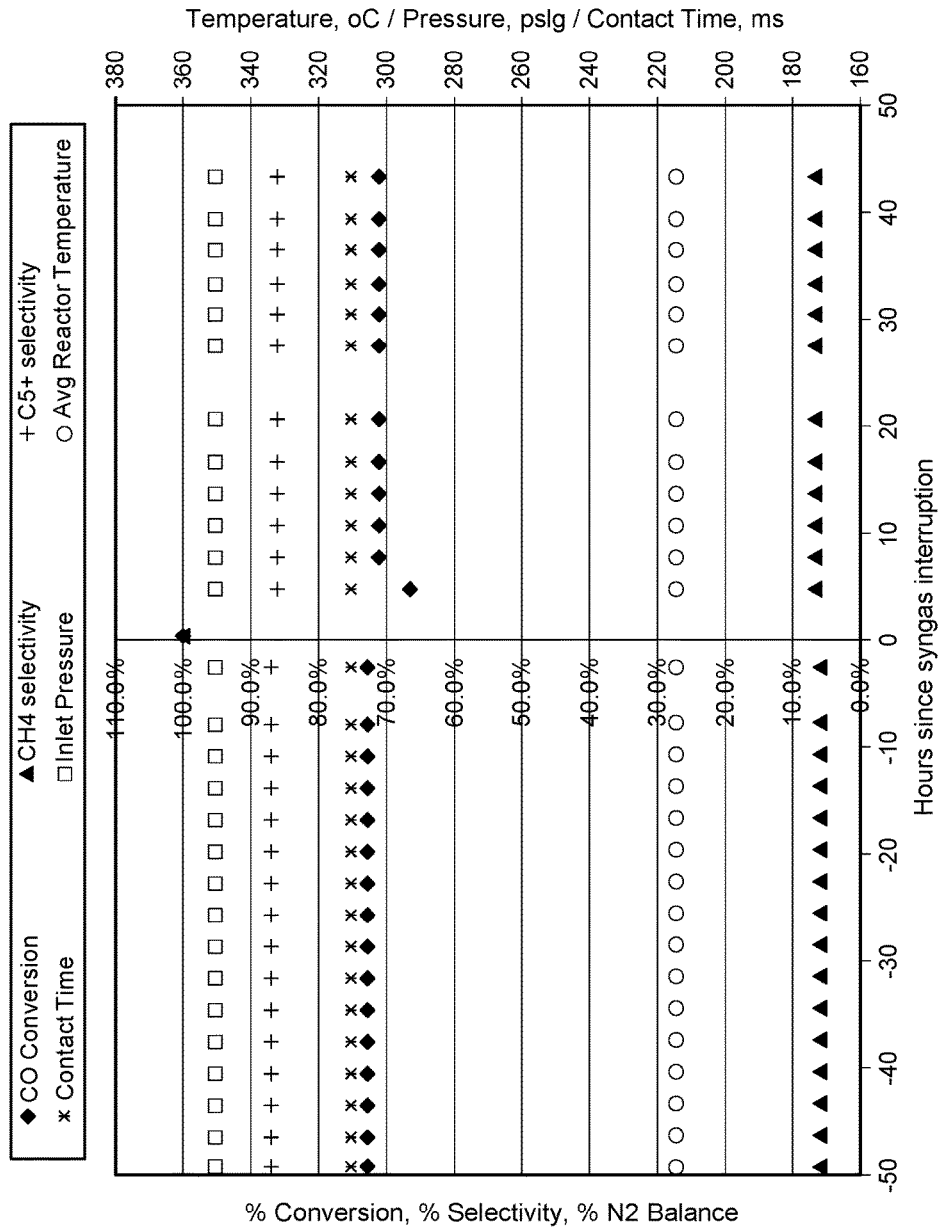

The test reported in Table 2 and FIG. 16, is conducted with the microchannel reactor bottled and simultaneously cooled down to 185° C. Prior to performing the process stoppage, the microchannel reactor is operating under Fischer-Tropsch conditions with a synthesis gas feed having $H_2$:CO molar ratio of 1.79, 28% by volume inerts with an inlet pressure of 350 psig (2413 kilopascals), and a contact time of 310 milliseconds. The average reactor operating temperature is 215° C. To perform synthesis stoppage, the synthesis gas feed is stopped and the flow of effluent out of the reactor is stopped and the reactor is cooled to 185° C. at a rate of 30° C. per hour, and then held at 185° C. for 1 hour. The flow of synthesis gas into the microchannel reactor and the flow of effluent out of the reactor is then started. The pre-synthesis stop conditions with feed gas at a $H_2$:CO molar ratio of 1.79 with 28% by volume inerts, inlet pressure of 350 psig (2413 kilopascals), and a contact time of 310 milliseconds are re-established within about 10-30 seconds. The microchannel reactor is heated to the target (pre-stoppage) temperature at a rate of 15° C. per hour. These tests show a similar level of CO conversion loss as the nitrogen purge described in comparative Example 1 which would be an activity temperature delta of about 1.3° C. As calculated in Table 7, the relative activity ratio for this Example is also 0.979. This procedure has the effect of eliminating the purge requirement and enables restoring the pre-stoppage conditions faster. This improves the availability of the reactor for synthesis operation relative to that in Example 1.

TABLE 2

|  | 24 hrs avg before interrupt | 12-24 hrs avg after restart |
|---|---|---|
| CO conversion | 72.6% | 71.1 |
| $CH_4$ selectivity | 6.6% | 6.9% |
| $CO_2$ selectivity | 0.4% | 0.4% |
| $C_2$ selectivity | 0.8% | 1.0% |
| $C_3$ selectivity | 2.3% | 2.7% |
| $C_4$ selectivity | 2.7% | 3.0% |
| $C_5+$ selectivity | 87.1% | 86.1% |

Example 3

Figure 17:
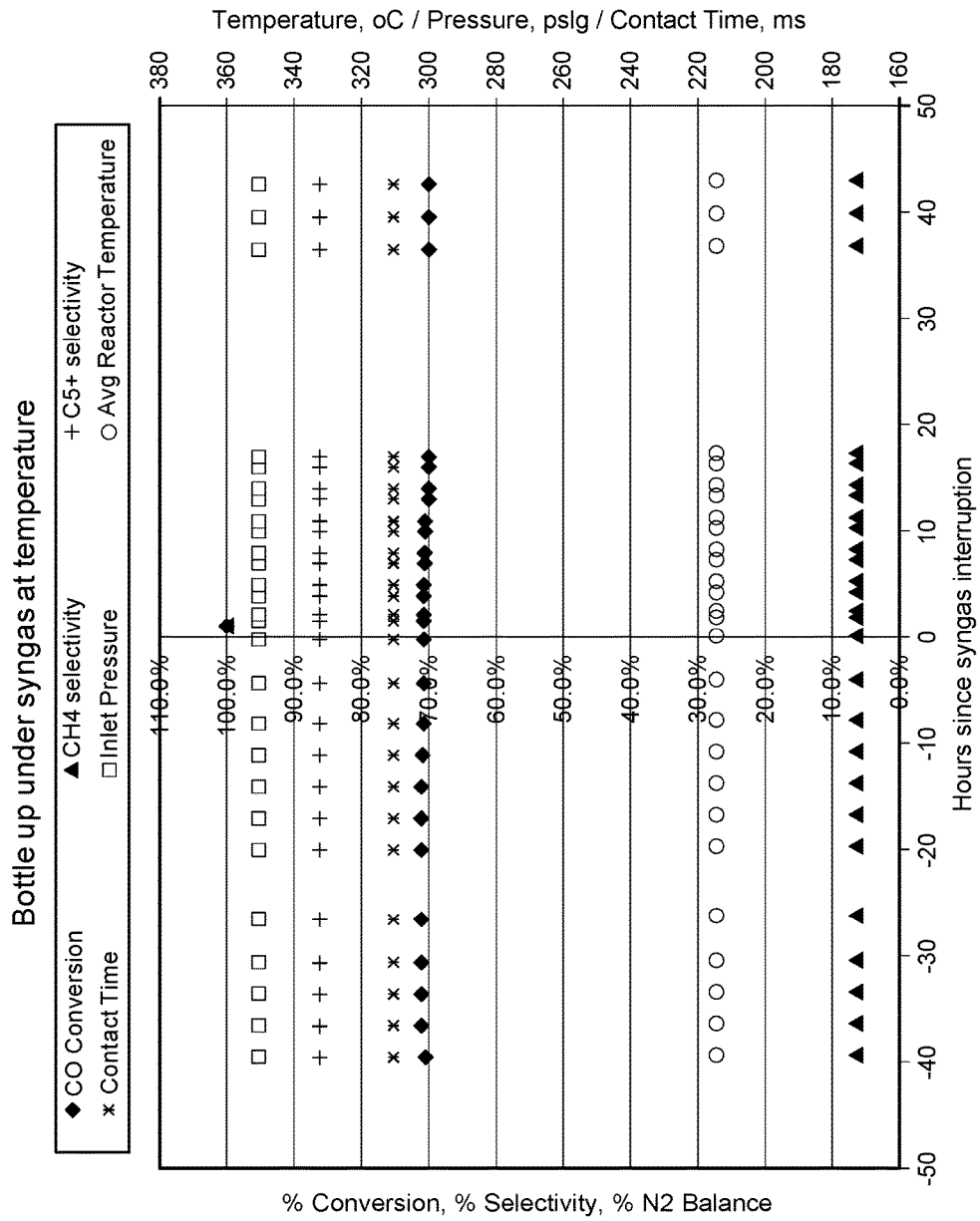

The test reported in Table 3 and FIG. 17, is conducted with the microchannel reactor bottledup at the reaction temperature of 215° C. Prior to performing the process stoppage, the microchannel reactor is operating under Fischer-Tropsch conditions with a synthesis gas feed having a $H_2$:CO molar ratio of 1.79, 28% by volume inerts with an inlet pressure of 350 psig (2413 kilopascals), and a contact time of 310 milliseconds. The average reactor operating temperature is 215° C. To simulate synthesis stoppage, the synthesis gas feed is stopped and the flow of effluent out of the reactor is stopped. The reactor temperature is maintained within ±1° C. of 215° C. during the bottling. At the end of a bottled period of 1 hour, the process is restarted with synthesis gas flowing into the reactor and effluent flowing out. The pre-synthesis stop conditions with feed gas at a $H_2$:CO molar ratio of 1.79 with 28% by volume inerts, inlet pressure of 350 psig (2413 kilopascals), and a contact time of 310 milliseconds are re-established within 10-30 seconds. There is a CO conversion loss of about 0.6% which represents a 50% improvement over the results shown in comparative Example 1. This corresponds to an activity temperature delta of 0.5° C. As calculated in Table 7, the relative activity ratio for this Example is 0.992. With this procedure, not only is the loss of catalyst activity significantly reduced, but the process also allows the reactor to be restarted by opening the reactor inlet and outlet to start flowing synthesis gas into the reactor and effluent out of the reactor in a matter of minutes, as the reactor is already at the target operating conditions. Given the concerns of carbon deposition (one of the primary causes of catalyst deactivation) on the catalyst under low hydrogen partial pressures (as $H_2$ will react to extinction), the decrease in loss of catalyst activity compared to the prior art shown in Example 1 is an unexpected and beneficial result.

TABLE 3

|  | 24 hrs avg before interrupt | 12-24 hrs avg after restart |
|---|---|---|
| CO conversion | 70.8% | 70.2% |
| $CH_4$ selectivity | 6.8% | 6.8% |
| $CO_2$ selectivity | 0.4% | 0.4% |
| $C_2$ selectivity | 0.9% | 1.0% |
| $C_3$ selectivity | 2.6% | 2.8% |
| $C_4$ selectivity | 3.0% | 3.1% |
| $C_5+$ selectivity | 86.3% | 85.9% |

Example 4

Figure 18:
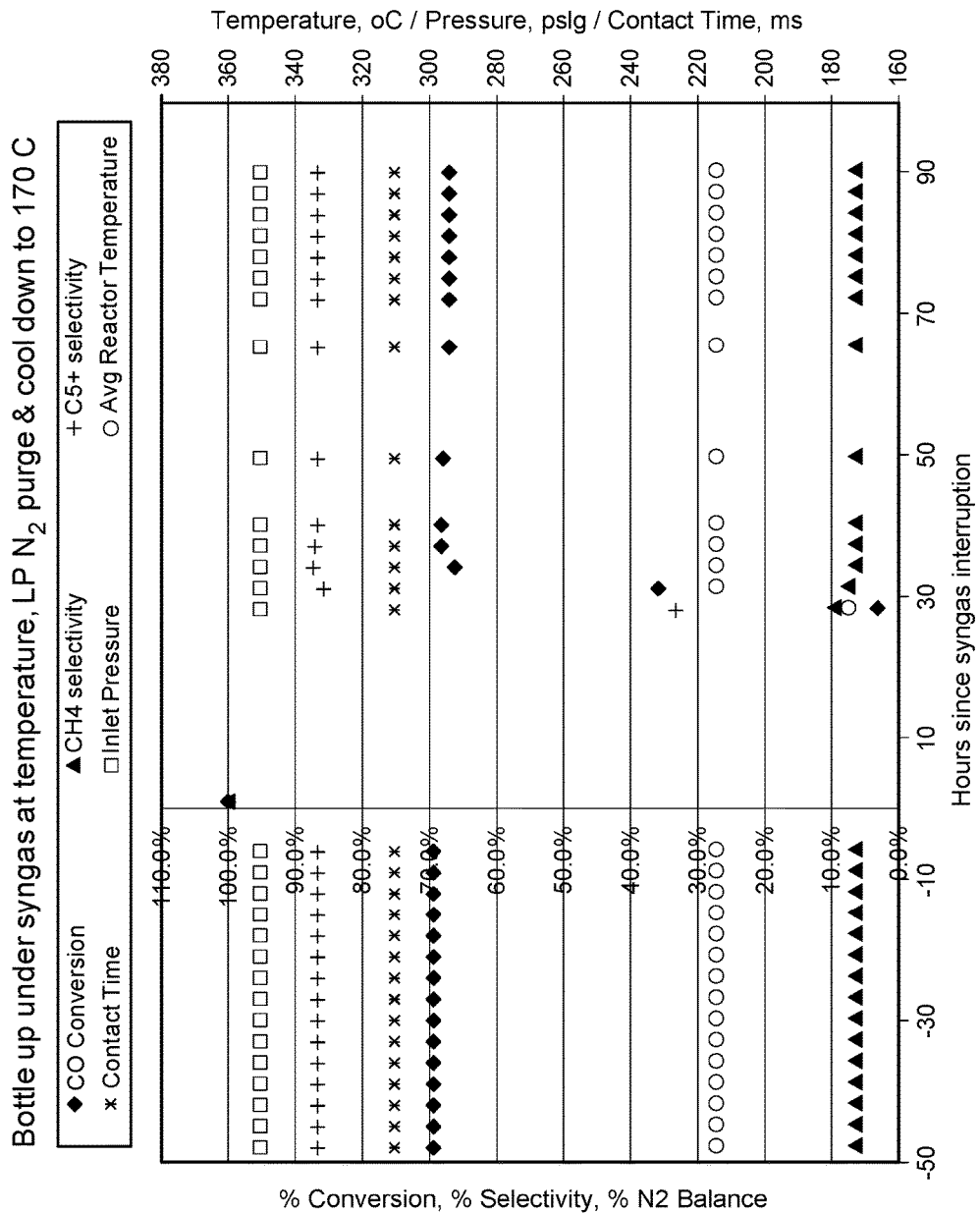

The test reported in Table 4 and FIG. 18, is conducted with the microchannel reactor bottled, followed by a low pressure nitrogen purge and slow cool down to 170° C. The process stoppage in this case would resemble a loss of coolant scenario where the initial response would be that of the reactor is bottled to be later followed by a nitrogen purge and slow cooling representative of the drop in reactor temperature with heat losses. Prior to performing the process stoppage, the microchannel reactor is operating under Fischer-Tropsch conditions with a synthesis gas feed having a $H_2$:CO molar ratio of 1.79, 28% by volume inerts with an inlet pressure of 350 psig (2413 kilopascals), and a contact time of 310 milliseconds. The average reactor operating temperature is 215° C. To simulate synthesis stoppage, the synthesis gas feed is stopped and the reactor is bottled for a period of 1 hour. At the end of 1 hour of bottled time, the pressure within the reactor is reduced from 350 psig (2413 kilopascals) to 35 psig (241.3 kilopascals) at a rate of 500 psi (3447 kilopascals) per hour. The microchannel reactor is then purged with $N_2$ at 125.8 standard cubic centimeters per minute (sccm) for 3 minutes. The microchannel reactor is then bottled for 24 hours under $N_2$ with a slow cooldown to 170° C. at a rate of 2° C. per hour. After 24 hours, the flow of synthesis gas into the microchannel reactor and the flow of effluent out of the microchannel reactor is then restarted. The pre-synthesis stop conditions with feed gas at a $H_2$:CO molar ratio of 1.79 with 28% by volume inerts and a contact time of 310 milliseconds are re-established within 10-30 seconds. The microchannel reactor is then pressurized to 350 psig (2413 kilopascals) and subsequently heated to the target (pre-stoppage) operating temperature at a rate of 15° C. per hour. The CO conversion loss after restart is 1.3%, which would be equivalent to an increase in the reactor temperature of 1.1° C., that is, an activity temperature delta of about 1° C. As calculated in Table 7, the relative activity ratio for this Example is 0.981.

TABLE 4

|  | 24 hrs avg before interrupt | 12-24 hrs avg after restart |
|---|---|---|
| CO conversion | 69.1% | 67.8% |
| $CH_4$ selectivity | 6.8% | 6.7% |
| $CO_2$ selectivity | 0.4% | 0.3% |
| $C_2$ selectivity | 0.9% | 1.0% |
| $C_3$ selectivity | 2.5% | 2.7% |
| $C_4$ selectivity | 2.9% | 3.0% |
| $C_5$+ selectivity | 86.5% | 86.2% |

Example 5

Figure 19:
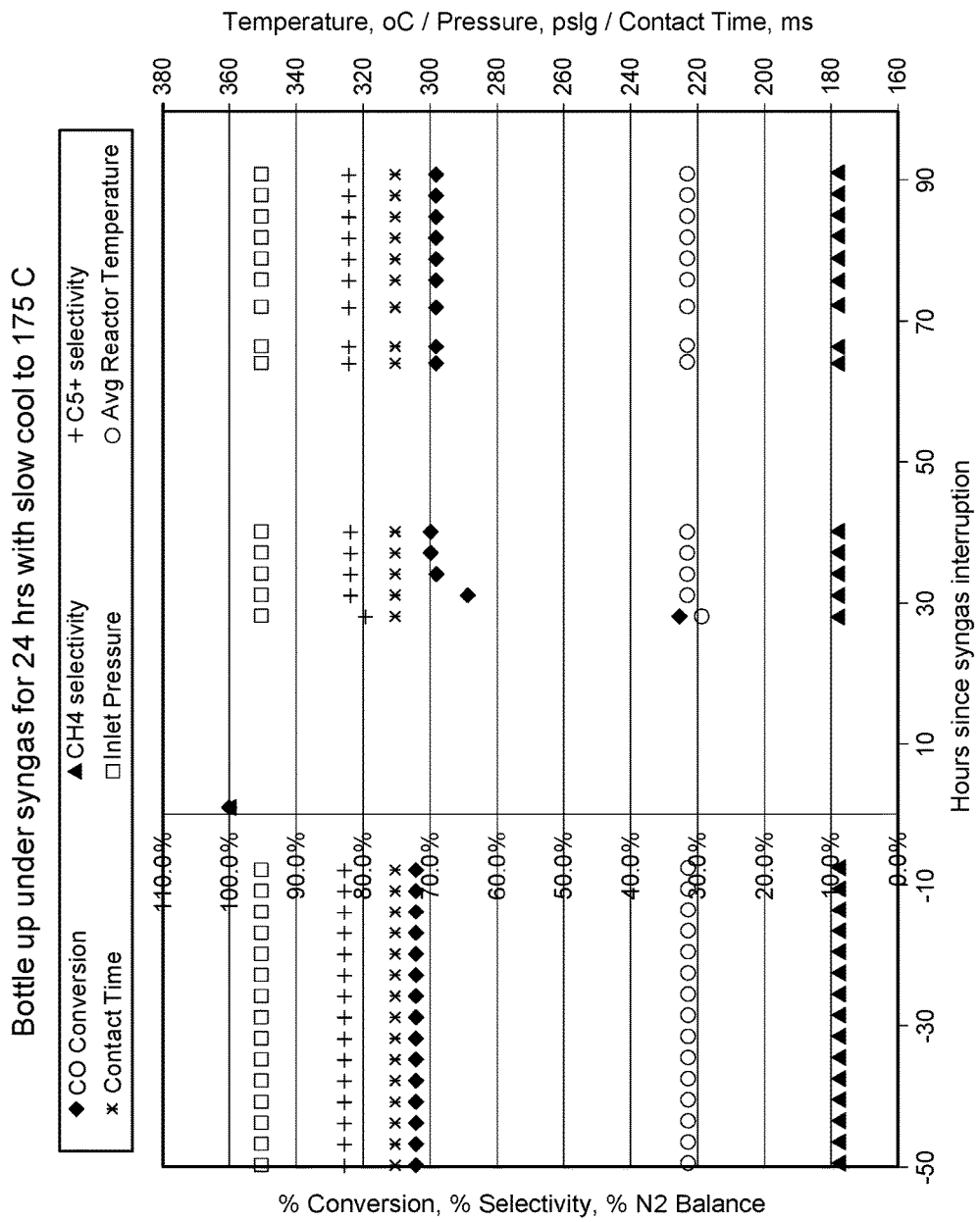
Figure 20:
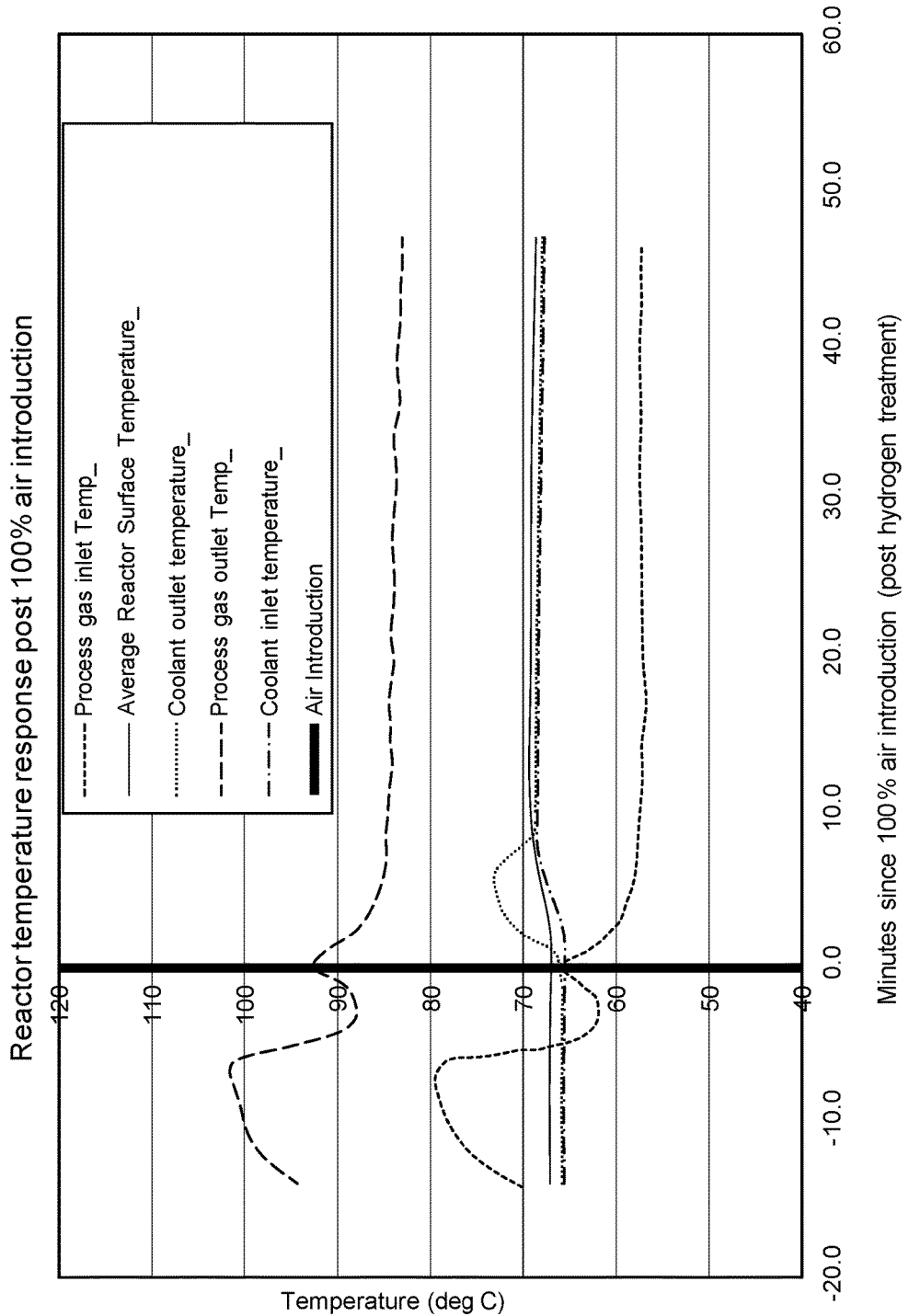

The test reported in Table 5 and FIG. 19 is conducted with the microchannel reactor bottled for 1 hour and then slowly cooled down to 175° C. Prior to performing the process stoppage, the microchannel reactor is operating under Fischer-Tropsch conditions with a syngas feed having a $H_2$:CO molar ratio of 1.79, 28% by volume inerts with an inlet pressure of 350 psig (2413 kilopascals), and a contact time of 310 milliseconds. The average reactor operating temperature is 223° C. To simulate synthesis stoppage, the synthesis gas feed is stopped and the reactor is bottled for a period of 1 hour. At the end of 1 hour of bottling time, the microchannel reactor is cooled down to 175° C. at a rate of 2° C. per hour. After 24 hours, the flow of synthesis gas into the reactor and the flow of effluent out of the reactor are started. The pre-synthesis stop conditions with feed gas at a $H_2$:CO molar ratio of 1.79 with 28% by volume inerts, inlet pressure of 350 psig (2413 kilopascals), and a contact time of 310 milliseconds are re-established within 10-30 seconds. The microchannel reactor is heated to the pre-stoppage reaction temperature at a rate of 15° C. per hour. This is a modification of the test shown in Example 4 to eliminate the use of an inert $N_2$ purge to achieve a similar loss in CO conversion by mere bottling of the reactor under operating synthesis gas. The bottled reactor under synthesis gas is shown to have a CO conversion loss of about 2.1%, which would be equivalent to an activity temperature delta of 1.7° C. As calculated in Table 7, the relative activity ratio for this Example is 0.971.

TABLE 5

|  | 24 hrs avg before interrupt | 12-24 hrs avg after restart |
|---|---|---|
| CO conversion | 71.8% | 69.7% |
| $CH_4$ selectivity | 8.6% | 9.0% |
| $CO_2$ selectivity | 0.7% | 0.7% |
| $C_2$ selectivity | 1.3% | 1.4% |
| $C_3$ selectivity | 3.1% | 3.5% |
| $C_4$ selectivity | 3.6% | 4.0% |
| $C_5$+ selectivity | 82.6% | 81.4% |

Example 6

A series of synthesis gas interruption tests are conducted using a multi-channel Fischer-Tropsch microchannel reactor. The results are reported in Table 6 and FIG. 20. The microchannel reactor has 850 process microchannels (arranged in two layers) with dimensions similar to the single channel described above for Examples 1-5. A supported cobalt catalyst in the form of a fixed bed of particulate solids is loaded in the process microchannels with a bed length of 40 cm. Each of the process layers has an adjacent coolant layer. Each coolant layer has 128 coolant microchannels. Partial boiling heat transfer is used to remove the reaction heat by flowing water in the coolant circuits. Headers and footers are attached for the coolant and process microchannels to have external connections to macroscale (i.e., larger), piping.

The Fischer-Tropsch synthesis process conditions in the reactor are interrupted, and then a hydrogen treatment is performed at a temperature of 350-375° C. Following this treatment the reactor is cooled to a temperature of 70° C. and 100% air (21% $O_2$) is introduced into the reactor. The exotherm is controlled by adjusting one or more of the air flow, coolant flow, and coolant temperature. It is preferred to maintain the exotherm during the air treatment to less than a 15° C. temperature rise, or less than 10° C., or less than 5° C. The catalyst is oxidized during the air treatment. Cobalt oxidation with air is a highly exothermic reaction. Despite this only a minor temperature increase of about 7° C. is observed in this example in the coolant outlet temperature due to the excellent heat transfer characteristics of the microchannel reactor. This is well within a level that can be tolerated by the reactor coolant system without a negative impact on the catalyst activity. This result enables the use of low pressure air for performing catalyst oxidation using simplified equipment provided that the flow of air is controlled in order to avoid excessive catalyst temperatures. It also eliminates the need for blending of the air with a $N_2$ stream to dilute the oxygen concentration, which in turn significantly reduces the need for nitrogen availability at the plant site.

Following a final reduction treatment in a flowing hydrogen environment at a temperature of about 350° C., the catalyst is brought to the target operating conditions in 18 hours. Because of the oxidative regeneration, the catalyst activity is restored to a level higher than that before the interruption of the Fischer-Tropsch synthesis process. The H$_2$:CO molar ratio is 1.83, with 41% by volume inerts. The inlet pressure is 350 psig (2413 kilopascals). The contact time is 355 to 360 milliseconds. Using this regenerative procedure, the activity temperature delta is reduced to −16° C. In the Table 6 below, all percentages are by volume. As calculated in Table 7, the relative activity ratio for this Example is 4.036.

TABLE 6

|  | 24 hrs avg before interrupt | 12-24 hrs avg after restart |
|---|---|---|
| Avg. reactor temperature | 218° C. | 202° C. |
| CO conversion | 69.3% | 70.9% |
| CH$_4$ selectivity | 10.4% | 9.2% |
| C$_2$ selectivity | 1.6% | 1.0% |
| C$_3$ selectivity | 3.3% | 2.3% |
| C$_4$ selectivity | 3.2% | 2.7% |
| C$_5$+ selectivity | 80.1% | 84.4% |

Table 7 below summarizes the calculation of relative activity ratio for the Examples 1-6 using the process performance data and the intrinsic kinetic model from Yates & Satterfield as described above.

TABLE 7

| Example | Inlet Pressure (psig) | H2:CO | inerts | Partial pressure H2 (atm) | Partial pressure CO (atm) | Contact time (ms) | GHSV (1/h) | CO flow to reactor (v/vcat/h) |
|---|---|---|---|---|---|---|---|---|
| 1 | 350 | 1.77 | 32% | 10.78 | 6.09 | 290 | 12414 | 3047 |
| 2 | 350 | 1.79 | 28% | 11.46 | 6.40 | 310 | 11613 | 2997 |
| 3 | 350 | 1.79 | 28% | 11.46 | 6.40 | 310 | 11613 | 2997 |
| 4 | 350 | 1.79 | 28% | 11.46 | 6.40 | 310 | 11613 | 2997 |
| 5 | 350 | 1.79 | 28% | 11.46 | 6.40 | 310 | 11613 | 2997 |
| 6 | 350 | 1.83 | 41% | 9.47 | 5.17 | 358 | 10056 | 2096 |

| | before | | | | after | | | | | |
|---|---|---|---|---|---|---|---|---|---|---|
| Example | CO conv | ART (C) | CO reacted v/vcat/h | YS rate v/vcat/h | activity (CO reacted/ YS rate) | CO conv | ART (C) | CO reacted v/vcat/h | YS rate v/vcat/h | activity (CO reacted/ YS rate) | relative activity ratio (activity-after/ activity-before) |
| 1 | 71.7% | 215.0 | 2185.0 | 146.5 | 14.9 | 70.2% | 215.0 | 2139.3 | 146.5 | 14.6 | 0.979 |
| 2 | 72.6% | 215.0 | 2175.7 | 149.0 | 14.6 | 71.1% | 215.0 | 2130.8 | 149.0 | 14.3 | 0.979 |
| 3 | 70.8% | 215.0 | 2121.8 | 149.0 | 14.2 | 70.2% | 215.0 | 2103.8 | 149.0 | 14.1 | 0.992 |
| 4 | 69.1% | 215.0 | 2070.8 | 149.0 | 13.9 | 67.8% | 215.0 | 2031.9 | 149.0 | 13.6 | 0.981 |
| 5 | 71.8% | 223.0 | 2151.8 | 287.9 | 7.5 | 69.7% | 223.0 | 2088.8 | 287.9 | 7.3 | 0.971 |
| 6 | 69.3% | 218.0 | 1452.8 | 190.2 | 7.6 | 70.9% | 202.0 | 1486.4 | 48.2 | 30.8 | 4.036 |

While the invention has been explained in relation to various embodiments, it is to be understood that various modifications thereof will become apparent to those skilled in the art upon reading the specification. Therefore, it is to be understood that the invention disclosed herein includes any such modifications that may fall within the scope of the appended claims.

The invention claimed is:

1. A method for stopping and restarting a Fischer-Tropsch reaction process, wherein the Fischer-Tropsch process comprises flowing synthesis gas into a microchannel reactor in contact with a Fischer-Tropsch catalyst at a desired reaction temperature and pressure to produce a Fischer-Tropsch product and flowing effluent comprising the Fischer-Tropsch product out of the reactor, wherein the catalyst is in the form of a fixed bed of particulate solids, the particulate solids having a median particle diameter in the range from about 1 to about 1000 microns, the method comprising:

(A) bottling the reactor by stopping the flow of the synthesis gas into the reactor and the flow of the effluent out of the reactor for a period of time in the range from about 0.1 to about 48 hours while maintaining the temperature within the microchannel reactor at the desired reaction temperature, wherein during the stoppage synthesis gas remains in the reactor in contact with the catalyst;

(B) flowing nitrogen gas into the reactor to purge the reactor and restarting the flow of effluent out of the reactor; and (C) restarting the flow of synthesis gas into the reactor; wherein the desired reaction temperature is controlled with a heat exchange fluid flowing in a heat exchanger in thermal contact with the reactor, the temperature of the heat exchange fluid in the heat exchanger being up to about 10° C. lower than the desired reaction temperature; and wherein the synthesis gas comprises CO and prior to stopping the flow of synthesis gas into the reactor the conversion of CO is at a desired conversion value, and after restarting the flow of synthesis gas into the reactor the conversion of CO at the desired conversion value is achieved within a time period of up to about 3 hours.

2. The method of claim 1 wherein the synthesis gas comprises fresh synthesis gas, the fresh synthesis gas comprising CO, the conversion of CO from the fresh synthesis gas being at least about 70%.

3. The method of claim 1 wherein the selectivity to methane in the Fischer-Tropsch product is in the range from about 0.01 to 10%.

4. The method of claim 1 wherein the microchannel reactor comprises a plurality of layers of process microchannels and a plurality of layers of heat exchange channels, the catalyst being in the process microchannels, each layer of heat exchange channels being in thermal contact with at least one layer of process microchannels, a header for flowing reactants into the process microchannels, a footer for receiving product flowing out of the process microchannels, a header for flowing a heat exchange fluid into the heat exchange channels, and a footer for receiving heat exchange fluid flowing out of the heat exchange channels.

5. The method of claim 4 wherein the heat exchange channels are microchannels.

6. The method of claim 1 wherein the reaction temperature is in the range from about 150 to about 300° C.

7. The method of claim 1 wherein prior to the step of restarting the flow of synthesis gas into the reactor, the temperature within the reactor is below the desired reaction temperature, the temperature of the reactor being increased to the desired reaction temperature at a rate of up to about 60° C. per hour.

8. The method of claim 1 wherein prior to stopping the flow of synthesis gas into the reactor, the temperature in the reactor is at a desired operating temperature, and during the period of time between stopping the flow of synthesis gas into the reactor and restarting the flow of synthesis gas into the reactor the temperature in the reactor is within about 20° C. of the desired operating temperature.

9. The method of claim 1 wherein the activity temperature delta for the process after restarting the flow of synthesis gas into the reactor is up to about 5° C.

10. A method for stopping and restarting a Fischer-Tropsch reaction process, wherein the Fischer-Tropsch reaction process comprises flowing synthesis gas into a microchannel reactor in contact with a Fischer-Tropsch catalyst at a desired reaction temperature and pressure to produce a Fischer-Tropsch product and flowing effluent comprising the Fischer-Tropsch product out of the reactor, wherein the catalyst is in the form of a fixed bed of particulate solids, the particulate solids having a median particle diameter in the range from about 1 to about 1000 microns, the method comprising:
(A) bottling the reactor by stopping the flow of the synthesis gas into the reactor and the flow of the effluent out of the reactor for a period of time in the range from about 0.1 to about 48 hours, wherein during the stoppage synthesis gas remains in the reactor in contact with the catalyst; wherein prior to step (A) the pressure within the reactor is at a pre-stoppage pressure and during step (A) the pressure within the reactor is reduced to a level lower than the pre-stoppage pressure;
(B) restoring the pressure within the reactor to the pre-stoppage pressure;
(C) flowing nitrogen gas into the reactor to purge the reactor and restarting the flow of effluent out of the reactor; and
(D) restarting the flow of the synthesis gas into the reactor;
wherein the desired reaction temperature is controlled with a heat exchange fluid flowing in a heat exchanger in thermal contact with the reactor, the temperature of the heat exchange fluid in the heat exchanger being up to about 10° C. lower than the desired reaction temperature; and
wherein the synthesis gas comprises CO and prior to stopping the flow of synthesis gas into the reactor the conversion of CO is at a desired conversion value, and after restarting the flow of synthesis gas into the reactor the conversion of CO at the desired conversion value is achieved within a time period of up to about 3 hours.

11. A method for stopping and restarting a Fischer-Tropsch reaction process, wherein the Fischer-Tropsch reaction process comprises flowing synthesis gas into a microchannel reactor in contact with a Fischer-Tropsch catalyst at a desired reaction temperature and pressure to produce a Fischer-Tropsch product and flowing effluent comprising the Fischer-Tropsch product out of the reactor, wherein the catalyst is in the form of a fixed bed of particulate solids, the particulate solids having a median particle diameter in the range from about 1 to about 1000 microns, the method comprising:
(A) bottling the reactor by stopping the flow of synthesis gas into the reactor and the flow of effluent out of the reactor and reducing the temperature in the reactor to a reduced temperature below the desired reaction temperature for a period of time in the range from about 0.1 to about 48 hours, wherein during the stoppage synthesis gas remains in the reactor in contact with the catalyst;
(B) increasing the temperature in the reactor to the desired reaction temperature at a rate of up to about 60° C. per hour;
(C) flowing nitrogen gas into the reactor to purge the reactor and restarting the flow of effluent out of the reactor; and
(D) restarting the flow of synthesis gas into the reactor;
wherein the desired reaction temperature is controlled with a heat exchange fluid flowing in a heat exchanger in thermal contact with the reactor, the temperature of the heat exchange fluid in the heat exchanger being up to about 10° C. lower than the desired reaction temperature; and
wherein the synthesis gas comprises CO and prior to stopping the flow of synthesis gas into the reactor the conversion of CO is at a desired conversion value, and after restarting the flow of synthesis gas into the reactor the conversion of CO at the desired conversion value is achieved within a time period of up to about 3 hours.

12. The method of claim 11 wherein the Fischer-Tropsch catalyst comprises a wet catalyst.

13. A method of stopping and restarting a Fischer-Tropsch reaction process wherein the process is conducted in a plant comprising a plurality of reaction trains, each reaction train comprising a Fischer-Tropsch microchannel reactor containing a Fischer-Tropsch catalyst, each reaction train being connected to a reactant feed stream comprising fresh synthesis gas, the method comprising:
(A) flowing the reactant feed stream at an overall process flow rate to the plurality of reaction trains in the plant;
(B) dividing the reactant feed stream into a plurality of reactant substreams;
(C) flowing each reactant substream through a reaction train to convert the reactants in each reactant substream to a Fischer-Tropsch product;
(D) bottling the microchannel reactor in one of the reaction trains by stopping the flow of a reactant substream to the microchannel reactor in the one reaction train and stopping the flow of effluent out of the microchannel reactor in the one reaction train for a period of time in the range from about 0.1 to about 48 hours, and then restarting the flow of the reactant substream to the microchannel reactor in the one reaction train and the flow of effluent out of the microchannel reactor in the one reaction train; and
(E) continuing to flow the reactant feed stream to the remainder of reaction trains in the plant, wherein the overall process flow rate of fresh synthesis gas to the plant is substantially the same as the flow rate of fresh synthesis gas used in step (A);
wherein the desired reaction temperature in the reactor of the one reaction train is controlled with a heat exchange fluid flowing in a heat exchanger in thermal contact with the reactor of the one reaction train, the temperature of the heat exchange fluid being up to about 10° C. lower than the desired reaction temperature; and wherein the synthesis gas comprises CO and prior to stopping the flow of synthesis gas into the reactor of the one reaction train the conversion of CO is at a desired conversion value, and after restarting the flow of synthesis gas into the reactor of the one reaction train the conversion of CO at the desired conversion value is achieved within a time period of up to about 3 hours.

* * * * *